United States Patent
Agejas-Chicharro et al.

(10) Patent No.: US 7,335,660 B2
(45) Date of Patent: Feb. 26, 2008

(54) ISOCHROMAN COMPOUNDS FOR TREATMENT OF CNS DISORDERS

(75) Inventors: Javier Agejas-Chicharro, Alcobendas-Madrid (ES); Graham Henry Timms, Basingstoke (GB); Andrew Caerwyn Williams, Basingstoke (GB); Nicholas Paul Camp, Basingstoke (GB); Jeremy Gilmore, Basingstoke (GB); Ana Belen Bueno Melendo, Alcobendas-Madrid (ES); Carlos Lamas-Peteira, Alcobendas-Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 367 days.

(21) Appl. No.: 10/496,535

(22) PCT Filed: Dec. 6, 2002

(86) PCT No.: PCT/US02/36148

§ 371 (c)(1),
(2), (4) Date: May 24, 2004

(87) PCT Pub. No.: WO03/053948

PCT Pub. Date: Jul. 3, 2003

(65) Prior Publication Data
US 2005/0014750 A1 Jan. 20, 2005

(30) Foreign Application Priority Data
Dec. 19, 2001 (GB) .................................. 0130339.5

(51) Int. Cl.
| | | |
|---|---|---|
| A61K 31/496 | (2006.01) | |
| C07D 311/76 | (2006.01) | |
| C07D 405/06 | (2006.01) | |
| C07D 409/12 | (2006.01) | |
| C07D 413/12 | (2006.01) | |
| C07D 413/06 | (2006.01) | |
| C07D 413/14 | (2006.01) | |
| C07D 413/04 | (2006.01) | |
| C07D 407/06 | (2006.01) | |
| C07D 409/14 | (2006.01) | |
| C07D 405/04 | (2006.01) | |
| C07D 417/12 | (2006.01) | |
| C07D 405/12 | (2006.01) | |

(52) U.S. Cl. ............................ 514/254.11; 514/254.01; 514/254.02; 514/254.04; 514/254.05; 514/254.07; 544/366; 544/367; 544/369; 544/370; 544/372; 544/376

(58) Field of Classification Search ...................... None
See application file for complete search history.

(56) References Cited

U.S. PATENT DOCUMENTS 4,247,553 A 1/1981 McCall

FOREIGN PATENT DOCUMENTS

| WO | WO 95 18118 A | 7/1995 |
| WO | WO 97 02259 A | 1/1997 |
| WO | WO 02 50067 A | 6/2004 |

OTHER PUBLICATIONS

Robichaud et al. in Annual Reports in Medicinal Chemistry, vol. 36, p. 11-20 (2000).*
Slassi, Current Topics in Medicinal Chemistry, vol. 2, p. 559-574 (2002).*

* cited by examiner

*Primary Examiner*—Emily Bernhardt
(74) *Attorney, Agent, or Firm*—Paul J. Gaylo; Tonya L. Combs

(57) ABSTRACT

This invention relates to compounds of formula (I)

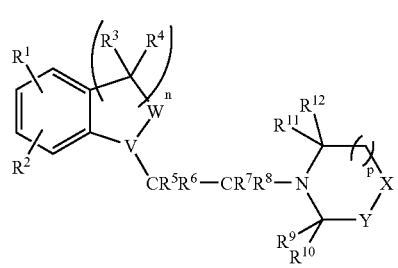

where $R^1$ to $R^{12}$, —W—V—, —X—Y—, p and n have the values defined in claim 1, their preparation and use as pharmaceuticals for the treatment of central nervous system disorders, such as depression, bipolar disorder, and anxiety.

13 Claims, No Drawings

ISOCHROMAN COMPOUNDS FOR TREATMENT OF CNS DISORDERS

This invention relates to novel compounds, their preparation and use as pharmaceuticals.

Certain isochroman compounds useful as antipsychotics and in the treatment of disorders of the central nervous system, are disclosed in WO 95/18118 and WO 97/02259.

The compounds of the invention are of the following general formula:

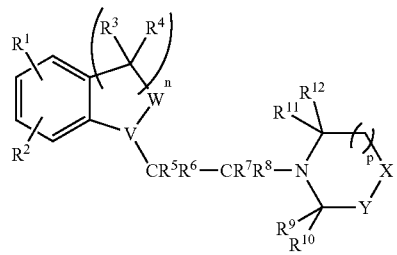

(I)

in which
$R^1$ is any one of
—CN, —CONR$^{13}$R$^{14}$, —SO$_2$NR$^{13}$R$^{14}$, —(CH$_2$)$_r$—R$^{21}$,

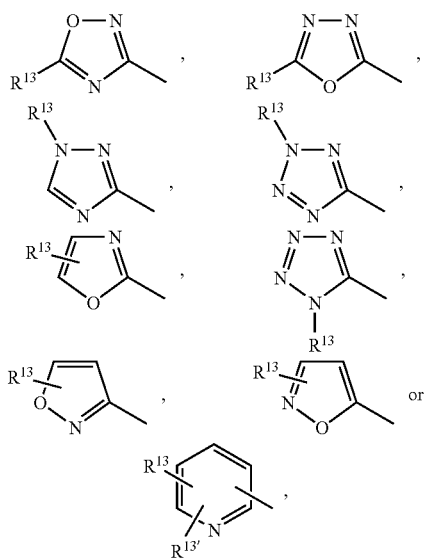

—R$^{21}$ is any one of

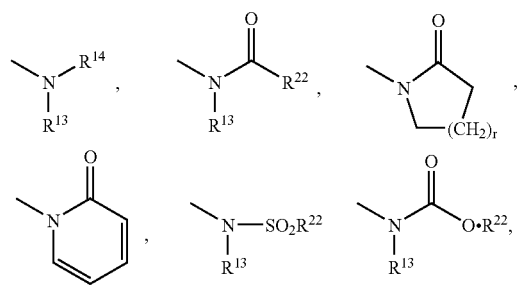

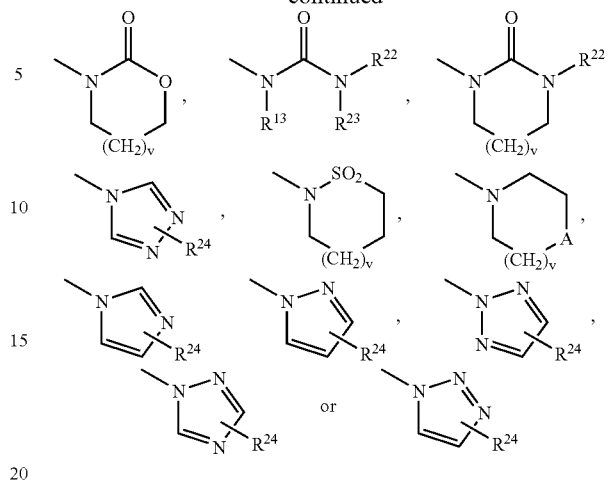

where $R^{13}$, $R^{14}$, $R^{22}$ and $R^{23}$ are each hydrogen or $C_{1-6}$ alkyl, or $R^{13}$ and $R^{14}$ taken together with the nitrogen atom to which they are attached form a morpholino, pyrrolidino or piperidinyl ring optionally substituted with one or two $C_{1-6}$ alkyl groups.

$R^{13'}$ and $R^{24}$ are each independently selected from hydrogen, $C_{1-6}$ alkyl, $C_{1-6}$ alkoxy, carboxy, hydroxy, cyano, halo, trifluoromethyl, nitro, amino, $C_{1-6}$ acylamino, $C_{1-6}$ alkylthio, phenyl or phenoxy.

A is O or S
t is 0, 1 or 2,
r is 0, 1, 2 or 3,
v is 0, 1 or 2;
$R^2$ is hydrogen, $C_{1-6}$ alkyl, $C_{1-6}$ alkoxy or halo;
$R^3$, $R^4$, $R^5$, $R^6$, $R^7$, and $R^8$ are each hydrogen or $C_{1-6}$ alkyl;
$R^9$, $R^{10}$, $R^{11}$ and $R^{12}$ are each hydrogen, $C_{1-6}$ alkyl or —(CH$_2$)$_q$—OR$^{20}$, wherein $R^{20}$ is $C_{1-6}$ alkyl;
n is 1 or 2;
p is 0, 1 or 2;
q is 1 or 2;

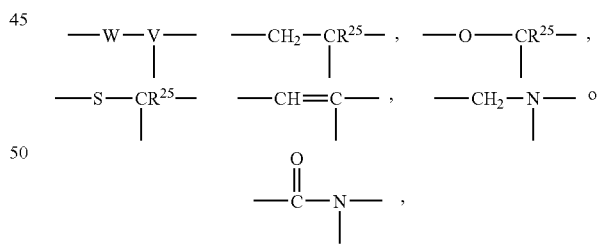

is any one of
$R^{25}$ is hydrogen or $C_{1-6}$ alkyl;
—X—Y— is

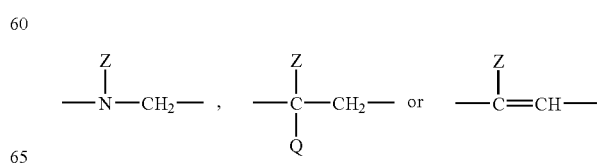

where Z is any one of
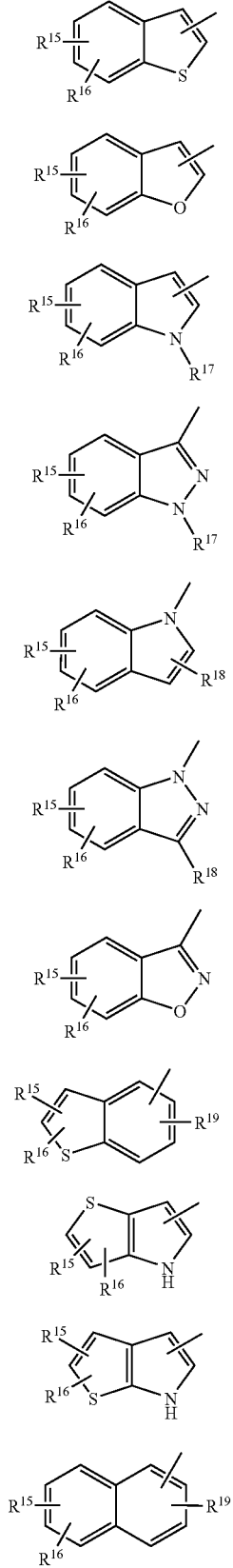
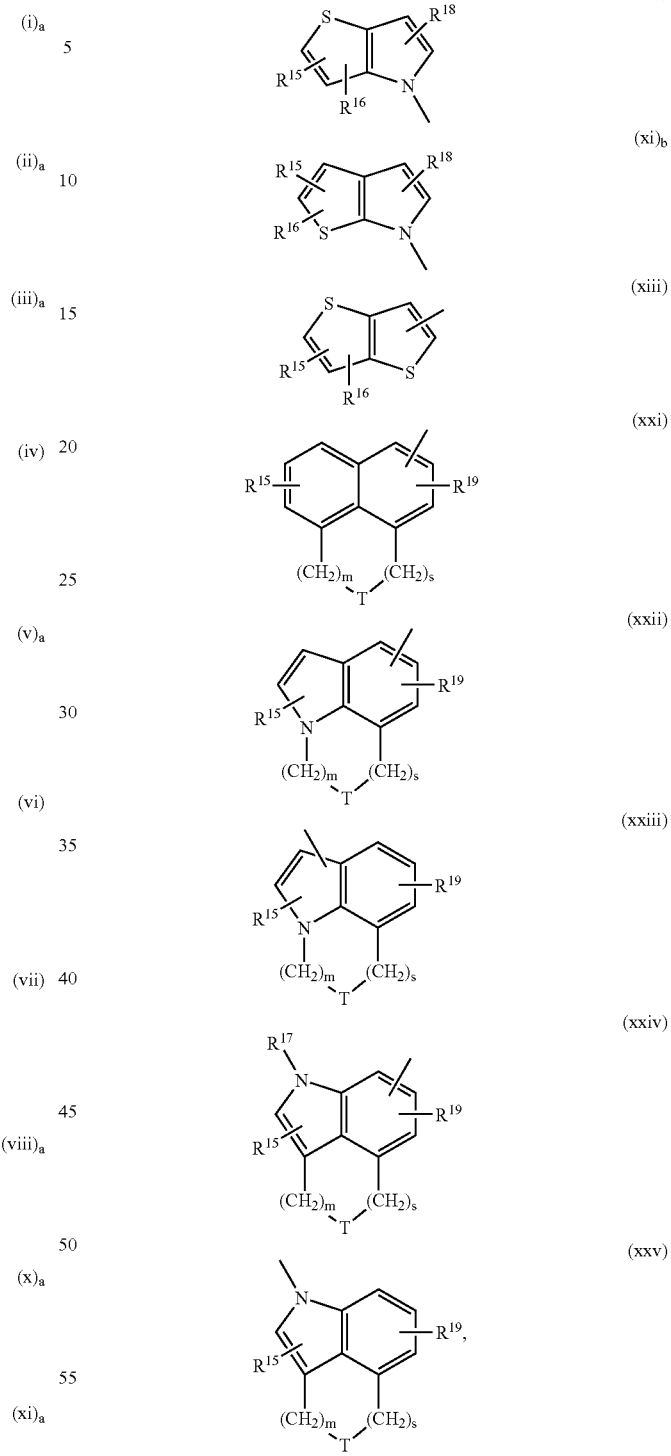
in which -T- is —$CH_2$—, —O—, —S—, —C(O)— or —CH=CH—, m and s are each 0 or 1,
$R^{15}$, $R^{16}$ and $R^{19}$ are each hydrogen, halo, $C_{1-6}$ alkyl or $C_{1-6}$ alkoxy, carboxy-$C_{1-6}$ alkyl, cyano, halogen, trifluoromethyl, trifluoromethoxy, nitro, amino, $C_1$-$C_6$ acylamino or $C_1$-$C_6$ alkylthio and $R^{17}$ and $R^{18}$ are each hydrogen or $C_{1-6}$ alkyl, Q is hydrogen, halo, nitrile, carboxy-$C_{1-6}$ alkyl, hydroxy, $C_{1-6}$ alkyl or $C_{1-6}$ alkoxy; and pharmaceutically acceptable salts thereof; provided that:
a) when -T- is —$CH_2$—, —O—, —S— or —C(O)—, then (m+s) is 1 or 2, and
b) when Z is (i)$_a$, (ii)$_a$, (iii)$_a$, (iv), (v)$_a$, (vi), (vii), (viii)$_a$, (x)$_a$, (xi)$_a$, (xii)$_a$, (x)$_b$, (xi)$_b$ or (xiii), then $R^1$ is —$(CH_2)_t$—$R^{21}$.

The compounds of the invention and their pharmaceutically acceptable salts are indicated for use as a pharmaceutical. Particularly the compounds of the invention and their pharmaceutically acceptable salts are indicated for use in the treatment of disorders of the central nervous system.

Accordingly the present invention also includes the use of a compound of formula I or a pharmaceutically acceptable salt thereof in the manufacture of a medicament for the treatment of a disorder of the central nervous system in mammals. The present invention also includes a method of treating an animal, including a human, suffering from or susceptible to a disorder of the central nervous system, which comprises administering a therapeutically effective amount of a compound of formula I or a pharmaceutically acceptable salt thereof.

In the above formula (I), a $C_{1-6}$ alkyl group can be branched or unbranched and, for example, includes methyl, ethyl, propyl, isopropyl, butyl, isobutyl, t-butyl, pentyl and hexyl, and is preferably methyl or ethyl, and especially methyl. A $C_{1-6}$ alkoxy group is one such alkyl group linked to a ring through an oxygen atom, and is preferably methoxy or ethoxy, and especially methoxy. A halo group is fluoro, chloro or bromo, and especially fluoro. A ($C_1$-$C_6$)alkylthio is an alkyl group linked to a sulphur atom, where the alkyl group is as defined above. A ($C_1$-$C_6$)alkylthio group includes for example thiomethyl or thioethyl. A $C_1$-$C_6$ acylamino group is an alkyl group linked to an amide group, where the alkyl is as defined above, and is preferably of the formula $R^{IV}$—NH—CO— where $R^{IV}$ is $C_1$-$C_5$ alkyl. A $C_1$-$C_6$ acylamino group includes for example acetamide.

Particular embodiments of the present invention include the following groups of compounds of formula (I) wherein:
1. $R^1$ is —$CONR^{13}R^{14}$ and Z is independently selected from (xxi), (xxi), (xxiv) or (xxv);
2. Z is (xxi), T is —$CH_2$— and (m+s) is 1;
3. Z is (xxi), T is —O— and m is 1 and s is 1;
4. Z is (xxi), T is —S— and m is 1 and s is 1;
5. Z is (xxi), T is —CH=CH— and both m and s are 0;
6. Z is (xxi), T is —C(O)— and both m and s are 0;
7. $R^3$ to $R^8$ are each $C_{1-6}$ alkyl;
8. n is 1 or 2, preferably n is 2;
9. n is 1;
10. p is 1;
11. p is 2;
12. each of $R^{13}$ and $R^{14}$ is hydrogen; or
13. one of $R^9$, $R^{10}$, $R^{11}$ and $R^{12}$ is $C_{1-6}$ alkyl, preferably methyl or ethyl, and each of the remainder of $R^9$, $R^{10}$, $R^{11}$ or $R^{12}$ is hydrogen.

When n is 2 it will be appreciated that the values of $R^3$ and $R^4$ in the repeated units can be different.

In a particular embodiment of the present invention, $R^1$ is —$(CH_2)_t$—$R^{21}$.

In another particular embodiment of the present invention, Z is (xxi), (xxii), (xxiii), (xxiv) or (xxv).

In a further embodiment of the present invention, $R^1$ is —$(CH_2)_t$—$R^{21}$ and Z is (xxi), (xxii), (xxiii) or (xxv).

Any of the groups of compounds of formula (I) above may be combined with any other group or groups to define further particular embodiments of the present invention.

In a preferred embodiment, $R^1$ is $CONR^{13}R^{14}$ and Z is (xxi). In said embodiment:
when -T- is —O—, preferably m is 1 and s is 1;
when -T- is —S—, preferably m is 1 and s is 1;
when -T- is —$CH_2$—, (m+s) is preferably 1;
when -T- is —C(O)—, (m+s) is preferably 1; and
when -T- is —CH=CH—, (m+s) is preferably 0;

In another preferred embodiment, $R^1$ is —$(CH_2)_t$—$R^{21}$ and Z is any one of (xxi), (i)a and (xii)a, especially (xxi) or (i)a.

In a preferred group of compounds of formula (I) according to the present invention, $R^1$ is —$CONR^{13}R^{14}$. More preferably, $R^1$ is —$CONR^{13}R^{14}$ where $R^{13}$ and $R^{14}$ are each hydrogen or $C_{1-6}$ alkyl, especially hydrogen.

In another preferred group of compounds of formula (I) according to the present invention, $R^1$ is —$(CH_2)_t$—$R^{21}$. More preferably, $R^1$ is —$(CH_2)_t$—$R^{21}$ where t is O or 1. In the group —$(CH_2)_t$—$R^{21}$, —$R^{21}$ may be any of the values defined above and:

$R^{13}$ is preferably hydrogen or $C_1$-$C_6$ alkyl, especially hydrogen;

$R^{14}$ is preferably hydrogen or $C_1$-$C_6$ alkyl, especially hydrogen;

$R^{24}$ is preferably hydrogen or $C_1$-$C_6$ alkyl, especially hydrogen; or methyl;

$R^{22}$ is preferably hydrogen or $C_1$-$C_6$ alkyl, especially hydrogen; or methyl;

Preferred groups of compounds of formula (I) according to the present invention, where $R^1$ is —$(CH_2)_t$—$R^{21}$, include the following:

a) —$R^{21}$ is

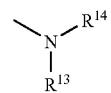

t is 1 and $R^{14}$ and $R^{13}$ are each hydrogen;

b) —$R^{21}$ is

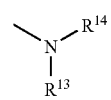

t is O and $R^{14}$ and $R^{13}$ are each hydrogen;

c) —$R^{21}$ is

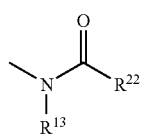

t is 1 and $R^{13}$ and $R^{22}$ are each hydrogen;

d) —$R^{21}$ is

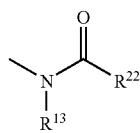

t is 1, $R^{13}$ is H and $R^{22}$ is methyl;

e) —R²¹ is
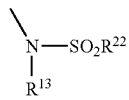
t is 1, R¹³ is H and R²² is methyl;
f) —R²¹ is
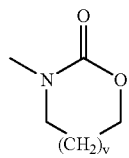
t is 1 and v is 0;
g) —R²¹ is
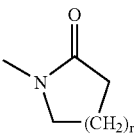
t is 1 and r is 1;
h) —R²¹ is
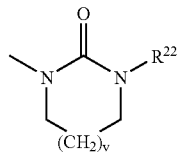
t is 0, R²² is H and v is 0;
i) —R²¹ is
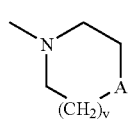
t is 0, v is 1 and A is S;
j) —R²¹ is
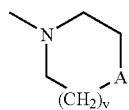
t is 0, v is 1 and A is O;
k) —R²¹ is
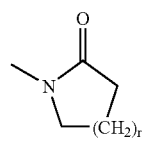
t is 0 and r is 1;
l) —R²¹ is
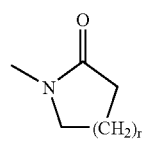
t is 0 and r is 0;
m) —R²¹ is
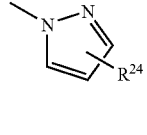
t is 0 and R²⁴ is H;
n) —R²¹ is
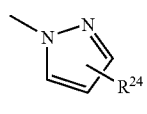
t is 1 and R²⁴ is H;
o) —R²¹ is
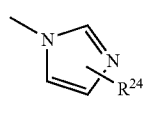
t is 1 and R²⁴ is H;
p) —R²¹ is
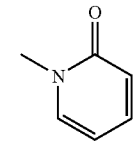
and t is 0;

q) —$R^{21}$ is

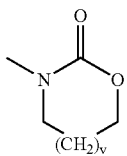

t is 0 and v is 0;
r) —$R^{21}$ is

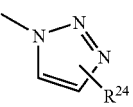

t is 0 and $R^{24}$ is H;
s) —$R^{21}$ is

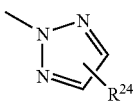

t is 0 and $R^{24}$ is H;
t) —$R^{21}$ is

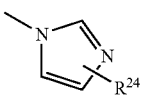

t is 0 and $R^{24}$ is H;
u) —$R^{21}$ is

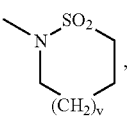

t is 0 and v is 0;
v) —$R^{21}$ is

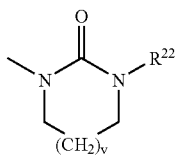

t is 0, v is 0 and $R^{22}$ is methyl;
w) —$R^{21}$ is

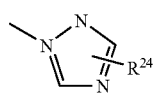

t is 0 and $R^{24}$ is hydrogen.

In the compounds of the present invention, $R^2$ is preferably hydrogen or $C_{1-6}$ alkyl, especially hydrogen.

Each of $R^3$, $R^4$, $R^5$, $R^6$, $R^7$ and $R^8$ is preferably hydrogen.

When one or each of $R^{11}$ and $R^{12}$ is $C_1$-$C_6$ alkyl or —$(CH_2)_q$—$OR^{20}$, $R^9$ and $R^{10}$ are both preferably hydrogen.

When one or each of $R^9$ and $R^{10}$ is $C_1$-$C_6$ alkyl or —$(CH_2)_q$—$OR^{20}$, $R^{11}$ and $R^{12}$ are both preferably hydrogen.

In a preferred embodiment, $R^9$, $R^{10}$, $R^{11}$ and $R^{12}$ are each hydrogen. In another preferred embodiment, one of $R^{11}$ and $R^{12}$ is methyl and the other is hydrogen, and $R^9$ and $R^{10}$ are both hydrogen.

In the compounds of the present invention, p is preferably 1 or 2.

In a preferred embodiment of the present invention,

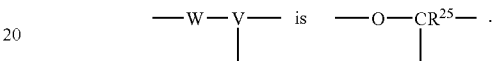

In said embodiment preferably $R^{25}$ is hydrogen.

In another preferred embodiment of the present invention, —X—Y— is

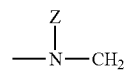

In another preferred embodiment, —X—Y— is

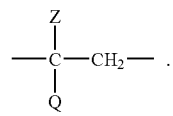

In said invention Q is preferably hydrogen and more preferably $R^9$, $R^{10}$, $R^{11}$ and $R^{12}$ are hydrogen.

In further preferred embodiments, Z is (xxi); Z is (xxii); Z is (xxiii); Z is (xxiv), Z is (xxv); Z is (i)a; Z is (xii)a. Especially preferred compounds are those in which Z is (xxi); Z is (i)a; Z is (xii)a. When Z is (i)$_a$, preferably one of $R^{15}$ and $R^{16}$ is —CN and the other is hydrogen. When Z is (xii)$_a$, preferably one of $R^{15}$ and $R^{16}$ is —F or —CN, and the other is hydrogen, and $R^{19}$ is hydrogen.

When Z is (xxi), preferably m+s is 1 or 2.

In a preferred embodiment of the present invention, $R^1$ is —$(CH_2)_t$—$R^{21}$ and Z is (xii)$_a$, wherein preferably one of $R^{15}$ and $R^{16}$ is —F or —CN and the other is hydrogen, and preferably $R^{19}$ is hydrogen.

In another preferred embodiment of the present invention, $R^1$ is —$(CH_2)_t$—$R^{21}$ and Z is (xxi), wherein -T- is preferably —$CH_2$— and (m+s) is preferably 1.

In yet another preferred embodiment of the present invention, $R^1$ is —$(CH_2)_t$—$R^{21}$ and Z is (i)a, wherein preferably one of $R^{15}$ and $R^{16}$ is —CN, and the other is hydrogen.

Any of the preferred groups herein may be combined with any other preferred group or groups to define further preferred compounds.

Preferred compounds of formula (I) of the present invention include compounds of formulae:

(a)

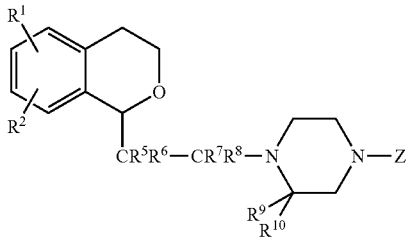

(I")

wherein $R^1$, $R^2$, $R^5$ to $R^{10}$ and Z have the values defined for formula I above, with the provisos for formula I; Particularly preferred compounds of formula (I") include groups of compounds wherein $R^5$ to $R^8$ are hydrogen; or wherein $R^2$ is hydrogen; or wherein $R^1$ is —$CONR^{13}R^{14}$, wherein preferably $R^{13}$ and $R^{14}$ are hydrogen; or wherein Z is (xxi) wherein preferably -T- is —$CH_2$— and (m+s) is 1; or wherein one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen. Particularly preferred compounds of the invention include compounds of formula (I") above wherein $R^5$ to $R^8$ are hydrogen, $R^2$ is hydrogen, $R^1$ is —$CONR^{13}R^{14}$, wherein preferably $R^{13}$ and $R^{14}$ are hydrogen, Z is (xxi), wherein preferably -T- is —$CH_2$— and (m+s) is 1 and one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen;

(b)

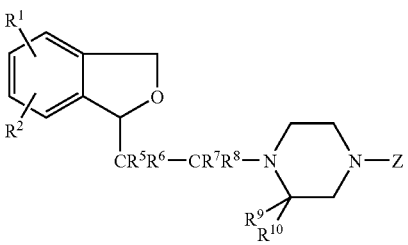

(I''')

wherein $R^1$, $R^2$, $R^5$ to $R^{10}$ and Z have the values defined for formula I above, with the provisos for formula I; Particularly preferred compounds of formula (I''') include groups of compounds wherein $R^5$ to $R^8$ are hydrogen; or wherein $R^2$ is hydrogen; or wherein $R^1$ is —$CONR^{13}R^{14}$, wherein preferably $R^{13}$ and $R^{14}$ are hydrogen; or wherein Z is (xxi) wherein preferably -T- is —$CH_2$— and (m+s) is 1; or wherein one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen. Particularly preferred compounds of the invention include compounds of formula (I''') above wherein $R^5$ to $R^8$ are hydrogen, $R^2$ is hydrogen, $R^1$ is —$CONR^{13}R^{14}$, wherein preferably $R^{13}$ and $R^{14}$ are hydrogen, Z is (xxi), wherein preferably -T- is —$CH_2$— and (m+s) is 1 and one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen; and (c)

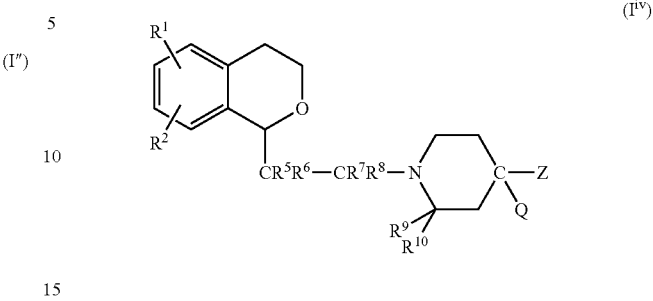

(I^{iv})

wherein $R^1$, $R^2$, $R^5$ to $R^{10}$, Q and Z have the values defined for formula I above, with the provisos for formula I; Particularly preferred compounds of formula (I^{iv}) include groups of compounds wherein $R^5$ to $R^8$ are hydrogen; or wherein $R^2$ is hydrogen; or wherein Q is hydrogen; or wherein one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen. Particularly preferred compounds of the invention include compounds of formula (I^{iv}) above wherein $R^5$ to $R^8$ are hydrogen, $R^2$ is hydrogen, Q is hydrogen and one of $R^9$, $R^{10}$, $R^{11}$ and $R^{12}$ is $C_{1-6}$ alkyl, preferably methyl or ethyl and each of the remainder $R^9$, $R^{10}$, $R^{11}$ and $R^{12}$ is hydrogen.

Particularly preferred compounds of the present invention of formula (I'):

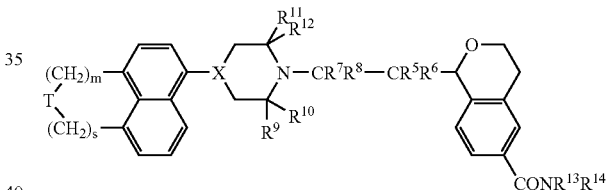

wherein

Each of $R^{13}$ and $R^{14}$ is H or $C_1$-$C_6$ alkyl, preferably hydrogen;

Each of $R^5$, $R^6$, $R^7$ and $R^8$ is H or $C_1$-$C_6$ alkyl, preferably hydrogen;

One or both of $R^{11}$ and $R^{12}$ is $C_1$-$C_6$ alkyl, preferably methyl or ethyl and especially methyl; preferably one of $R^{11}$ and $R^{12}$ is $C_1$-$C_6$ alkyl, preferably methyl or ethyl and especially methyl and the other is hydrogen;

Each of $R^9$ and $R^{10}$ is hydrogen, $C_1$-$C_6$ alkyl, preferably methyl or hydrogen and especially hydrogen. —X— is —CH— or —N—, especially —N—;

T is —$CH_2$—, —O—, —S—, —C(O)— or —CH=CH—, especially —$CH_2$— provided that when T is —$CH_2$—, —O—, —S— or —C(O)—, m+s is 1 or 2, and each of m and s is 0 or 1; and when T is —$CH_2$—, m+s is especially 1.

Particularly preferred embodiment of the invention includes compounds of formula (I) selected from:

(1S)-1-{2-[(2R)-4-(1,2-Dihydro-5-acenaphthylenyl)-2-methylpiperazinyl]ethyl}-3,4-dihydro-1H-2-benzopyran-6-carboxamide, (1S)-1-{2-[(2R)-4-(1,2-Dihydro-5-acenaphthylenyl)-2-ethylpiperazinyl]ethyl}-3,4-dihydro-1H-2-benzopyran-6-carboxamide, (1S)-1-{2-[(2S)-4-(1,2-Dihydro-5-acenaphthylenyl)-2-ethylpiperazinyl]ethyl}-3,4-dihydro-1H-2-benzopyran-6-carboxamide, (1S)-1-{2-[4-(1,2-Dihydro-5-acenaphthylenyl)hexahydro-1H-1,4-diazepin-1-yl]ethyl}-3,4-dihydro-1H-2-benzopyran-6-carboxamide, (1S)-1-{2-[(2R)-4-(5-Acenaphthylenyl)-2-methylpiperazinyl]ethyl}-3,4-dihydro-1H-2-benzopyran-6-carboxamide, (1S)-1-{2-[(2R)-2-Methyl-4-(1H,3H-naphtho[1,8-cd]pyran-6-yl)piperazinyl]ethyl}-3,4-dihydro-1H-2-benzopyran-6-carboxamide, (1S)-1-{2-[(2R)-2-Methyl-4-(1H,3H-naphtho[1,8-cd]thiopyran-6-yl)piperazinyl]ethyl}-3,4-dihydro-1H-2-benzopyran-6-carboxamide, (1S)-1-{2-[4-(1,2-Dihydro-5-acenaphthylenyl)-1-piperidinyl]ethyl}-3,4-dihydro-1H-2-benzopyran-6-carboxamide, (1S)-1-{2-[(2R)-4-(1,2-Dihydro-5-acenaphthylenyl)-2-methylpiperazinyl]ethyl}-1,3-dihydro-2-benzofuran-5-carboxamide, (1S)-1-{2-[(2R)-4-(1,2-Dihydro-5-acenaphthylenyl)-2-methylpiperazinyl]ethyl}-1,3-dihydro-2-benzofuran-5-carboxamide, 1-{2-[4-(1,2-Dihydro-5-acenaphthylenyl)hexahydro-1H-1,4-diazepin-1-yl]ethyl}-1,3-dihydro-2-benzofuran-5-carboxamide, 1-({2-[(2R)-4-(6-Fluoro-1-naphthyl)-2-methylpiperazinyl]ethyl}-3,4-dihydro-1H-2-benzopyran-6-yl)methanamine, 1-({2-[(2R)-4-(6-Fluoro-1-naphthyl)-2-methyl-piperazinyl]ethyl}-3,4-dihydro-1H-2-benzopyran-6-yl)methylformamide, N-[((1S)-1-{2-[(2R)-4-(6-Fluoro-1-naphthyl)-2-methylpiperazinyl]ethyl}-3,4-dihydro-1H-2-benzopyran-6-yl)methyl]acetamide, N-[((1S)-1-{2-[(2R)-4-(6-Fluoro-1-naphthyl)-2-methylpiperazinyl]ethyl}-3,4-dihydro-1H-2-benzopyran-6-yl)methyl]methanesulfonamide, 5-[(3R)-3-Methyl-4-(2-{(1S)-6-[(2-oxo-1,3-oxazolidin-3-yl)methyl]-3,4-dihydro-1H-2-benzopyran-1-yl}ethyl)piperazinyl]-2-naphthonitrile, 3-[((1S)-1-{2-[(2R)-4-(1,2-Dihydro-5-acenaphthylenyl)-2-methylpiperazinyl]ethyl}-3,4-dihydro-1H-2-benzopyran-6-yl)methyl]-1,3-oxazolidin-2-one, 3-[(3R)-3-Methyl-4-(2-{(1S)-6-[(2-oxo-1,3-oxazolidin-3-yl)methyl]-3,4-dihydro-1H-2-benzopyran-1-yl}ethyl)-piperazinyl]-1-benzothiophene-6-carbonitrile, 1-[((1S)-1-{2-[(2R)-4-(1,2-Dihydro-5-acenaphthylenyl)-2-methylpiperazinyl]ethyl}-3,4-dihydro-1H-2-benzopyran-6-yl)methyl]-2-pyrrolidinone, 3-[(3R)-3-Methyl-4-(2-{(1S)-6-[(2-oxo-1-pyrrolidinyl)methyl]-3,4-dihydro-1H-2-benzopyran-1-yl}ethyl)piperazinyl]-1-benzothiophene-6-carbonitrile, (2R)-4-(1,2-Dihydro-5-acenaphthylenyl)-1-{2-[(1S)-6-(1H-imidazol-1-ylmethyl)-3,4-dihydro-1H-2-benzopyran-1-yl]ethyl}-2-methylpiperazine, 3-((3R)-4-{2-[(1S)-6-(1H-Imidazol-1-ylmethyl)-3,4-dihydro-1H-2-benzopyran-1-yl]ethyl}-3-methyl-piperazinyl)-1-benzothiophene-6-carbonitrile, 3-((3R)-3-Methyl-4-{2-[(1S)-6-(1H-pyrazol-1-ylmethyl)-3,4-dihydro-1H-2-benzopyran-1-yl]ethyl}piperazinyl)-1-benzothiophene-6-carbonitrile, (1S)-1-{2-[(2R)-4-(6-Fluoro-1-naphthyl)-2-methylpiperazinyl]ethyl}-3,4-dihydro-1H-2-benzopyran-6-amine, 3-((1S)-1-{2-[(2R)-4-(6-Cyano-1-naphthyl)-2-methylpiperazinyl]ethyl}-3,4-dihydro-1H-2-benzopyran-6-yl)-1,3-oxazolidin-2-one, 3-((1S)-1-{2-[(2R)-4-(1,2-dihydro-5-acenaphthylenyl)-2-methylpiperazinyl]ethyl}-3,4-dihydro-1H-2-benzopyran-6-yl)-1,3-oxazolidin-2-one, 3-((1S)-1-{2-[(2R)-4-(6-Cyano-1-benzothien-3-yl)-2-methylpiperazinyl]ethyl}-3,4-dihydro-1H-2-benzopyran-6-yl)-1,3-oxazolidin-2-one, 1-((1S)-1-{2-[(2R)-4-(6-fluoro-1-naphthyl)-2-methylpiperazinyl]ethyl}-3,4-dihydro-1H-2-benzopyran-6-yl)-2-pyrrolidinone, 1-((1S)-1-{2-[(2R)-4-(6-Cyano-1-naphthyl)-2-methylpiperazinyl]ethyl}-3,4-dihydro-1H-2-benzopyran-6-yl)-2-pyrrolidinone, 1-((1S)-1-{2-[(2R)-4-(6-cyano-1-benzothien-3-yl)-2-methylpiperazinyl]ethyl}-3,4-dihydro-1H-2-benzopyran-6-yl)-2-pyrrolidinone, 1-((1S)-1-{2-[(2R)-4-(6-fluoro-1-naphthyl)-2-methylpiperazinyl]ethyl}-3,4-dihydro-1H-2-benzopyran-6-yl)-2-azetidinone, 1-((1S)-1-{2-[(2R)-4-(6-cyano-1-naphthyl)-2-methylpiperazinyl]ethyl}-3,4-dihydro-1H-2-benzopyran-6-yl)-2-azetidinone, (2R)-4-(1,2-Dihydro-5-acenaphthylenyl)-1-{2-[(1S)-6-(1,1-dioxido-2-isothiazolidinyl)-3,4-dihydro-1H-2-benzopyran-1-yl]ethyl}-2-methylpiperazine, 1-((1S)-1-{2-[(2R)-4-(6-Cyano-1-benzothien-3-yl)-2-methylpiperazinyl]ethyl}-3,4-dihydro-1H-2-benzopyran-6-yl)-2-imidazolidinone, 1-((1S)-1-{2-[(2R)-4-(6-Fluoro-1-naphthyl)-2-methylpiperazinyl]ethyl}-3,4-dihydro-1H-2-benzopyran-6-yl)-2-imidazolidinone, 1-((1S)-1-{2-[(2R)-4-(6-Cyano-1-benzothien-3-yl)-2-methylpiperazinyl]ethyl}-3,4-dihydro-1H-2-benzopyran-6-yl)-3-methyl-2-imidazolidinone, 3-((3R)-3-Methyl-4-{2-[(1S)-6-(4-thiomorpholinyl)-3,4-dihydro-1H-2-benzopyran-1-yl]ethyl}piperazinyl)-1-benzothiophene-6-carbonitrile, 3-((3R)-3-Methyl-4-{2-[(1S)-6-(4-morpholinyl)-3,4-dihydro-1H-2-benzopyran-1-yl]ethyl}piperazinyl)-1-benzothiophene-6-carbonitrile, (2R)-4-(1,2-Dihydro-5-acenaphthylenyl)-2-methyl-1-{2-[(1S)-6-(1H-pyrazol-1-yl)-3,4-dihydro-1H-2-benzopyran-1-yl]ethyl}piperazine, 3-((3R)-3-Methyl-4-{2-[(1S)-6-(1H-pyrazol-1-yl)-3,4-dihydro-1H-2-benzopyran-1-yl]ethyl}piperazinyl)-1-benzothiophene-6-carbonitrile, (2R)-4-(1,2-Dihydro-5-acenaphthylenyl)-1-{2-[(1S)-6-(1H-imidazol-1-yl)-3,4-dihydro-1H-2-benzopyran-1-yl]ethyl}-2-methylpiperazine, 3-((3R)-4-{2-[(1S)-6-(1H-Imidazol-1-yl)-3,4-dihydro-1H-2-benzopyran-1-yl]ethyl}-3-methylpiperazinyl)-1-benzothiophene-6-carbonitrile, (2R)-4-(1,2-Dihydro-5-acenaphthylenyl)-2-methyl-1-{2-[(1S)-6-(2H-1,2,3-triazol-2-yl)-3,4-dihydro-1H-2-benzopyran-1-yl]ethyl}piperazine, (2R)-4-(1,2-Dihydro-5-acenaphthylenyl)-2-methyl-1-{2-[(1S)-6-(1H-1,2,3-triazol-1-yl)-3,4-dihydro-1H-2-benzopyran-1-yl]ethyl}piperazine, 3-((3R)-3-Methyl-4-{2-[(1S)-6-(2H-1,2,3-triazol-2-yl)-3,4-dihydro-1H-2-benzopyran-1-yl]ethyl}piperazinyl)-1-benzothiophene-6-carbonitrile, 3-((3R)-3-Methyl-4-{2-[(1S)-6-(1H-1,2,3-triazol-1-yl)-3,4-dihydro-1H-2-benzopyran-1-yl]ethyl}piperazinyl)-1-benzothiophene-6-carbonitrile, (2R)-4-(1,2-Dihydro-5-acenaphthylenyl)-2-methyl-1-{2-[(1S)-6-(1H-1,2,4-triazol-1-yl)-3,4-dihydro-1H-2-benzopyran-1-yl]ethyl}piperazine, 3-((3R)-3-Methyl-4-{2-[(1S)-6-(1H-1,2,4-triazol-1-yl)-3,4-dihydro-1H-2-benzopyran-1-yl]ethyl}piperazinyl)-1-benzothiophene-6-carbonitrile, 1-((1S)-1-{2-[(2R)-4-(1,2-Dihydro-5-acenaphthylenyl)-2-methylpiperazinyl]ethyl}-3,4-dihydro-1H-2-benzopyran-6-yl)-2(1H)-pyridinone, and 3-((3R)-3-Methyl-4-{2-[(1S)-6-(2-oxo-1(2H)-pyridinyl)-3,4-dihydro-1H-2-benzopyran-1-yl]ethyl}piperazinyl)-1-benzothiophene-6-carbonitrile and pharmaceutically acceptable salts thereof.

An especially preferred compound of formula (I) is (1S)-1-{2-[(2R)-4-(1,2-Dihydro-5-acenaphthylenyl)-2-methylpiperazinyl]ethyl}-3,4-dihydro-1H-2-benzopyran-6-carboxamide and pharmaceutically acceptable salts thereof.

As indicated above, it is, of course, possible to prepare salts of the compounds of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, hydroxymaleic, fumaric, malic, tartaric, citric, salicyclic, o-acetoxybenzoic, or organic sulphonic, 2-hydroxyethane sulphonic, toluene-p-sulphonic, naphthalene-2-sulphonic or bisethane sulphonic acids. The fumarate is a most preferred salt.

In addition to the pharmaceutically acceptable salts, other salts are included in the invention. They may serve as intermediates in the purification of compounds or in the preparation of compounds or in the preparation of other, for example pharmaceutically acceptable acid addition salts, or are useful for identification, characterisation or purification.

It will be appreciated that the compounds of the invention can contain one or more asymmetric carbon atoms which gives rise to isomers. The compounds are normally prepared as racemic mixtures, but individual isomers can be isolated by conventional techniques if so desired. Such racemic mixtures and individual optical isomers form part of the present invention, the compounds being employed as racemates or in enantiomerically pure form.

Preferred compounds of the invention are those of formula:

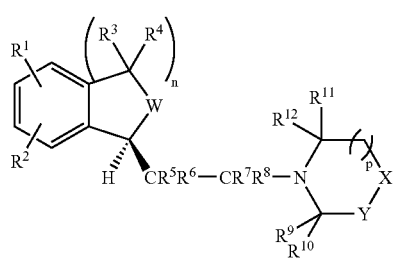
(Ia)

wherein

—X—Y—, $R^1$ to $R^{12}$, n and p have the values defined for formula I above, and —W— is —CH$_2$—, —O—, or —S—, with the proviso's as for formula I above.

Compounds of formula Ia can contain more asymmetric carbons. For example when the $R^{11}$ and $R^{12}$ groups are different, this gives rise to further isomers, such as compounds of formula (Ib) and (Ic):

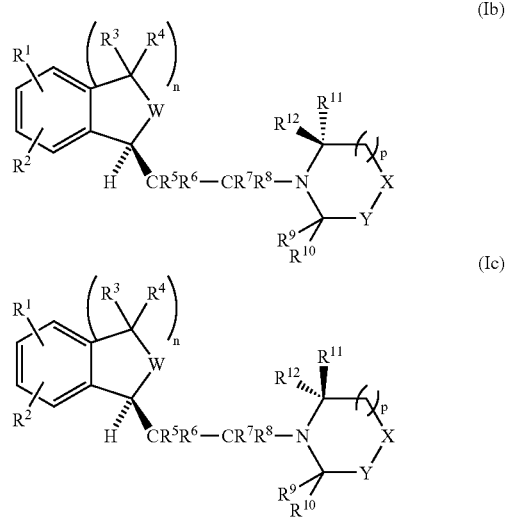
(Ib)

(Ic)

wherein all of the values —X—Y—, $R^1$ to $R^{12}$, n and p are as defined in formula (I) above, and —W— is —CH$_2$—, —O— or —S—, with the proviso's therein. Said isomers are also an aspect of the present invention.

Compounds of formula (Ib) above, wherein the group $R^{11}$ takes priority over $R^{12}$ according to the Cahn-Ingold-Prelog sequence rules as described in J. March, Fourth Edition, Chapter 4, page 109, and wherein therefore the configuration of the carbon to which $R^{11}$ and $R^{12}$ are attached is R, are preferred. Particularly preferred compounds are those of formula (Ib) wherein $R^9$, $R^{10}$ and $R^{12}$ are hydrogen and $R^{11}$ is $C_{1-6}$ alkyl.

In the same way, when the $R^9$ and $R^{10}$ groups are different in compounds of formula Ia, this also gives rise to isomers, such as compounds of formula (Id) and (Ie):

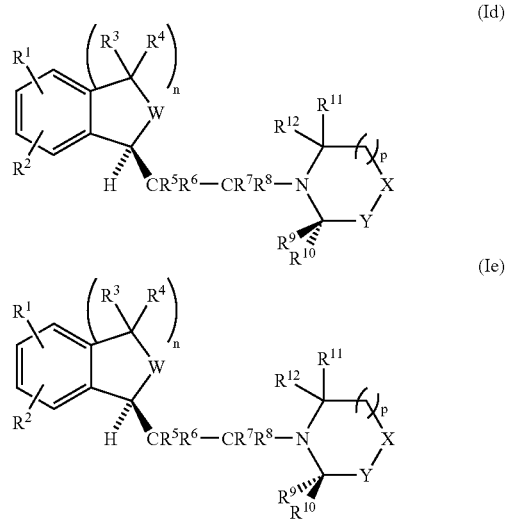
(Id)

(Ie)

wherein all of the values —X—Y—, $R^1$ to $R^{12}$, n and p have the values defined for formula I above, and —W— is —CH$_2$—, —O—, or —S— with the proviso's as for formula I. Said isomers are also an aspect of the invention.

Compounds of formula (Id) above, wherein the group $R^9$ takes priority over $R^{10}$ according to the Cahn-Ingold-Prelog sequence rules as described in J. March, Fourth Edition, Chapter 4, page 109, and wherein therefore the configuration of the carbon to which $R^9$ and $R^{10}$ are attached is R, are preferred. Particularly preferred compounds are those of formula (Id) wherein $R^9$ is $C_{1-6}$ alkyl and $R^{10}$, $R^{11}$ and $R^{12}$ are hydrogen.

The preferred stereochemistry detailed above applies also the compounds of the present invention of formulae (I'), (I''), (I''') and (I'').

The compounds of the invention can be produced by reacting a compound having the formula:

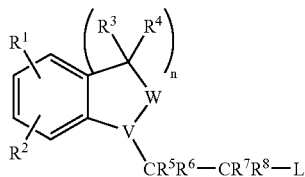

(III)

where L is a leaving group, with a compound of the formula:

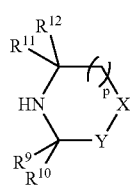

(IV)

where the substituents have the values defined for formula (I) above.

The reaction is preferably carried out in the presence of a base such as potassium carbonate, in an organic solvent such as a polar aprotic solvent, for example, acetonitrile, at a temperature of from 20° C. to 100° C. Examples of suitable leaving groups are mesylate, tosylate, triflate, chloride, bromide and iodide, especially bromide and iodide.

Intermediate compounds of formula (III) can, for example, be prepared from the corresponding alcohols of the formula:

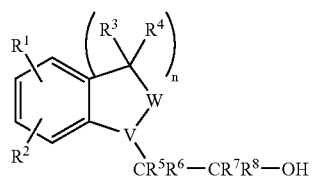

(V)

using standard methods known in the literature such as the ones shown in March, Advanced Organic Chemistry, Fourth Edition, for example the methods mentioned on pages 353 and 354.

Compounds of formula (IV) can be prepared by a variety of methods well known in the art. Substituted 3-(1,2,3,6-tetrahydro-4-pyridinyl)-1H-indoles, fluoro substituted-3-(4-piperidinyl)-1H-indoles and (3R)-6-fluoro-3-(3-pyrrolidinyl)-1H-indole may be prepared using methods described in European patent application EP-A 0897921 and WO patent applications WO 99/58525 and WO 00/02341. Substituted and unsubstituted 4-(1-naphthyl)-1,2,3,6-tetrahydropyridines and 4-(1-naphthyl)piperidines may be prepared using methods described in U.S. Pat. Nos. 5,472,966, 5,250,544, and 5,292,711. Substituted and unsubstituted 1-(1-naphthyl)piperazines may be prepared using methods described in U.S. Pat. No. 5,166,156. (2R,4S)-2-methyl-4-(2-naphthyl)piperidine was prepared using methods referred to in Med. Chem. Res. (1997), 7(4), 207-218. Substituted and unsubstituted 4-(1-benzopyran-3-yl)-1,2,3,6-tetrahydropyridines and 4-(1-benzopyran-3-yl)piperidines may be prepared using methods described in EP-A 0466585 or in Japanese patent JP 2000086603. 6-fluoro-3-(1,2,3,6-tetrahydro-4-pyridinyl)-1,2-benzisoxazole may be prepared by methods based on U.S. Pat. No. 3,678,062. Substituted and unsubstituted 6-fluoro-1-3-(1,2,3,6-tetrahydro-4-pyridinyl)-1H-indazoles may be prepared by methods described in EP-A 0135781. 4-(Thieno[3,2-b]pyrrol-6-yl)-1,2,3,6-tetrahydropyridine may be prepared by methods found in Heterocycl. Commun. (1999), 5(4) 305-310. Substituted and unsubstituted 4-(1-benzothieny-7-yl)-1,2,3,6-tetrahydropyridines and 4-(4-fluoro-1-benzopyran-7-yl)-1,2,3,6-tetrahydro-pyridine may be prepared using methods described in WO 00/00198. 6-Substituted 2-[3,4-dihydro-1H-2-benzopyran-1-yl]ethyl methanesulfonates may be made by procedures described in WO 95/18118. 5-Methoxy-3-(1,2,3,6-tetrahydro-4-pyridinyl)-1H-indole may be obtained from Tocris Cookson. 3-[2-(4-piperidinyl)ethyl]-1H-indoles may be prepared using methods described in J. Med. Chem. 1993, 36(15), 2242 and J. Med. Chem, 36(9) 1194.

Compounds of formula (IV) wherein $R^{10}$ is —CH$_2$—OR$^{20}$ and X—Y— is

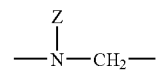

can be prepared as described in the synthetic scheme below:

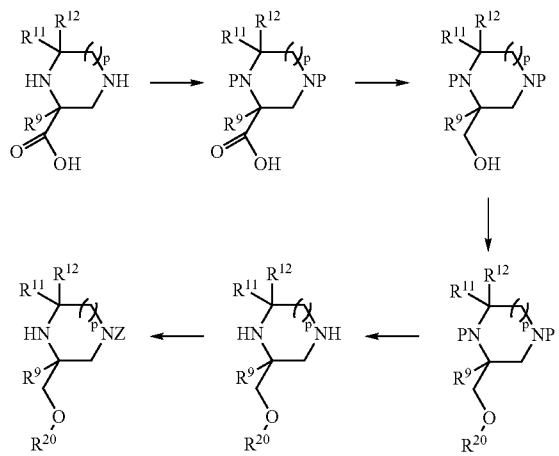

In the above scheme, the nitrogen atoms are protected with a suitable protecting group such as N-tert-butoxycarbonyl (BOC) or any other suitable group using methods described in Greene and Wuts, Protecting Groups in Organic Synthesis, 3rd. Ed., John Wiley & Sons, followed by reduction of the acid moiety to the alcohol, alkylation of said alcohol and deprotection of the nitrogen atoms.

The unprotected piperidine is then reacted with a compound of formula Z-L$^{iii}$ in the presence of a palladium catalyst such as palladium acetate, BINAP ((R)-2,2'-bis(diphenylphosphino)-1,1'-binaphthyl) and a base such as Caesium carbonate.

The nitrogen groups can for example be protected with a BOC group using di-tert-butyl dicarbonate in the presence of a base such as sodium hydroxide in an organic solvent such as ethanol.

The reduction is preferably carried out in the presence of a reducing agent such as borane dimethyl sulfide in a organic solvent such as THF at a temperature ranging from 0° C. to room temperature.

The alkylation reaction is preferably carried out in an organic solvent such as DMF, in the presence of a base such as sodium hydride and an alkylating agent such as iodomethane (for compounds where $R^{20}$ is methyl).

Compounds of formula (V) wherein $R^7$ and $R^8$ are hydrogen can, for example, be prepared from the appropriate esters of the formula:

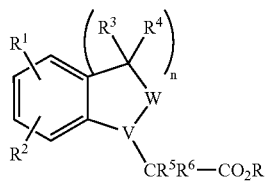
(VI)

where R is $C_{1-6}$ alkyl. Such esters can be reduced in the presence of a reducing agent such as lithium borohydride or lithium aluminium hydride in a suitable organic solvent such as tetrahydrofuran (THF).

Compounds of formula (V) wherein $R^1$ is —$CONR^{13}R^{14}$ can be prepared from the appropriate halo-substituted alcohols of the formula:

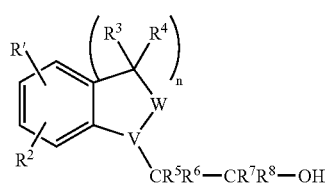
(V)$^i$ where R' is a halo group, such as chloro, bromo or iodo. Such alcohols are prepared using the same conditions as shown above. Then the alcohol is protected using a suitable protecting group as shown in Greene and Wuts, Protecting Groups in Organic Synthesis, 3rd. Ed., John Wiley & Sons. Preferred protecting groups are silyloxy protecting groups such as for example tertbutyldimethylsilyl group.

The halogen is then converted to the corresponding carboxamido group (—$CONR^{13}R^{14}$), via formation of the corresponding carboxy group and then condensation with the appropriate amine of formula $HNR^{13}R^{14}$. The carboxy group is formed by reaction of the intermediate organolithium reagent with carbon dioxide in a suitable organic solvent such as THF. The subsequent condensation reaction with the appropriate amine of formula $HNR^{13}R^{14}$ is preferably carried out in the presence of a coupling reagent such as carbonyldiimidazole (CDI) in a suitable solvent such as dioxan.

Similarly the halogen can be converted in one step to the corresponding carboxamido group by reaction of the organolithium reagent described above with trimethylsilyl isocyanate.

Alternatively the halogen can be converted to the corresponding carboxamido group by initial reaction with an inorganic cyanide, such as zinc cyanide, in the presence of a palladium catalyst, such as tris(dibenzylideneacetone)dipalladium, and a phosphine ligand, such as tri-tert-butylphosphine. The reaction is carried out in a suitable solvent such as dioxan, usually at reflux. The resultant nitrile is then hydrolysed to the carboxamide under basic conditions, such as hydrogen peroxide with potassium carbonate. The reaction is carried out in a suitable solvent such as DMSO in methanol. In this conversion there is no necessity to protect the alcohol function.

Then the alcohols are deprotected using standard methods known in the literature, such as Greene and Wuts, Protecting Groups in Organic Synthesis, 3rd. Ed., John Wiley & Sons.

Compounds of the formula (VI) wherein

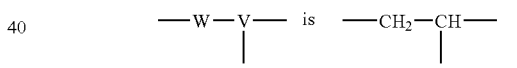

and $R^5$ and $R^6$ are hydrogen can be prepared from the appropriate ketones of formula (VII) as shown in Scheme 1 below.

Scheme 1

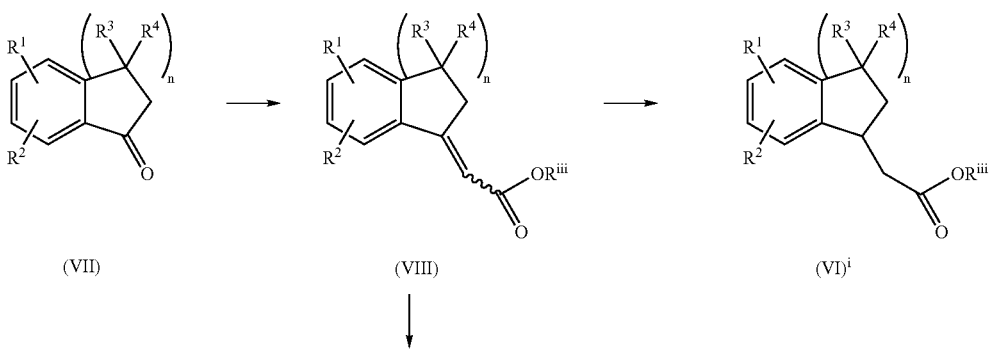

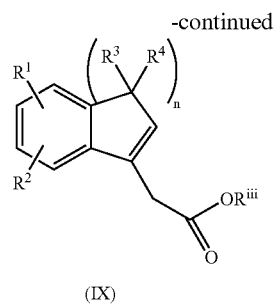

(IX)

Such ketones react with activated ylides such as for example a phosphonate of the formula $(R^{ii}O)_2P(O)CH_2CO_2R^{iii}$, wherein $R^{ii}$ and $R^{iii}$ are each $C_{1-6}$ alkyl, in the presence of a base such as sodium hydride in a suitable solvent such as for example THF to form the corresponding unsaturated ester (VIII). The alkene is reduced for example via hydrogenation in the presence of a catalyst such as Pd on charcoal in a suitable solvent such as ethanol or methanol.

Unsaturated esters of formula (IX) can be prepared via isomerisation of the corresponding unsaturated ester of formula (VIII) as shown in scheme 1 above. This reaction is carried out in the presence of a suitable base such as sodium methanide in a suitable solvent such as THF.

Compounds of the formula (VI) wherein

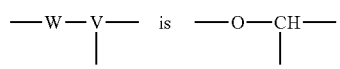

can be prepared as shown in scheme 2 from the appropriate lactones of formula (X).

Such lactones are converted to the corresponding hemiacetals via reduction of the lactone using a reducing agent such as diisobutylaluminium hydride (DIBAL) in the presence of a suitable solvent such as dichloromethane, followed by the protection of the intermediate hemiacetal with a suitable protecting group such as acetate. The protected hemiacetal is reacted with an appropriate organozincate derived from the corresponding haloacetal of formula $L^i\text{-}CH_2\text{—}CO_2R$ wherein $L^i$ is a halogen group such as bromo or iodo and R has the value defined above, in the presence of a Lewis acid such as trimethylsilyltriflate to form esters of the formula $(VI)^{ii}$.

Alternatively the hemiacetal is reacted directly with an activated ylid such as for example a phosphonate of the formula $(R^{ii}O)_2P(O)CH_2CO_2R^{iii}$, wherein $R^{ii}$ and $R^{iii}$ are each $C_{1-6}$ alkyl, in the presence of a base such as caesium carbonate in a suitable solvent such as for example THF, to form the corresponding ester $(VI)^{ii}$. Such esters can be converted to the corresponding alcohols using the method mentioned above. Alternatively they can be hydrolysed in acidic conditions to the acid, followed by formation of the mixed anhydride and final reduction of such a mixed anhydride to the corresponding alcohol of formula $(V)^{ii}$.

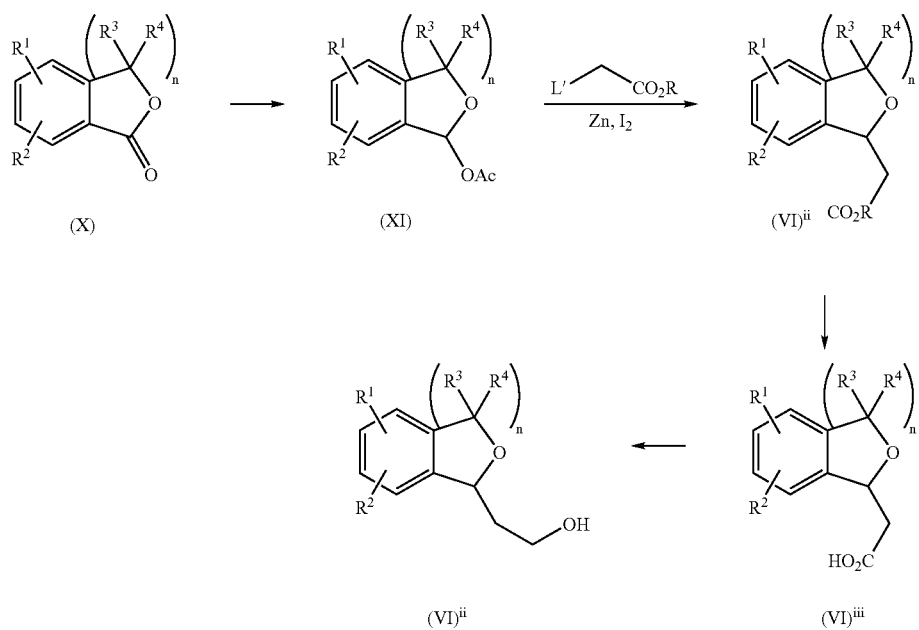

Alternatively compounds above wherein n is 2 can be synthesised via standard acid catalysed cyclisation of the corresponding phenyl alcohol of formula (XII) with an appropriate aldehyde of the formula CHO—CH$_2$—COOR$^{iv}$ or its corresponding acetal of the formula (R$^v$O)$_2$CH—CH$_2$—COOR$^{iv}$, wherein R$^{iv}$ and R$^v$ are each independently a C$_1$-C$_6$ alkyl group, in the presence of a Lewis acid such as titanium tetrachloride in a suitable solvent such as dichloromethane, see Scheme 3 below.

Scheme 3

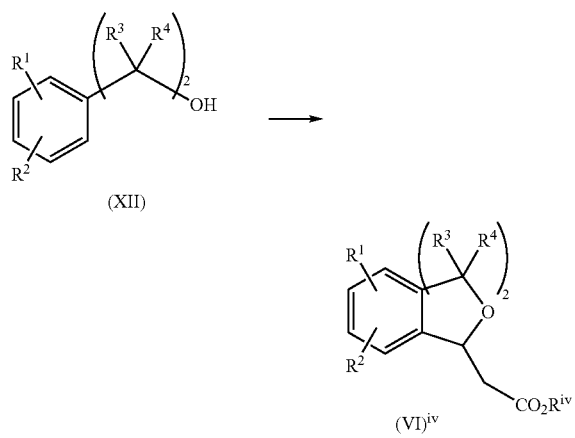

Compounds of the formula (V) wherein

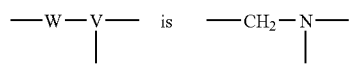

can be prepared as shown in scheme 4 from the appropriate quinolines of formula (XIII).

Such quinolines are converted to the corresponding 1,2,3,4 tetrahydroquinolines by reduction, for example by hydrogenation in the presence of ammonium formate and a suitable catalyst such as Palladium on charcoal in a suitable solvent such as methanol. The tetrahydroquinoline is then alkylated with allyl halide for example allyl bromide in the presence of a suitable base such as sodium hydride in a suitable solvent such as dimethylformamide (DMF). The double bond of the allyl group is then cleaved for example via ozonolysis. The intermediate ozonide formed is reduced with a suitable reducing agent such as sodium borohydride to give the corresponding alcohol. Alternatively such a double bond can be cleaved for example with osmium tetroxide and sodium periodate in the presence of a suitable reducing agent such as sodium borohydride.

Compounds of the formula (V) wherein

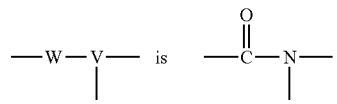

can be prepared as shown in scheme 5 from the appropriate 2-oxo-1,2,3,4-tetrahydroquinoline of formula (XVI).

Scheme 5

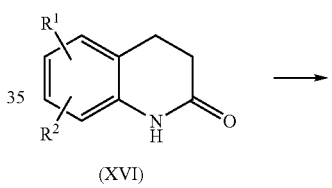

Scheme 4

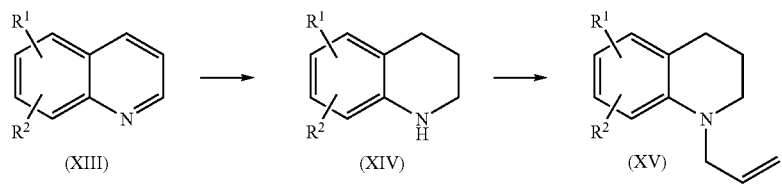

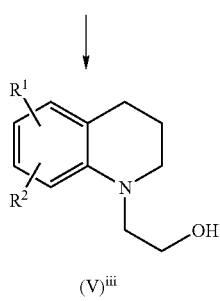

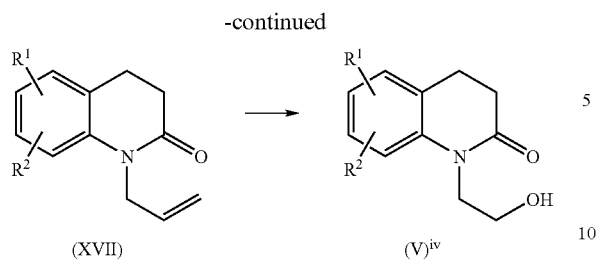

(XVII) → (V)$^{iv}$

Such 2-oxo-1,2,3,4-tetrahydroquinolines can be alkylated with an allyl halide for example allyl bromide in the presence of a suitable base such as sodium hydride in a suitable solvent such as dimethylformamide (DMF). The allyl group can be converted to the corresponding alcohol using the method shown above.

Compounds of the invention can also be synthesised via reaction of the corresponding amine of the formula (XIX) with a compound of the formula Z-L$^{iii}$ wherein L$^{iii}$ is a leaving group such as triflate or a halide such as bromide or iodide.

Scheme 6

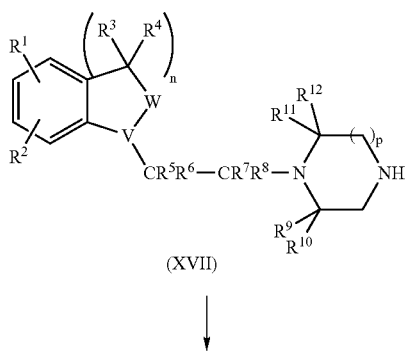

(XVII)

↓

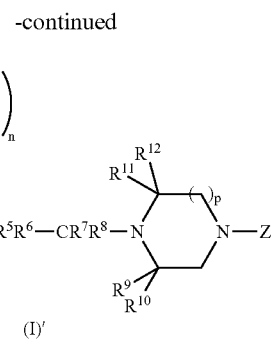

(I)′

Such reactions are usually carried out in the presence of a palladium catalyst such as palladium acetate and a base such as potassium tertbutoxide.

Some intermediates of the general formula Z-L$^{iii}$ wherein L$^{iii}$ is a halogen group such as bromo are commercially available. Alternatively, they can be synthesised from known literature routes, such as by brominating the corresponding aromatic group with NBS. Intermediates wherein L$^{iii}$ is a triflate can be prepared using methods known in the art such as from the corresponding ketones in the presence of triflic anhydride. Such intermediates are illustrated in scheme 7 for compound wherein Z is (i) and (xii), but it will be appreciated that such method can be used for any values of Z. It will also be appreciated that for compounds wherein Z is (xxi) to (xxv) the linker -T- might have to be protected during any of these processes, especially for compounds wherein -T- is —C(O)— or —CH=CH—.

Scheme 7

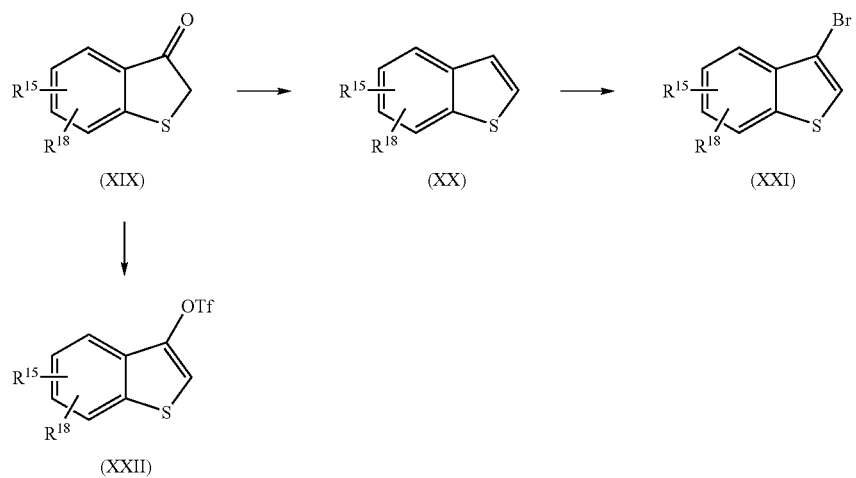

(XIX) → (XX) → (XXI)

↓

(XXII)

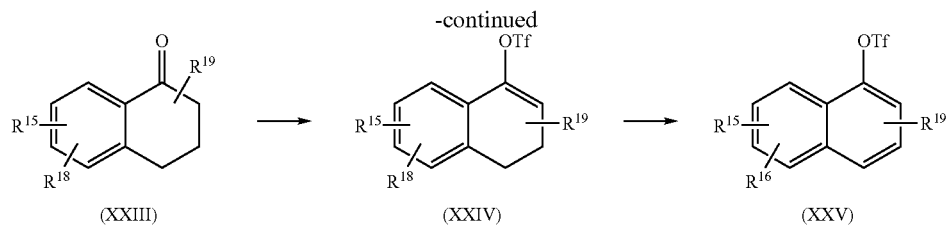

Compounds of formula (I) wherein $R^1$ is

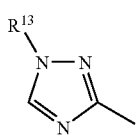

can be synthesised from the corresponding amide intermediates of formula $(V)^v$ wherein the alcohol moiety is protected with an appropriate alcohol protecting group P, such as those shown in Greene and Wuts, Protecting Groups in Organic Synthesis, 3rd. Ed., John Wiley & Sons.

Such intermediates are cyclised via reaction with dimethylformamide dimethylacetal in a suitable solvent such as toluene, followed by reaction with the corresponding hydrazine of the formula $R^{13}$—NH—$NH_2$ in a suitable solvent such as for example methanol. Then the alcohols are deprotected using methods known in the art such as those shown in Greene and Wuts, Protecting Groups in Organic Synthesis, 3rd. Ed., John Wiley & Sons.

As described above the compounds of the invention can have an asymmetric centre, said compounds, for example compounds of formula Ia, can be prepared in a similar way as those compounds of general formula I, by reacting a compound of formula:

IIIa

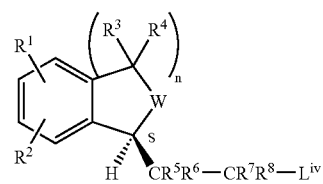

where n and $R^1$ to $R^8$ have the values defined for formula I above, —W— is —$CH_2$—, —O—, or —S—, and $L^{iv}$ is a leaving group, with a compound of formula (IV).

The reaction is preferably carried out using the same conditions as described above, such as in the presence of a base such as potassium carbonate, in an organic solvent such as a polar aprotic solvent, for example, acetonitrile, at a temperature of from 20° C. to 100° C. Examples of suitable leaving groups are mesylate, tosylate, triflate, chloride, bromide and iodide.

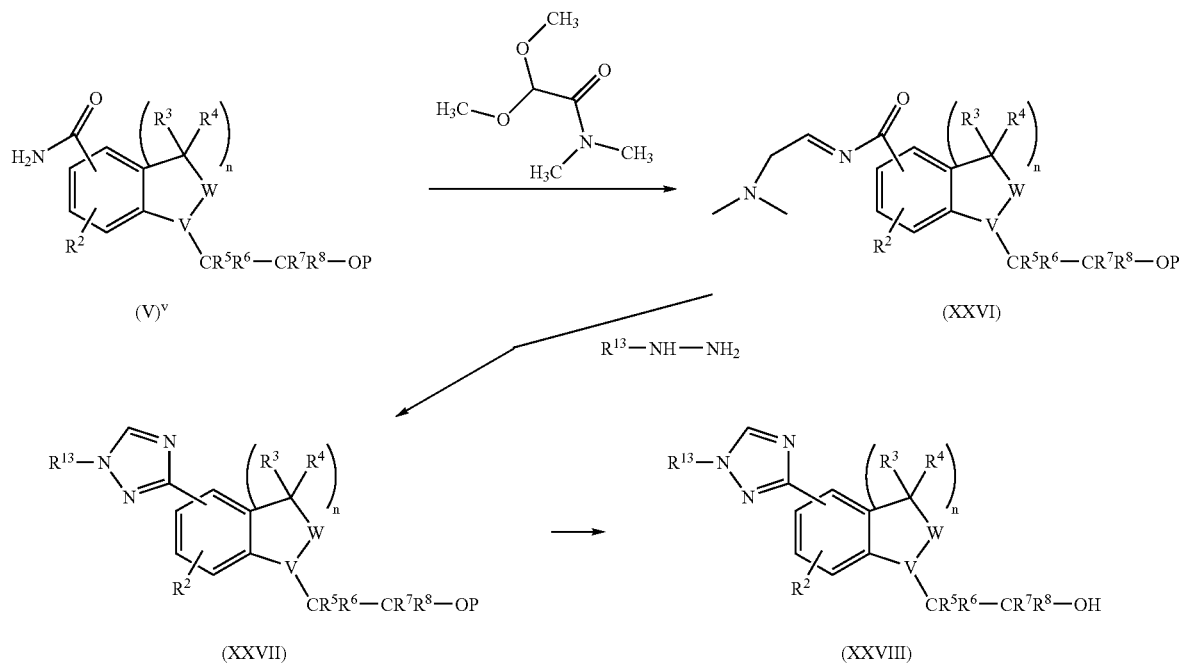

Intermediate compounds of formula (IIIa) can, for example, be prepared from the corresponding alcohols of the formula:

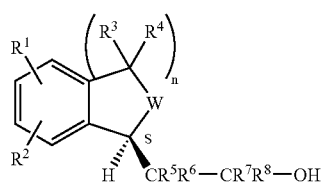
(Va)

where the substituents have the values defined for formula (IIIa) above, using standard methods known in the literature such as the ones shown in March, Advanced Organic Chemistry, Fourth Edition, for example the methods mentioned on pages 353 and 354.

Said alcohols of formula (Va) can be prepared via methods known in the literature such as for example the procedure described in TenBrink et al., *J. Med. Chem.*, 1996, 39, 2435-2437.

In the same way compounds of the invention having two asymmetric carbon atoms such as compounds of formula (Ib), can be prepared by reacting the corresponding chiral intermediates such as a compound of formula (IIIa) with a compound of the formula:

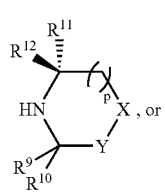
(IVa)

For compounds of formula (Ic), by reacting a compound of formula (IIIa) with a compound of the formula:

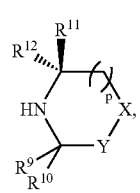
(IVb)

where the substituents have the values defined for formulae (Ib) and (Ic) above.

The reaction is preferably carried out in the presence of a base such as potassium carbonate, in an organic solvent such as a polar aprotic solvent, for example, acetonitrile, at a temperature of from 20° C. to 100° C. Examples of suitable leaving groups are mesylate, tosylate, triflate, chloride, bromide and iodide.

It will be appreciated that compounds of formulae (Ib) and (Ic) can also be produced by the preparation of compounds of formula (Ia) as the racemic mixture, followed by the separation of the corresponding isomers.

Intermediates of formula (IVa) wherein —X—Y— is —N(Z)-CH$_2$— can be synthesised via reaction of the unprotected piperazine of the formula

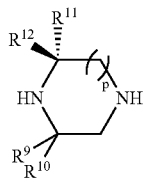

with a compound of formula Z-L$^{iii}$.

Such reactions are usually carried out in the presence of a palladium catalyst such as palladium acetate, BINAP ((R)-2,2'-bis(diphenylphosphino)-1,1'-binaphthyl) and a base such as Caesium carbonate.

In the same way intermediates of formula (IVb) wherein —X—Y— is —N(Z)-CH$_2$— can be synthesised via reaction of the unprotected piperazine of the formula

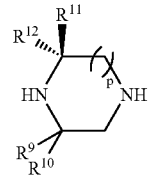

with a compound of formula Z-L$^{iii}$, using the same reaction conditions as described above.

Methods for the preparation of intermediates of formula (IVa) are further illustrated below. Said methods refer to compounds wherein —X—Y— is —N(Z)-CH$_2$— for methods (a) to (1) or —C(Q)(Z)-CH$_2$— for method (m), and wherein Z has different values and several substitution patterns. Additionally methods (n) to (s) illustrate methods for the preparation of intermediates of formula (IIIa) with different values of R$^1$. Any of variety of intermediates of formula (IVa) can be used for the preparation of the starting materials and can equally be used to obtain the corresponding intermediates of formula (IVb). They all use the common step of reaction of the unprotected piperazine with a compound of formula Z-L$^{iii}$ using the conditions described above, unless stated otherwise.

Method a)

Intermediates of formula (IVa) wherein Z is (xii)$_a$ and R$^{16}$ is CN can be prepared as shown in the scheme below:

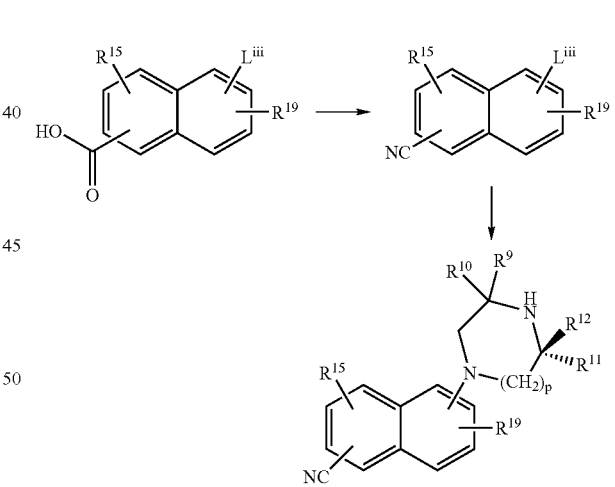

via conversion of the naphthoic acid into the corresponding naphthonitrile, followed by reaction with the unprotected piperazine as described above. The last reaction is preferably carried out in a solvent such as toluene and in the presence of a Palladium catalyst such as tris(dibenzylideneacetone) dipalladium(0), (R)-2,2'-bis(diphenylphosphino-1,1'-binaphthyl (BINAP), and a base such as sodium tert-butoxide.

The acid moiety is converted to the nitrile using general methods known in the art, for example the reaction can be carried out in the presence of an activating reagent such as methanesulfonyl chloride and reacting the reactive intermediate with ammonia in an organic solvent such as pyridine. Further addition of methanesulfonyl chloride dehydrates the intermediate carboxamide to the nitrile.

Method b)

Intermediates of formula (IVa) wherein Z is (xii)$_a$ and $R^{19}$ is Cl can be prepared as shown in the scheme below:

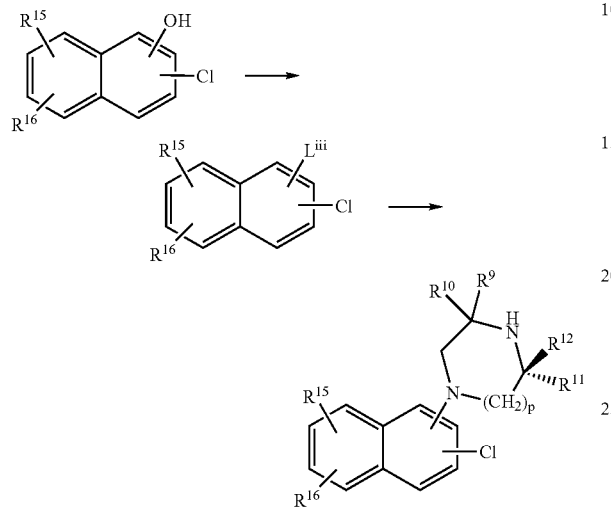

via conversion of the alcohol into a suitable leaving group $L^{iii}$, followed by reaction with the unprotected piperazine, as described above. When the $L^{iii}$ group is a triflate, reaction of the alcohol can, for example, be carried out in an organic solvent such as THF, in the presence of a base such as sodium tert-butoxide and a triflating agent such as, for example, N-phenyltrifluoromethanesulfonimide.

Method c)

Intermediates of formula (IVa) wherein Z is (xii)$_a$ and $R^{19}$ is CN can also be prepared as shown in the scheme below:

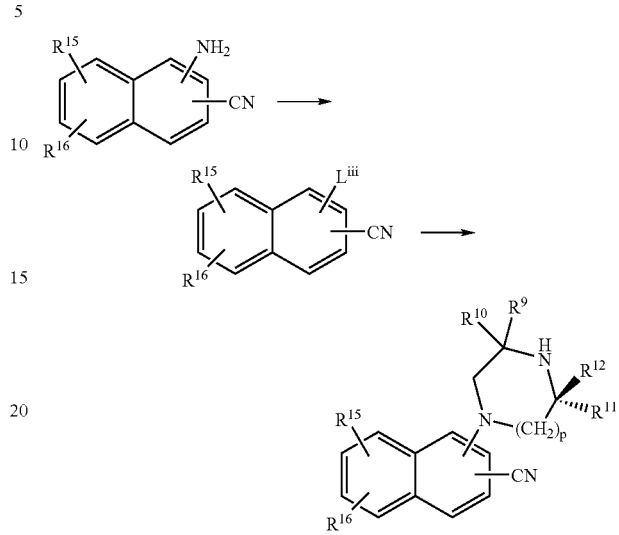

via conversion of the amino group of the corresponding aminonaphthonitrile into a suitable leaving group $L^{iii}$, followed by reaction with the unprotected piperazine, as described above. When the $L^{iii}$ group is a halide, the reaction can, for example, be carried out in the presence of copper (I)halide and nitrous acid, formed from a mixture of aqueous sodium nitrite and an acid such as hydrochloric acid.

Method d)

Intermediates of formula (IVa) wherein Z is (xii)$_a$ and $R^{16}$ and $R^{19}$ are both F can be prepared as shown in the scheme below:

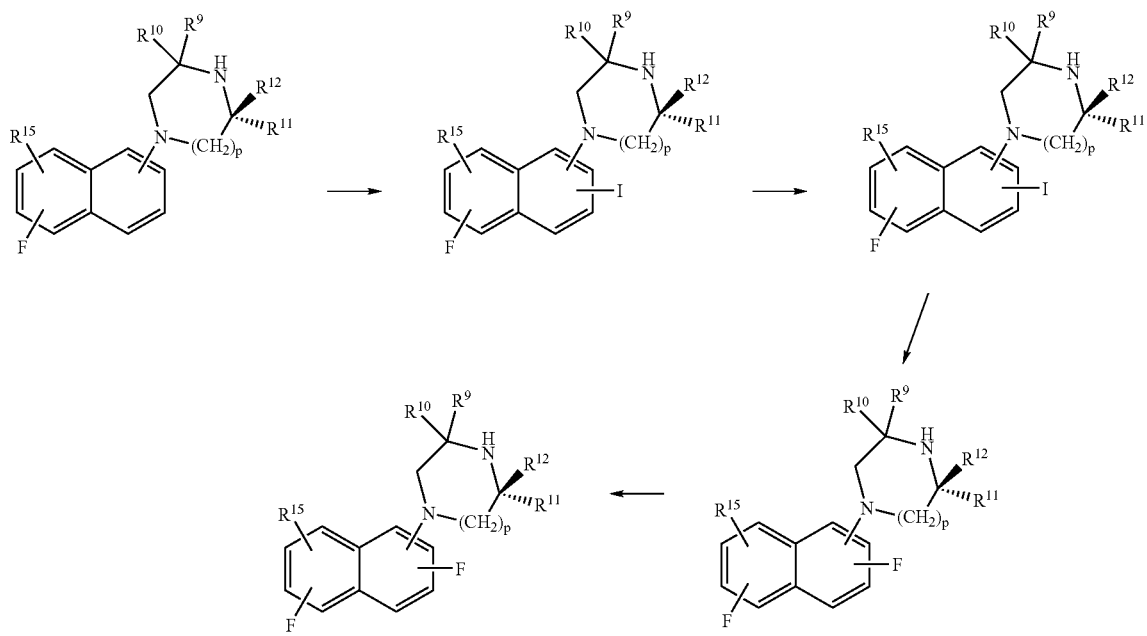

An iodo group is introduced into the napthalene ring, followed by protection of the nitrogen atom with a suitable protecting group P, conversion of the iodo group to a fluoro group and final deprotection.

The introduction of the iodo group is preferably carried out using general iodination conditions, such as in the presence of a mixture of bis(pyridine)iodonium(I) tetrafluoroborate and tetrafluoroboric acid, in an organic solvent such as dichloromethane.

The nitrogen atom can be protected using general conditions as described in Greene and Wuts, Protecting Groups in Organic Synthesis, 3rd. Ed., John Wiley & Sons. A suitable protecting group is for example CBZ. Said protecting groups can be cleaved following the procedures also described in Greene and Wuts, Protecting Groups in Organic Synthesis, 3rd. Ed., John Wiley & Sons.

The iodo group is converted to a fluoro group in the presence of N-fluorobenzenesulfonimide and a base such as tert-butillithium, in an organic solvent such as tetrahydrofuran.

Intermediates of formula (IVa) wherein Z is (xii)$_a$ and R$^{16}$ is F and R$^{19}$ is CN can be prepared as shown in the scheme below:

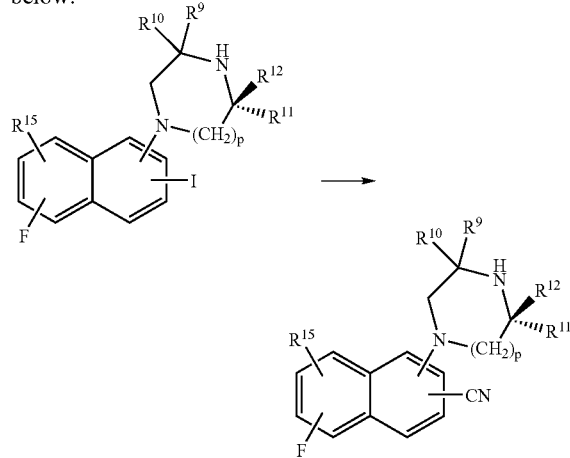

via conversion of the iodo group into the corresponding nitrile group.

The reaction is preferably carried out in the presence of a cyanide such as potassium cyanide, a catalyst such as copper(I) iodide and a palladium catalyst such as tetrakis(triphenylphosphine)palladium(0), in an organic solvent such as tetrahydrofuran. The reaction mixture is preferably heated, for example, at a temperature around 100° C.

Method e)

Intermediates of formula (IVa) wherein Z is (xii)$_a$ and R$^{16}$ and R$^{19}$ are both methyl can be prepared as shown in the scheme below:

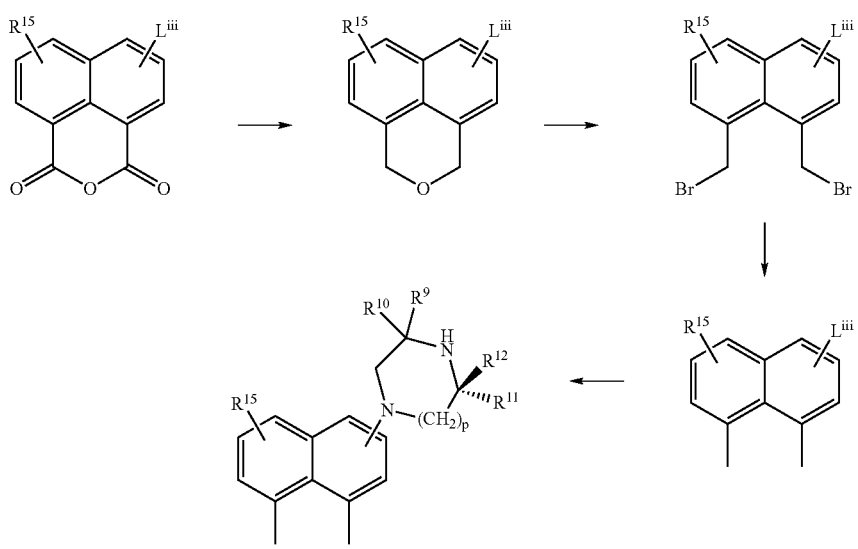

wherein the 1H,3H-naphtho[1,8-cd]pyran-1,3-dione is reduced to the corresponding 1H,3H-naphtho[1,8-cd]pyran. Then the pyran ring of the 1H,3H-naphtho[1,8-cd]pyran is then opened to give the corresponding bis(bromomethyl) naphthalene derivative, which is subsequently converted to the dimethyl compound. Reaction with the corresponding unprotected piperazine is performed as described above.

The reduction is preferably carried out in the presence of a reducing agent such as sodium borohydride, in an organic solvent such as ethanol, followed by reaction with an acid such as trifluoroacetic acid, in an organic solvent such as dichloromethane and in the presence of a reducing agent such as triethylsilane.

The pyran ring is preferably opened in the presence of a reagent such as boron tribromide, in an organic solvent such as dichloromethane at reflux.

The dimethyl compound is preferably prepared in the presence of a reducing agent such as sodium borohydride, in the presence of an activating agent such as silver nitrate, in an organic solvent such as dimethylformamide.

Method f)

Intermediates of formula (IVa) wherein Z is (xii)$_a$ and R$^{16}$ is F can be prepared as shown in the scheme below:

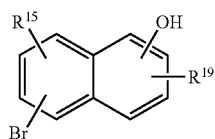 → 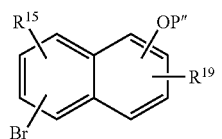 → 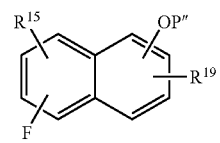

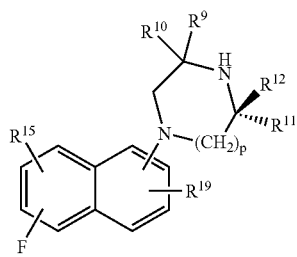 ← 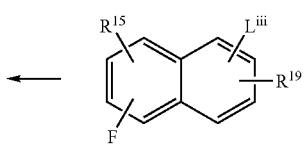 ← 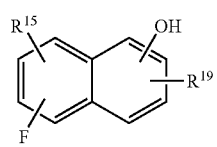

wherein the naphthol compound is protected with a suitable alcohol protecting group P'', as described in Greene and Wuts, Protecting Groups in Organic Synthesis, 3rd. Ed., John Wiley & Sons, followed by conversion of the bromo group into a fluoro group. The alcohol is deprotected and converted into a suitable leaving group $L^{iii}$, then reacted with the corresponding unprotected piperazine, as described above.

The alcohol can be protected using general conditions, as described in Greene and Wuts, Protecting Groups in Organic Synthesis, 3rd. Ed., John Wiley & Sons, a suitable protecting group is, for example, tert-butyldimethylsilane. Said protecting groups can be cleaved following the procedures also described in Greene and Wuts, Protecting Groups in Organic Synthesis, 3rd. Ed., John Wiley & Sons.

The bromo group is converted to a fluoro group in the presence of N-fluorobenzenesulfonimide and a base such as tert-butillithium, in an organic solvent such as tetrahydrofuran.

The conversion of the alcohol into a suitable leaving group such as a triflate can be carried out in an organic solvent such as THF in the presence of a base such as sodium tert-butoxide and a triflating agent such as, for example, N-phenyltrifluoromethanesulfonimide.

Method g)

Intermediates of formula (IVa) wherein Z is $(xii)_a$ and $R^{16}$ is Cl can also be prepared as shown in the scheme below:

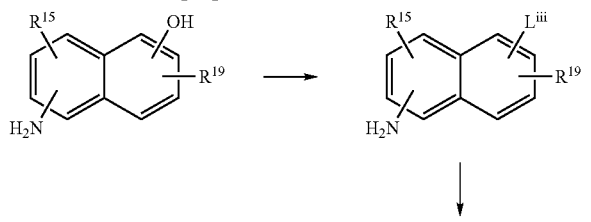

-continued

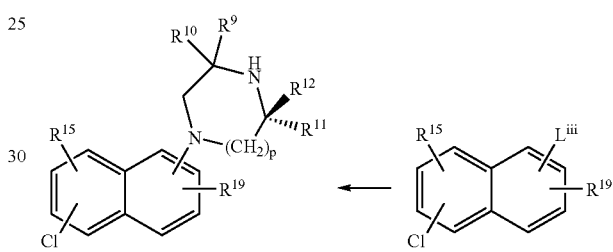

via conversion of the alcohol into a suitable leaving group $L^{iii}$, the amino group into a chloro group, followed by reaction with the unprotected piperazine, as described above. When the $L^{iii}$ group is a triflate, the first reaction can, for example, be carried out in an organic solvent such as THF, in the presence of a base such as sodium tert-butoxide and a triflating agent such as, for example, N-phenyltrifluoromethanesulfonimide.

The amino group is preferably reacted with copper(I) chloride and nitrous acid, prepared from a mixture of aqueous sodium nitrite and an acid such as hydrochloric acid.

Method h)

Intermediates of formula (IVa) wherein Z is $(xii)_a$ and $R^{16}$ is CN can also be prepared as shown in the scheme below:

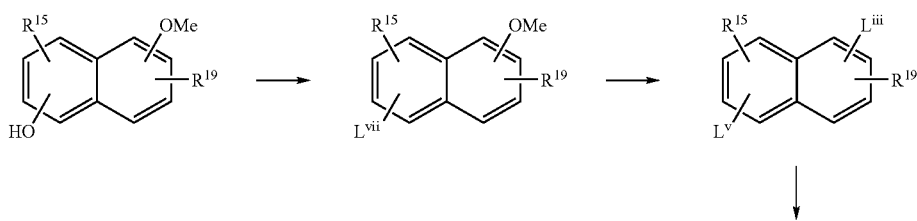

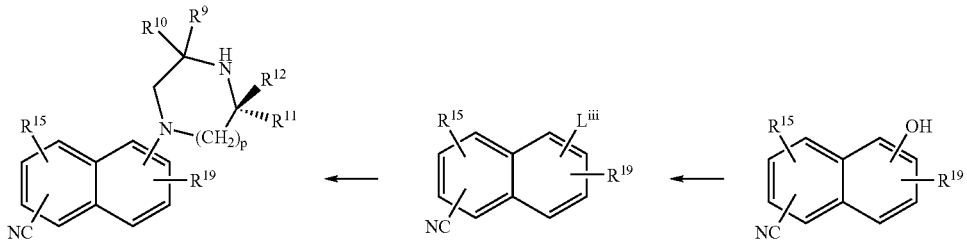

via conversion of the alcohol into a suitable leaving group $L^v$, deprotection of the ether to give an alcohol, displacement of $L^v$ with a nitrite group, conversion of the alcohol into a suitable leaving group $L^{iii}$, followed by reaction with the unprotected piperazine, as described above.

The conversions of the alcohol into suitable leaving groups $L^{iii}$ and $L^v$, when the $L^{iii}$ and $L^v$ groups are triflates can, for example, be carried out in an organic solvent such as THF, in the presence of a base such as sodium tert-butoxide and a triflating agent such as, for example, N-phenyltrifluoromethanesulfonimide.

The methyl ether is deprotected with boron tribromide in a suitable organic solvent such as dichloromethane.

The displacement of $L^v$ with a nitrile group is preferably carried out by heating the compound in a suitable organic solvent such as DMF, in the presence of a cyanide such as, for example, zinc cyanide and a palladium catalyst such as tetrakis triphenylphosphine palladium(0).

Method i)

Intermediates of formula (IVa) wherein Z is (xxi), m and s are both 1 and -T- is —O—, can be prepared as shown in the scheme below:

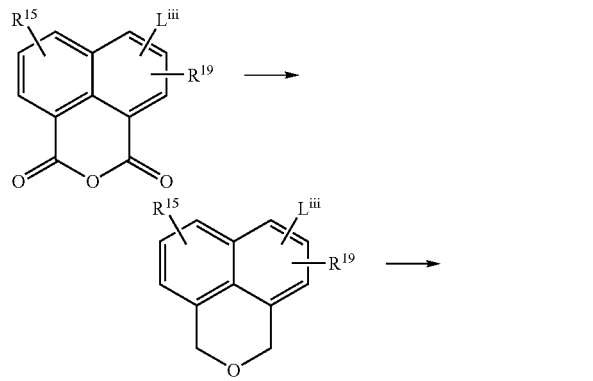

wherein the 1H,3H-naphtho[1,8-cd]pyran-1,3-dione is reduced to the corresponding 1H,3H-naphtho[1,8-cd]pyran, followed by reaction with the corresponding unprotected piperazine, as described above.

The reduction is preferably carried out in the presence of a reducing agent such as sodium borohydride in an organic solvent such as ethanol, followed by reaction with an acid such as trifluoroacetic acid in an organic solvent such as dichloromethane and in the presence of an ionic reducing agent such as triethylsilane.

Method j)

Intermediates of formula (IVa) wherein Z is (xxi), and -T- is —CH$_2$—, can be prepared as illustrated in the scheme below for compounds wherein m is 1, s is 0 and $L^{iii}$ is a suitable leaving group, such as bromide:

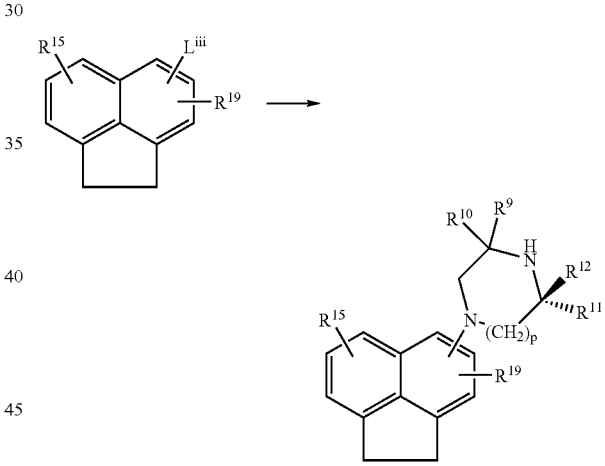

via reaction of the corresponding 5-bromo-1,2-dihydroacenaphthylene with the corresponding unprotected piperazine as described above.

Method k)

Intermediates of formula (IVa) wherein Z is (xxi), both m and s are 0, and -T- is —CH═CH— can be prepared from the corresponding 1,2-dihydroacenaphthylene as shown in the scheme below:

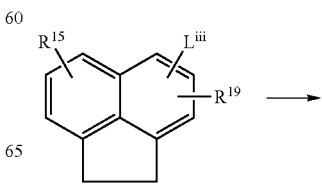

-continued

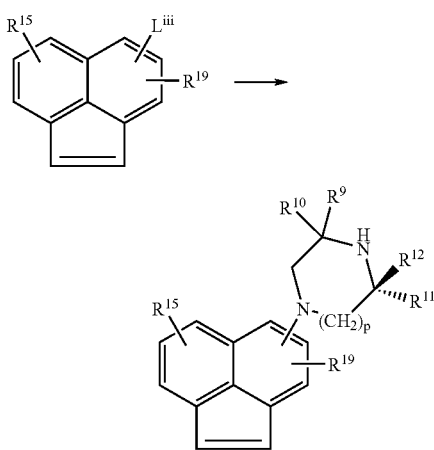

via aromatisation in the presence of a suitable reagent such as DDQ, and in a suitable solvent such as dichloromethane, followed by reaction with the corresponding unprotected piperazine, as described above.

Method l)

Intermediates of formula (IVa) wherein Z is (xxi), m and s are both 1 and -T- is —S—, can be prepared as shown in the scheme below:

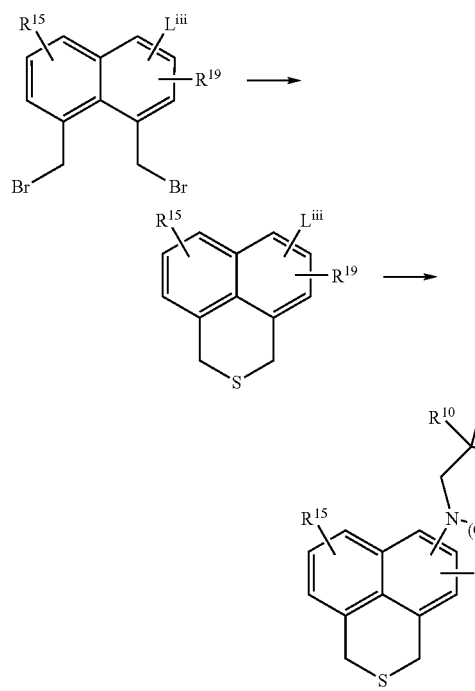

wherein the bis(bromomethyl)naphthalene intermediate (described above) is cyclised to give the thiopyran ring, followed by reaction with the corresponding unprotected piperazine, as described above.

The cyclisation is preferably carried out with a sulfide such sodium sulfide nonahydrate, in an organic solvent such as dimethylformamide.

Compounds of formula I wherein Z is (xxi), m is 0, s is 1, and -T- is —C(O)— can be prepared from the corresponding 1,2-dihydroacenaphth-1-ol, as shown in the scheme below:

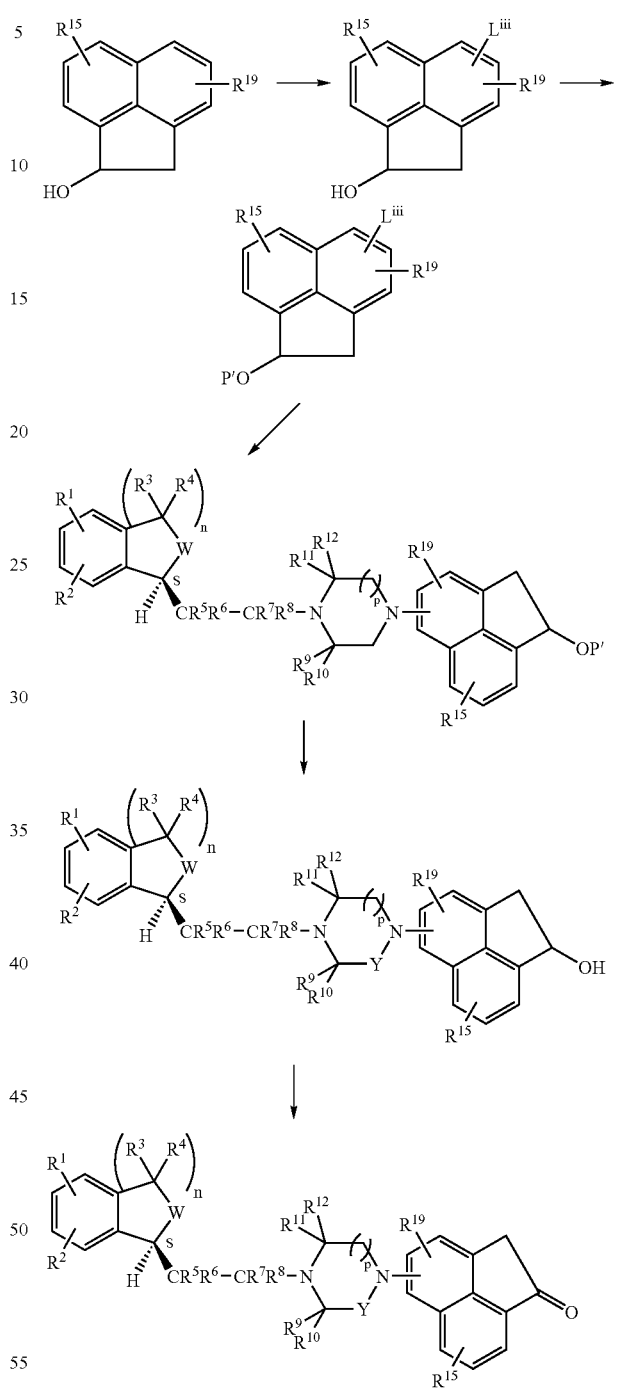

Method m)

Intermediates of formula (IVa) wherein —X—Y— is

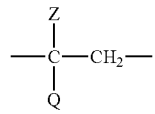

Q is hydrogen and for example Z is (xii)$_a$ can be prepared as shown in the scheme below:

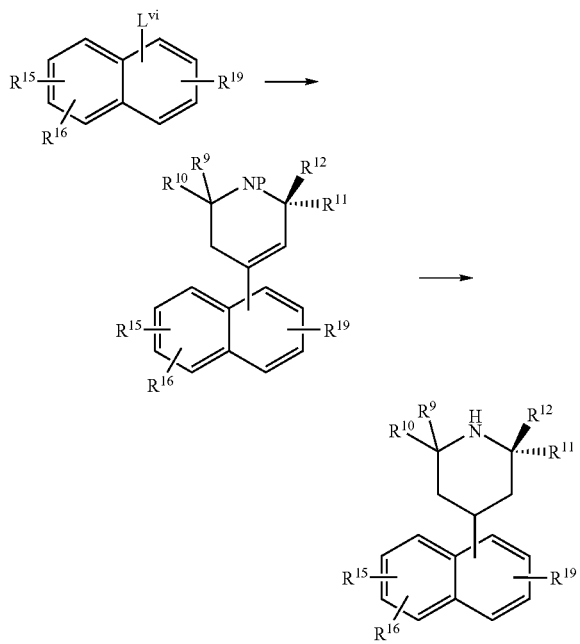

via reaction of the Z-L$^{vi}$ compound, wherein L$^{vi}$ is a suitable leaving group such as triflate, with a N-protected 4-(4,4,5,5-tetramethyl-1,3,2-dioxaborolan-2-yl)-3,6-dihydro-1(2H)-pyridine, (which can be synthesised according to the procedure described by Paul R. Eastwood in *Tetrahedron Letters*, 2000, 41, 3705-3708). The reaction is carried out in the presence of a base such as potassium carbonate and a palladium catalyst such as bis(diphenylphosphino)-ferrocenedichloropalladium(II) in a suitable solvent such as DMF, to give the corresponding protected 3,6-dihydro-1(2H)-pyridine, which is reduced to the corresponding protected piperidine, and then deprotected.

The piperidine compound can be prepared by reduction with hydrogen in the presence of a palladium catalyst, such as palladium on carbon in a suitable solvent such as methanol.

The deprotection of the piperidine can be carried out according to the nitrogen-protecting group (P) used. Suitable protecting groups are described in Greene and Wuts, Protecting Groups in Organic Synthesis, 3rd. Ed., John Wiley & Sons and include tert-butylcarboxynyl (BOC), which can be deprotected, for example, in a suitable solvent such as dichloromethane and in the presence of trifluoroacetic acid.

Method n)

Intermediates of formula (IIIa) wherein R$^1$ is

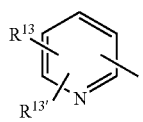

can be prepared from the corresponding protected alcohols of formula (Va) via deprotection following suitable conditions described in Greene and Wuts, Protecting Groups in Organic Synthesis, 3rd. Ed., John Wiley & Sons. Suitable protecting groups (P') are also described in the above reference and include the tertbutyldimethylsilyl group. Said alcohols of formula (Va) can be prepared as shown in the scheme below:

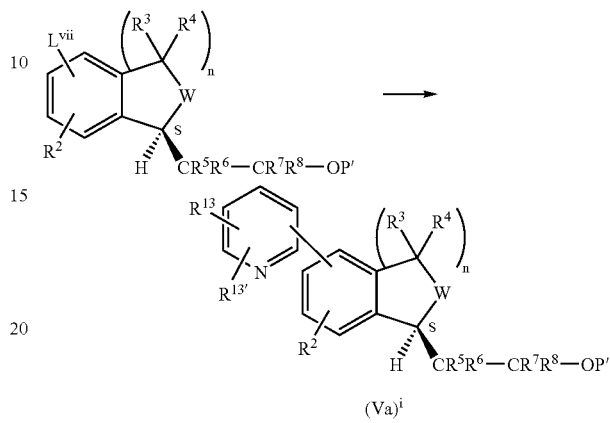

wherein L$^{vii}$ is a suitable leaving group such as bromide, via reaction with the corresponding dioxaborinanyl pyridine. This reaction is preferably carried out in the presence of a suitable solvent such as toluene and in the presence of a palladium catalyst such as tetrakis(triphenylphosphine)palladium and a suitable base such as potassium hydroxide.

Method o)

Intermediates of formula (IIIa) wherein R$^1$ is SO$_2$NR$^{13}$R$^{14}$ can be prepared from the corresponding protected alcohols of formula (Va)$^{ii}$ via deprotection following suitable conditions described in Greene and Wuts, Protecting Groups in Organic Synthesis, 3rd. Ed., John Wiley & Sons. Suitable protecting groups (P') are also described in the above reference and include tertbutyldimethylsilyl groups. Said alcohols of formula (Va)$^{ii}$ can be prepared as shown in the scheme below:

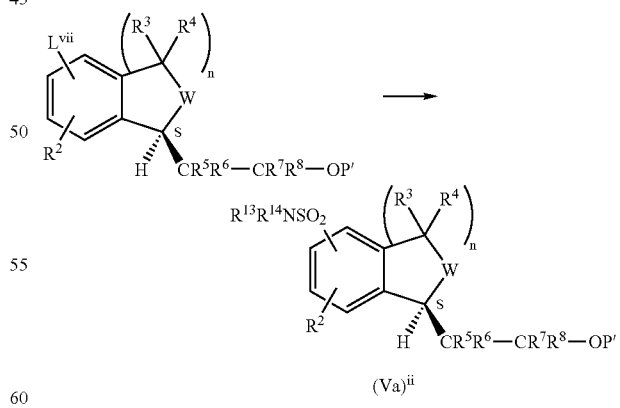

wherein L$^{vii}$ is a suitable leaving group such as bromide, via formation of the corresponding sulfonamide. This reaction is preferably carried out in a suitable solvent such as tetrahydrofuran and in the presence of sulphur dioxide and a suitable base such as n-butyllithium, followed by reaction in a suitable solvent such as dichloromethane in the presence of N-chlorosuccinimide and the corresponding amine (HNR$^{13}$R$^{14}$).

Method p)

Intermediates of formula (IIIa) wherein R$^1$ is —(CH$_2$)$_t$—R$^{21'}$, t is 0 and R$^{21'}$ is a protected amino group can be prepared from the corresponding protected alcohols of formula (Vb), as shown in scheme below:

a catalyst such as tris(dibenzylidene-acetone)dipalladium, a suitable ligand such as BINAP and a suitable base such as sodium tert-butoxide.

The amino group is preferably deprotected in basic mild conditions such as in the presence of hydroxylamine hydrochloride and sodium acetate, in a suitable solvent such as methanol.

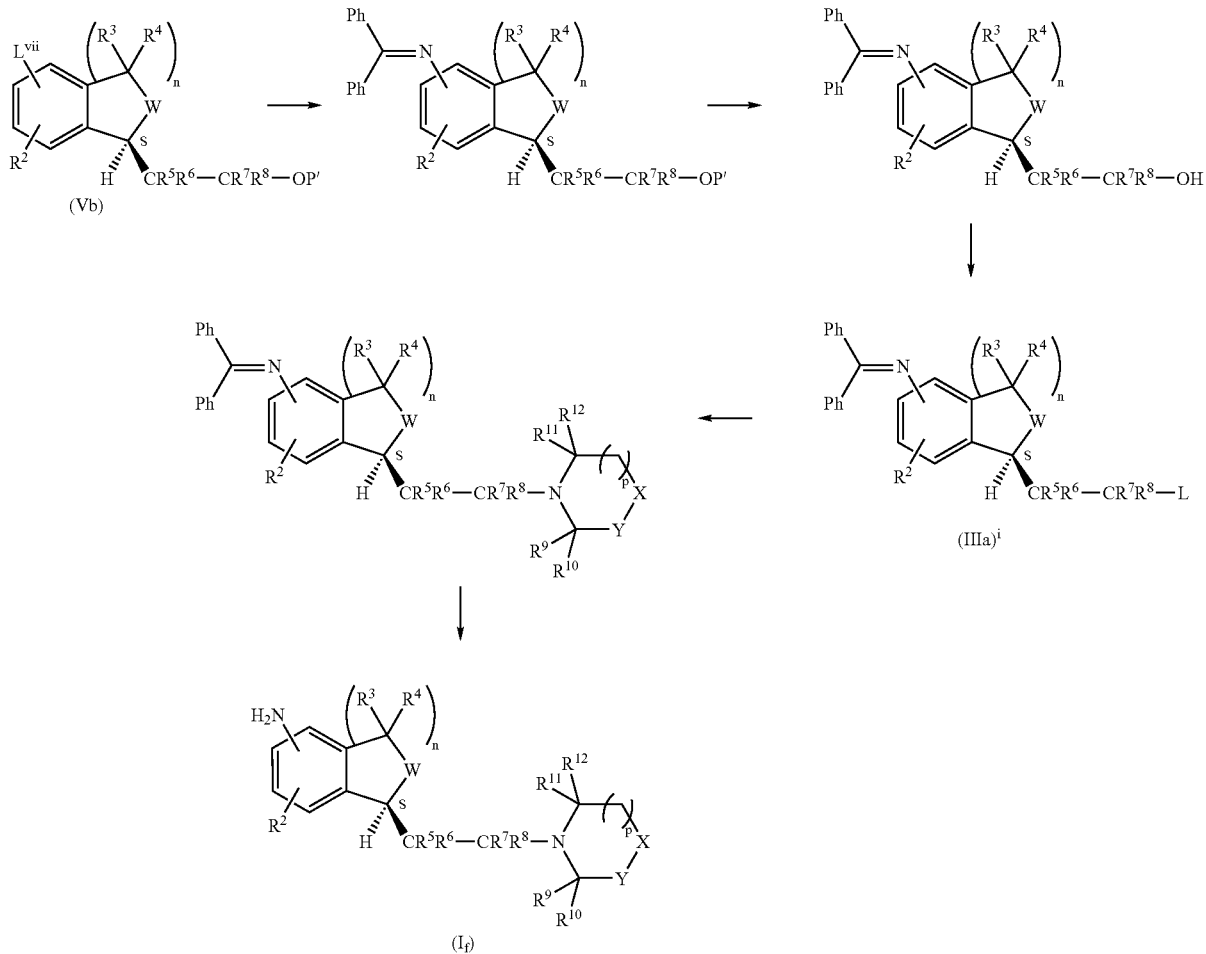

wherein L$^{vii}$ is a suitable leaving group such as bromide, via reaction with a suitable imine, such as for example benzophenone imine. Suitable protecting groups (P') are described in Greene and Wuts, Protecting Groups in Organic Synthesis, 3rd. Ed., John Wiley & Sons, and include tert-butyldimethylsilyl groups. Said protected alcohols are deprotected following suitable conditions as also described in the above reference, and are subsequently converted to intermediates of formula (IIIa)$^i$.

Said intermediates of formula (IIIa)$^i$ are reacted with the corresponding unprotected piperazine using standard conditions described above. The last step is the deprotection of the protected amino group to give the corresponding free amino compound of formula (I$_f$).

The displacement of the L$^{vii}$ group is preferably carried out in a suitable solvent such as toluene, in the presence of Compounds of formula (I$_f$) can be used as intermediates for the synthesis of compounds of formula I wherein R$^1$ is —(CH$_2$)$_t$—R$^{21}$, wherein t is 0 and R$^{21}$ is

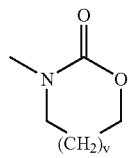

via reaction with L$^{viii}$-CH$_2$—(CH$_2$)$_v$—CH$_2$—O—CO-L$^{ix}$ wherein both L$^{viii}$ and L$^{ix}$ are suitable leaving groups such as for example chloride, in the presence of a suitable base such as pyridine, in a suitable solvent such as DMF, as shown in the scheme below:

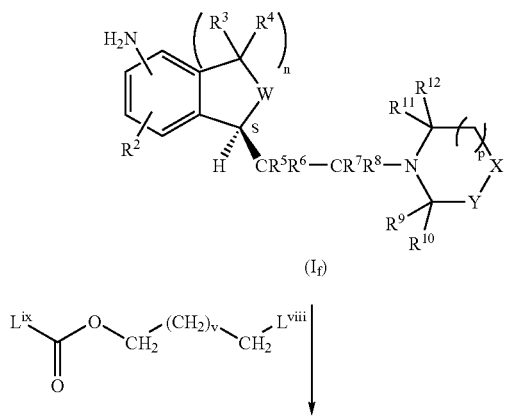

(I<sub>f</sub>)

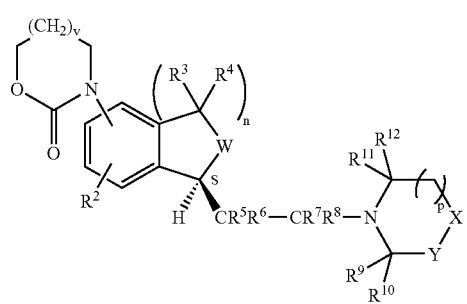

wherein $L^{vii}$ and $L^x$ are suitable leaving groups, and P' is a suitable alcohol protecting group such as described in Greene and Wuts, Protecting Groups in Organic Synthesis, 3rd. Ed., John Wiley & Sons, for example a tertbutyldimethylsilyl group.

Intermediate (Vb) is converted to the corresponding carboxaldehyde via reaction with dimethylformamide in the presence of a suitable base such as tert-butyllithium and in a suitable solvent such as THF. Said aldehyde is reduced to the corresponding alcohol using standard reducing agents, such as for example sodium borohydride in a suitable solvent such as ethanol. The resulting primary alcohol is converted into a suitable leaving group $L^x$, such as for example mesylate, in the presence of mesyl chloride and a suitable base such as triethylamine. Said mesylate is subsequently displaced with the corresponding nitrogen containing compound $HR^{21}$ in the presence of a suitable base, such as for example sodium hydride, and in a suitable solvent such as DMF.

Method r)

Intermediates of formula (IIIa) wherein $R^1$ is —$(CH_2)_t$—$R^{21}$, t is 0 and $R^{21}$ is

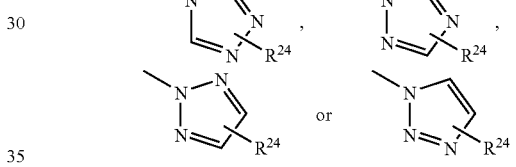

Method q)

Intermediates of formula (IIIa) wherein $R^1$ is —$CH_2$—$R^{21}$ can be prepared from the corresponding protected alcohols of formula (Vb), as shown in scheme below:

can be prepared from the corresponding protected alcohols of formula (Vb), as shown in scheme below:

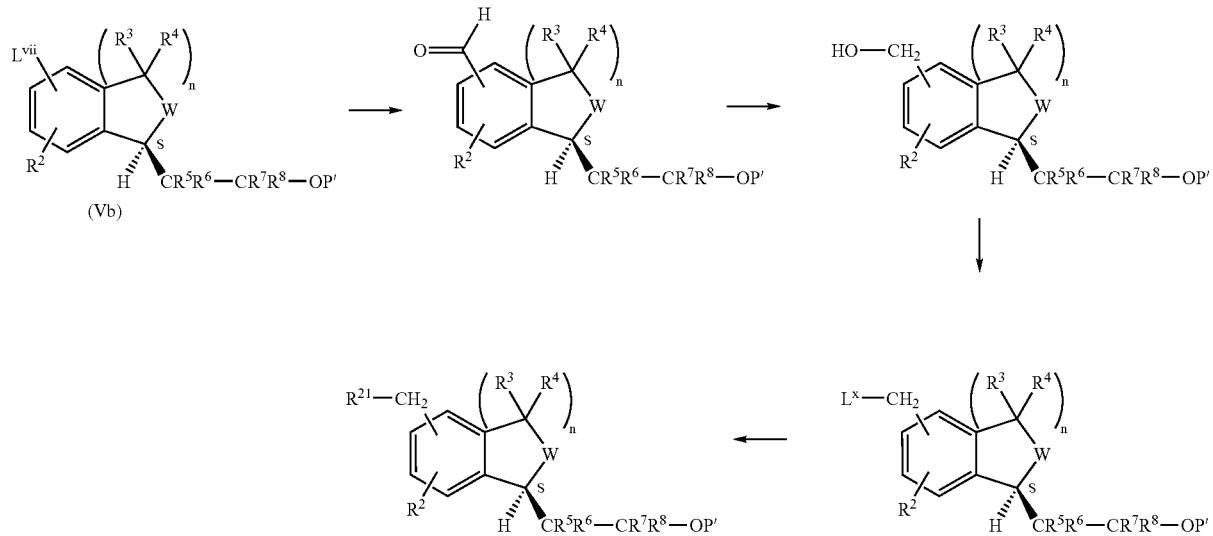

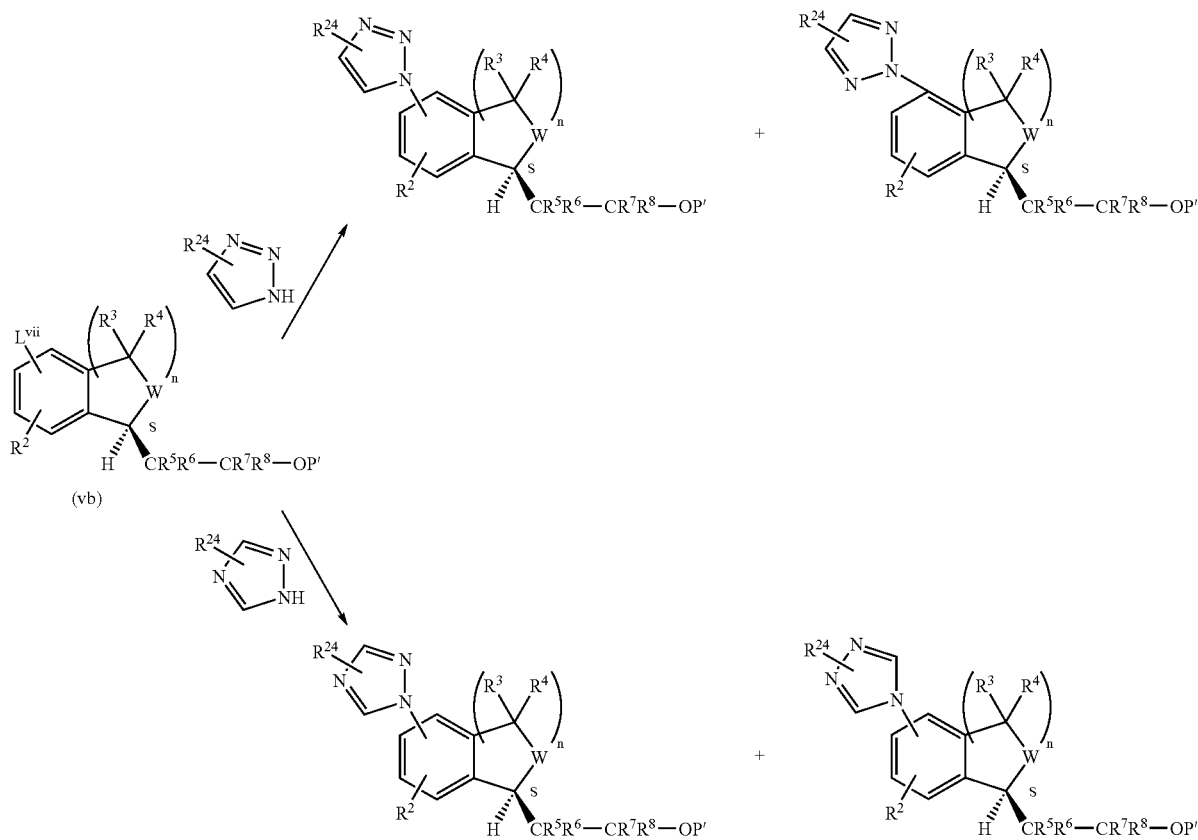

(vb)

wherein $L^{vii}$ is a suitable leaving group, such as for example bromide, chloride, iodide or mesylate. P' is a suitable alcohol protecting group such as described in Greene and Wuts, Protecting Groups in Organic Synthesis, 3rd. Ed., John Wiley & Sons, for example a tertbutyldimethylsilyl group.

$L^{vii}$ of intermediate (Vb) is displaced via reaction with the corresponding triazole, in a suitable solvent such as DMF and in the presence of a catalytic amount of copper iodide and a suitable base such as potassium carbonate.

It will be appreciated that the above reaction scheme is illustrated for compounds wherein the alcohol is protected but it can equally be carried out for the corresponding unprotected alcohols wherein P' is hydrogen.

Method s)

Intermediates of formula (IIIa) wherein $R^1$ is —$(CH_2)_t$—$R^{21}$, t is 0 and $R^{21}$ is

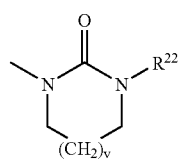

can be prepared from the corresponding protected alcohols of formula (Vb), as illustrated in the scheme below, for compounds wherein $R^{21}$ is 2-imidazolidinone:

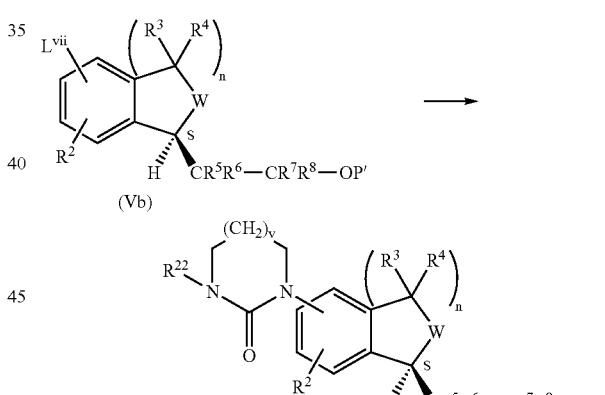

wherein $L^{vii}$ is a suitable leaving group such as for example bromide, chloride, iodide or mesylate. P' is a suitable alcohol protecting group such as described in Greene and Wuts, Protecting Groups in Organic Synthesis, 3rd. Ed., John Wiley & Sons, for example a tertbutyldimethylsilyl group.

$L^{vii}$ of intermediate (Vb) is displaced via reaction with the corresponding imidazolidinone, in a suitable solvent such as DMF and in the presence of a catalytic amount of copper iodide and a suitable base such as potassium carbonate.

It will be appreciated above reaction scheme is illustrated for compounds wherein the alcohol is protected but it can equally be carried out for the corresponding unprotected alcohols wherein P' is hydrogen.

Alternatively, compounds of formula I wherein $R^1$ is —$(CH_2)_t$—$R^{21}$ and t is 0, can be prepared from the reaction of compounds of formula (IIIa)$^{ii}$ as shown in scheme below:

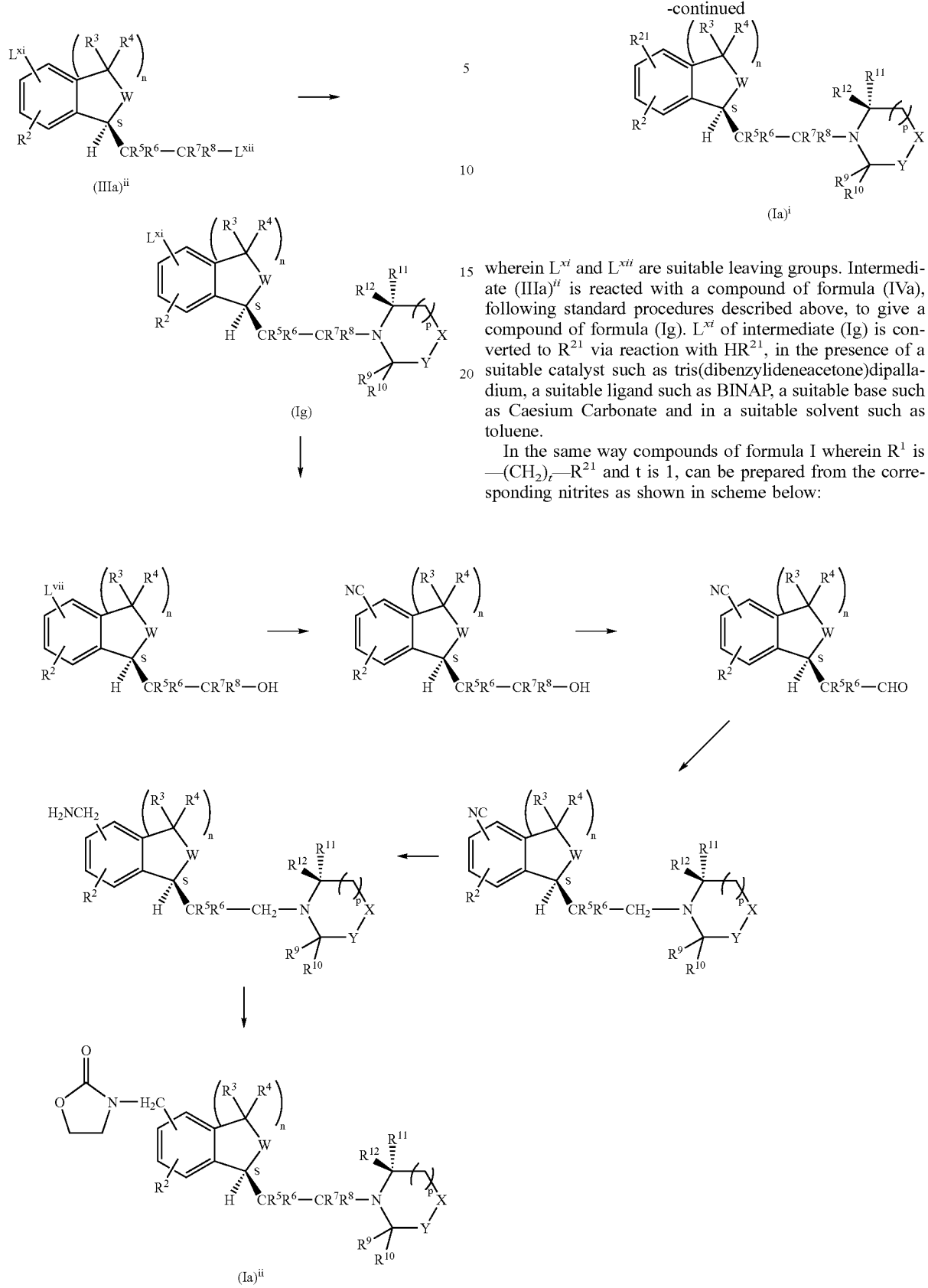

wherein $L^{xi}$ and $L^{xii}$ are suitable leaving groups. Intermediate $(IIIa)^{ii}$ is reacted with a compound of formula (IVa), following standard procedures described above, to give a compound of formula (Ig). $L^{xi}$ of intermediate (Ig) is converted to $R^{21}$ via reaction with $HR^{21}$, in the presence of a suitable catalyst such as tris(dibenzylideneacetone)dipalladium, a suitable ligand such as BINAP, a suitable base such as Caesium Carbonate and in a suitable solvent such as toluene.

In the same way compounds of formula I wherein $R^1$ is $-(CH_2)_t-R^{21}$ and t is 1, can be prepared from the corresponding nitriles as shown in scheme below:

wherein $L^{xiii}$ is a suitable leaving group such as for example bromide, chloride, iodide or mesylate. Said leaving group is converted to the nitrile using standard methods described above. The free alcohol can be converted to a suitable leaving group which can be displaced with a compound of formula (IVa). Alternatively said alcohol can be oxidised to the corresponding aldehyde using standard oxidating procedures known in the literature, followed by reductive amination in the presence of the unprotected piperazine using the standard conditions described above. The nitrile is then reduced to the corresponding amine in the presence of a suitable reducing agent such as for example lithium aluminium hydride. Said amine can be converted to several of the $R^{21}$ substituents, such as for example,

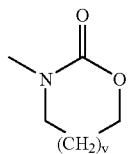

via cyclisation in the presence of $L^{viii}$-CH$_2$—(CH$_2$)$_v$—CH$_2$—O—CO-$L^{ix}$ as illustrated in method (p) above.

As shown above substituents in any of the aromatic rings, such as $R^1$ and $R^2$, may be present in the starting materials or introduced at an appropriate point in the manufacture of the product compound. If necessary said substituents may be protected during the reaction procedure.

Compounds of the invention have been demonstrated to be active at the serotonin, 5-HT 1D receptor. Their binding activity has been demonstrated in a test described by Pullar I. A. et al, European Journal of Pharmacology, 407 (2000), 39-40.

As mentioned above, the compounds of the invention and their pharmaceutically acceptable salts have useful central nervous system activity. They have been shown to increase release of tritiated-5HT from guinea pig cortical slices in a test with the following procedure.

Cortical slices from the brains of male guinea pigs were incubated with 50 nM [$^3$H]-5-HT for 30 minutes at 37° C. The slices were washed in basal buffer containing 1 µM paroxetine and then transferred to baskets. The baskets were used to transfer the tissue between the washing and release buffers, all of which contained 1 µM paroxetine.

In order to obtain a stable baseline release, the slices were incubated for 11 minutes in buffer and then transferred for 4 minutes to a second tube containing buffer. Following incubation they were again transferred, for a further 4 minutes, to a buffer in which NaCl had been substituted, on an equimolar basis, to give a KCl concentration of 30 mM (release sample).

The tritium in the tissue samples and in the buffers from the three incubation periods was estimated by liquid scintillation spectroscopy. Test compound was present throughout the three incubation periods. The compounds of the invention enhanced release of 5-HT.

The compounds of the invention are serotonin reuptake inhibitors, and possess excellent activity as, for example, in the test described by Carroll et al., J. Med. Chem. (1993), 36, 2886-2890, in which the intrinsic activity of the compound to competitively inhibit the binding of selective serotonin reuptake inhibitors to the serotonin transporter is measured. These results were also confirmed by in vivo tests in which the effect of the compound on a behavioural syndrome in mice dosed with 5-HTP and a monoamine oxidase inhibitor (MAOI) such as pargyline, is measured, see Christensen, A. V., et al., Eur. J. Pharmacol. 41, 153-162 (1977).

In view of the selective affinity of the compounds of the invention for the serotonin receptors, they are indicated for use in treating a variety of conditions associated with serotonin dysfunction in mammals including disorders of the central nervous system such as depression, bipolar disorder, anxiety, obesity, eating disorders such as anorexia and bulimia, alcoholism, pain, hypertension, ageing, memory loss, sexual dysfunction, psychotic disorders, schizophrenia, gastrointestinal disorders, headache, cardiovascular disorders, smoking cessation, epilepsy, drug abuse and addiction, emesis, Alzheimer's disease and sleep disorders. The compounds of the invention are principally intended for the treatment of depression or anxiety, or disorders with depressive or anxiety symptoms.

Accordingly the present invention includes the use of a compound of formula I or a pharmaceutically acceptable salt thereof in the manufacture of a medicament for the treatment of a disorder associated with serotonin dysfunction in mammals, including any of the disorders mentioned above.

The compounds of the invention are effective over a wide dosage range, the actual dose administered being dependent on such factors as the particular compound being used, the condition being treated and the type and size of animal being treated. However, the dosage required will normally fall within the range of 0.001 to 20, such as 0.01 to 20 mg/kg per day, for example in the treatment of adult humans, dosages of from 0.5 to 100 or 200 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt thereof, associated with a pharmaceutically acceptable diluent or carrier. In making the compositions of the invention, the active ingredient will usually be mixed with a carrier, or diluted by a carrier, or enclosed within a carrier which may be in the form of a capsule, sachet, paper or other container. More than one active ingredient or excipient may, of course, be employed. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin, syrup, methyl cellulose, methyl- and propylhydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Preparations and Examples illustrate routes to the synthesis of the compounds of the invention.

PREPARATION

(1S)-1-(2-Hydroxyethyl)-3,4-dihydro-1H-2-benzopyran-6-carboxamide

Method A a) 2-(6-Bromo-3,4-dihydro-1H-2-benzopyran-1-yl)acetic acid ethyl ester A solution of 3-bromophenethyl alcohol (15 g, 74.6 mmol) and ethyl-3-3-diethoxypropionate (17.1 g, 89.9 mmol) in dichloromethane (60 mL) under an atmosphere of nitrogen was cooled to −10° C. and treated with a 4N solution of titanium tetrachloride in dichloromethane (61.5 ml, 3.3 equiv.) over a period of 15 minutes. The reaction mixture was then allowed to warm to room temperature. Analysis of an aliquot by HPLC indicated that the reaction was complete after 3 h at ambient temperature. The reaction mixture was then cooled to 0° C. and water slowly added (over 15 minutes) maintaining the temperature between 0 and 10° C. The mixture was agitated for an additional period of 15 minutes and layers were separated. After washing with water (60 mL), 0.5N NaOH (80 mL), then brine (80 mL), the organic layer was concentrated in vacuo to give the title compound as an oil.

b) 2-(6-Bromo-3,4-dihydro-1H-2-benzopyran-1-yl)acetic acid 2-(6-Bromo-3,4-dihydro-1H-2-benzopyran-1-yl)acetic acid ethyl ester (20 g, 66.9 mmol) was dissolved in absolute ethanol (40 mL). The mixture was cooled to 0° C. and 4N NaOH (22 mL) was added over five minutes. The reaction mixture was then stirred for 1.5 h at room temperature. Water (22 mL) was added, and the solution washed with dichloromethane (70 mL). The aqueous layer was collected and acidified with 6N HCl (17 mL) and extracted with dichloromethane (70 mL). The organic layer was concentrated in vacuo to give an off-white solid. This solid was suspended in toluene (66 mL) and heated to 100° C. The resulting solution was cooled to 80° C. and cyclohexane (66 mL) added. The resulting suspension was cooled to room temperature and stirred for an hour. The solid was then filtered off, washed with cyclohexane (20 mL), and dried at 40° C. in vacuo to give the title compound as a white solid.

c) 2-((1S)-6-Bromo-3,4-dihydro-1H-2-benzopyran-1-yl)acetic acid

To a suspension of 2-(6-bromo-3,4-dihydro-1H-2-benzopyran-1-yl)acetic acid (55 g, 203 mmol) in acetonitrile (375 mL) and water (40 mL) was added a solution of (R)-1-(4-methylphenyl)ethylamine (27.45 g, 203 mmol) in acetonitrile (370 mL). The mixture was heated to reflux and the resulting solution cooled to room temperature. A precipitate appeared upon cooling. After stirring for 2 h the salt was filtered off, washed with 95/5 acetonitrile/water (80 mL), and dried in vacuo. The salt was recrystallized in 95/5 acetonitrile/water to give a solid which was suspended in water (390 mL) and treated with 6N HCl (17 mL). After stirring for 1.5 h, filtration, washing, and drying gave the title compound (98% e.e.) as a white solid.

d) 2-((1S)-6-Bromo-3,4-dihydro-1H-2-benzopyran-1-yl)ethanol

To a solution of 2-((1S)-6-bromo-3,4-dihydro-1H-2-benzopyran-1-yl)acetic acid (21.3 g, 78.6 mmol) in anhydrous THF (65 mL) under an atmosphere of nitrogen and cooled to 0° C., was added dropwise borane.THF complex in THF (1M) (94 mL, 94 mmol). After stirring for 1 h between 0 and 10° C., the reaction mixture was treated with aqueous sodium carbonate then extracted into toluene. The organic layer was washed with dilute aqueous hydrochloric acid, then concentrated in vacuo to give the title compound as a white solid.

e) (1S)-1-(2-Hydroxyethyl)-3,4-dihydro-1H-2-benzopyran-6-carbonitrile

A suspension of 2-((1S)-6-bromo-3,4-dihydro-1H-2-benzopyran-1-yl)ethanol (300 g, 1.17 mol), copper(I) cyanide (209 g, 2.34 mol), and copper(I) iodide (33.3 g, 0.18 mol) in dry DMF (1.16 L), under an atmosphere of nitrogen, was heated to 140° C. After 8 h at this temperature, HPLC analysis of an aliquot indicated that the reaction was complete. The reaction mixture was cooled to room temperature and poured into an aqueous solution of ethylenediamine (3 L, v/v 3/1) then extracted into toluene. The combined organic layers were washed with water and concentrated in vacuo to give the crude title compound. This material is used without further purification in the subsequent step.

f) (1S)-1-(2-Hydroxyethyl)-3,4-dihydro-1H-2-benzopyran-6-carboxamide

To a solution of crude (1S)-1-(2-hydroxyethyl)-3,4-dihydro-1H-2-benzopyran-6-carbonitrile (178 g, 0.88 mol) in methanol (460 mL) and DMSO (125 mL) was added potassium carbonate (13 g, 94 mmol). 35% hydrogen peroxide (102 mL) was then added dropwise while maintaining the temperature of the mixture below 50° C. The reaction mixture was then allowed to stir for 1 h at ambient temperature. Analysis of an aliquot by silica TLC (ethyl acetate) indicated that the reaction was complete. Water (130 mL) was added and methanol removed in vacuo. Water (800 mL) and 1N HCl (100 mL) were added and the mixture allowed to stir overnight. The solid was filtered, washed with water, and dried. Recrystallization from methyl(i-butyl)ketone gave the title compound.

Method B a) 2-((1S)-6-Bromo-3,4-dihydro-1H-2-benzopyran-1-yl-ethyl tert-butyl(dimethyl)silyl ether A 1M solution of tert-butyldimethylsilyl chloride in dichloromethane (30 mL, 30 mmol) was added dropwise under nitrogen to an ice/water-cooled solution of 2-((1S)-6-bromo-3,4-dihydro-1H-2-benzopyran-1-yl)ethanol (6.7 g, 24.4 mmol), diisopropylethylamine (6.7 g. 51.8 mmol) and dimethylaminopyridine (0.32 g, 2.5 mmol) in dry dimethylformamide (70 mL). After stirring overnight at room temperature, the mixture was quenched with ice/water and extracted with ether (2×). The combined organic extracts were washed with water (5×), dried (MgSO$_4$) and evaporated in vacuo to give an oil. This was purified by flash chromatography on silica, eluting with ethyl acetate/hexane (0:100 to 10:90), to give the title compound as oil.

b) (1S)-1-(2-{[tert-Butyl(dimethyl)silyl]oxy}ethyl)-3,4-dihydro-1H-2-benzopyran-6-carboxylic acid A 1.7M solution of tert-butyl lithium in pentane (1.75 mL, 2.97 mmol) was added under nitrogen to a solution of 2-((1S)-6-bromo-3,4-dihydro-1H-2-benzopyran-1-yl)ethyl tert-butyl(dimethyl)silyl ether (0.5 g, 1.35 mmol) in tetrahydrofuran (10 mL), maintained at −70° C. After stirring for 30 min, carbon dioxide was bubbled through the reaction mixture for 30 min. After stirring at room temperature overnight, saturated ammonium chloride in water was added and the product extracted into ethyl acetate. The organic extracts were dried (MgSO$_4$) and evaporated in vacuo to give an oil (0.57 g). This was purified by flash chromatography on silica, eluting with ethyl acetate/hexane (0:100 to 25:75) to give the title compound as a white solid.

c) (1S)-1-(2-{[tert-Butyl(dimethyl)silyl]oxy}ethyl)-3,4-dihydro-1H-2-benzopyran-6-carboxamide A solution of (1S)-1-(2-{[tert-butyl)dimethyl)silyl]oxy}ethyl)-3,4-dihydro-1H-2-benzopyran-6-carboxylic acid (20.7 g, 61.2 mmol) and 1,1'-cabonyldiimidazole (20 g, 123 mmol) in dry tetrahydrofuran (450 mL) was stirred under nitrogen at room temperature for 16 h. A 0.5M solution of ammonia in dioxane (620 mL, 310 mmol) was added and the mixture stirred at room temperature for 1 day. Water (1 L) was added and the product extracted into dichloromethane (2×1 L). The combined organic extracts were washed with saturated aqueous sodium bicarbonate (2×500 mL) and brine (2×50 mL), dried (MgSO$_4$) and evaporated in vacuo to give a solid (21 g). This was purified by flash chromatography on silica, eluting with hexane/ethyl acetate (1:1) then ethyl acetate to give the title compound.

d) (1S)-1-(2-Hydroxyethyl)-3,4-dihydro-1H-2-benzopyran-6-carboxamide (1S)-1-(2-{[tert-Butyl(dimethyl)silyl]oxy}ethyl)-3,4-dihydro-1H-2-benzopyran-6-carboxamide (1 g, 2.98 mmol) was dissolved in a mixture of acetic acid (10 mL) and water (5 mL), then stirred for 2 h. The solution was evaporated to give a residue that was dried in vacuo at 55° C. to give the title compound as a white solid.

2-[(1S)-6-(Aminocarbonyl)-3,4-dihydro-1H-2-benzopyran-1-yl]ethyl methanesulfonate (1S)-1-(2-Hydroxyethyl)-3,4-dihydro-1H-2-benzopyran-6-carboxamide (5 g, 22.6 mmol) was dissolved in a mixture of dry tetrahydrofuran (375 mL) and dry dimethylformamide (15 mL) with the aid of gentle heating. Triethylamine (4.6 g, 45.5 mmol) was added, followed by methanesulfonyl chloride (2.72 g, 23.8 mmol). The mixture was stirred under nitrogen at room temperature for 1 day. The reaction mixture was quenched with water (1000 mL) and the product extracted into ethyl acetate (2×500 mL). The combined organic extracts were washed with brine (2×500 mL), dried (MgSO$_4$), and evaporated in vacuo to give the crude product as a white solid (6.5 g, 97%). The solid was triturated with ether (300 mL) to give 2-[(1S)-6-(aminocarbonyl)-3,4-dihydro-1H-2-benzopyran-1-yl]ethyl methanesulfonate as a white solid.

(3R)-1-(6-Fluoro-1-naphthyl)-3-methylpiperazine a) 6-Fluoro-3,4-dihydro-1-naphthalenyl trifluoromethanesulfonate To a stirred solution of 6-fluoro-3,4-dihydro-1(2H)-naphthalenone (0.50 g, 3 mmol) in dry THF (25 mL) at −78° C. under nitrogen was added lithium bis(trimethylsilyl)amide (1M in THF) (3.6 mL, 3.6 mmol) over 5 min. The solution was stirred for 1 h, then N-phenyltrifluoromethanesulfonimide (1.3 g, 3.6 mmol) was added in one portion and the reaction mixture allowed to warm to room temperature. Stirring was continued for 2 h, then the solvent was removed in vacuo. The residue was dissolved in ethyl acetate and washed with 2M sodium hydroxide, water, and then brine. The organic extracts were dried (MgSO$_4$), and concentrated in vacuo. The resultant red oil was purified by column chromatography on silica, eluting with ethyl acetate/hexane (1:9), to yield 6-fluoro-3,4-dihydro-1-naphthalenyl trifluoromethane sulfonate as a colourless oil.

b) 6-Fluoro-1-naphthyl trifluoromethanesulfonate

To a solution of 6-fluoro-3,4-dihydro-1-naphthalenyl trifluoromethane sulfonate (0.77 g, 2.8 mmol) in dioxan (15 mL) was added 2,3-dichloro-5,6-dicyano-1,4-benzoquinone (0.95 g, 4.2 mmol) and the reaction mixture heated under reflux for 18 h. The solvent was removed in vacuo and the crude product purified by column chromatography on silica, eluting with hexane, to yield 6-fluoro-1-naphthyl trifluoromethanesulfonate as a white solid.

c) (3R)-1-(6-Fluoro-1-naphthyl)-3-methylpiperazine

To a solution of 6-fluoro-1-naphthyl trifluoromethanesulfonate (0.29 g, 1 mmol) in toluene (2 mL) under nitrogen was added (2R)-methylpiperazine (0.10 g, 1.2 mmol), (R)-2,2'-bis(diphenylphosphino)-1,1'-binaphthyl (47 mg, 0.075 mmol), palladium(II) acetate (11 mg, 0.05 mmol) and caesium carbonate (0.46 g, 1.4 mmol). The resulting suspension was heated at 110° C. for 16 h. Upon cooling, the mixture was filtered through a short celite pad (washing with ethyl acetate), the filtrate concentrated in vacuo and the crude product purified by flash column chromatography on silica gel, eluting with dichloromethane/methanol (7:3), to yield (3R)-1-(6-fluoro-1-naphthyl)-3-methylpiperazine as a brown oil.

(3R)-1-(6-Cyano-1-naphthyl)-3-methylpiperazine a) 5-Bromo-2-naphthonitrile

To a solution of 5-bromo-2-naphthoic acid (4.3 g, 17 mmol)) in dry pyridine (75 mL) at 0° C. was added methanesulfonyl chloride (1.4 mL, 18 mmol). After stirring at 0° C. for 1 h, ammonia gas was bubbled through the solution for 10 min, whilst maintaining the temperature below 5° C. During the gas addition the solution became viscous, so additional dry pyridine (~30 mL) was added. Excess ammonia was removed in vacuo, the solution again cooled to 0° C., then treated with additional methanesulfonyl chloride (12.5 mL) and allowed to warm to room temperature overnight. The solution was poured onto ice cold water, the mixture stirred for 30 min and the brown precipitate collected by filtration, washed on the sinter with ice cold water, then dried in vacuo. The crude product was dissolved in hot chloroform (~35 mL) and insoluble material filtered off. The chloroform was removed and the residue dissolved in a minimum volume of ether at reflux. Hexane was added until the solution remained turbid at reflux, the solution filtered rapidly into a pre-heated flask, and allowed to cool slowly to room temperature. The precipitate was collected by filtration, washed with hexane, and dried in vacuo, to yield 5-bromo-2-naphthonitrile. Further crops were obtained by cooling the filtrate at −18° C. overnight.

b) (3R)-1-(6-Cyano-1-naphthyl)-3-methylpiperazine

To a solution of 5-bromo-2-naphthonitrile (0.47 g, 2 mmol) in dry toluene (30 mL) was added tris(dibenzylideneacetone)dipalladium(0) (40 mg), (R)-2,2'-bis(diphenylphosphino)-1,1'-binaphthyl (82 mg), (2R)-methylpiperazine (0.24 g, 2.4 mmol) and sodium tert-butoxide (0.27 g, 2.8 mmol). The solution was evacuated until bubbling started, then the atmosphere replaced with nitrogen. This purging and evacuation procedure was repeated for 15 min, then the mixture heated under reflux for 8 h. The reaction mixture was cooled to room temperature, diluted with ethyl acetate and filtered through celite. The filtrate was washed with aqueous ammonia, dried (MgSO$_4$), filtered and evaporated in vacuo. The residue was dissolved in methanol (10 mL) and applied to an activated SCX cartridge (10 g). The cartridge was washed with methanol (100 mL), then the product isolated by elution with 2M ammonia in methanol (50 mL). The solvent was removed in vacuo and further purified by flash chromatography on silica, eluting with acetone, to yield (3R)-1-(6-cyano-1-naphthyl)-3-methylpiperazine.

(3R)-1-(6-Cyano-1-benzothien-3-yl)-3-methylpiperazine a) 3-Bromo-1-benzothiophene-6-carbonitrile
To a solution of 1-benzothiophene-6-carbonitrile (2.13 g, 13.4 mmol) in dry DMF (20 mL) at −10° C. was added freshly recrystallised N-bromosuccinimide (2.38 g, 13.4 mmol). The solution was allowed to warm to room temperature and stirred over the weekend. The mixture was diluted with water and extracted into diethyl ether, and the organic extract washed with water, then brine. The extracts were dried ($MgSO_4$), filtered and evaporated in vacuo. The crude product was purified by flash chromatography on silica, eluting with ethyl acetate/hexane (1:9), to yield the title compound as a white solid.

b) (3R)-1-(6-Cyano-1-benzothien-3-yl)-3-methylpiperazine
3-Bromo-1-benzothiophene-6-carbonitrile was coupled with (2R)-methylpiperazine, as described above for (3R)-1-(6-cyano-1-naphthyl)-3-methylpiperazine, to yield (3R)-1-(6-cyano-1-benzothien-3-yl)-3-methylpiperazine.

EXAMPLE 1

(1S)-1-{2-[(2R)-4-(1,2-Dihydro-5-acenaphthylenyl)-2-methylpiperazinyl]ethyl}-3,4-dihydro-1H-2-benzopyran-6-carboxamide a) (3R)-1-(1,2-Dihydro-5-acenaphthylenyl)-3-methylpiperazine
A mixture of 2-(R)-methylpiperazine (0.124 g, 1.1 mmol), tris(dibenzylideneacetone)dipalladium(0) (49 mg, 0.05 mmol), rac-2,2'-bis(diphenylphosphino)-1,1'-binaphthyl (69 mg, 0.10 mmol) and sodium tert-butoxide (0.148 g, 1.5 mmol) were stirred in toluene (50 mL) under nitrogen for 15 min to give a blood red solution. 5-Bromo-1,2-dihydroacenaphthylene (0.256 g, 1.1 mmol) was added, the solution stirred under nitrogen and heated at reflux for 3 h. The mixture was cooled, diluted with dichloromethane and filtered through celite. The organic phase was washed with water, dried ($MgSO_4$), filtered and evaporated in vacuo. The crude product was taken forward to the next step without further purification.

b) (1S)-1-{2-[(2R)-4-(1,2-Dihydro-5-acenaphthylenyl)-2-methylpiperazinyl]ethyl}-3,4-dihydro-1H-2-benzopyran-6-carboxamide
(3R)-1-(1,2-Dihydro-5-acenaphthylenyl)-3-methylpiperazine (0.138 g, 0.55 mmol), 2-[(1S)-6-(aminocarbonyl)-3,4-dihydro-1H-2-benzopyran-1-yl]ethyl methanesulfonate (0.15 g, 0.50 mmol), potassium carbonate (0.138 g, 1.0 mmol), potassium iodide (0.083 g, 1.0 mmol) and acetonitrile (50 mL) were heated under reflux for 1 day with stirring under nitrogen. After cooling to room temperature, the inorganics were filtered off and the solvent evaporated in vacuo. The crude product was purified by preparative LC-MS to give the title compound. M+H=456.

The following Examples were prepared by substituting the (2R)-methylpiperazine in the above Example with alternative piperazines or homopiperazine, as indicated below:

EXAMPLE 2

(1S)-1-{2-[(2R)-4-(1,2-Dihydro-5-acenaphthylenyl)-2-ethylpiperazinyl]ethyl}-3,4-dihydro-1H-2-benzopyran-6-carboxamide Prepared from 5-bromo-1,2-dihydro-acenaphthylene and (2R)-ethylpiperazine. M+H=470.

EXAMPLE 3

(1S)-1-{2-[(2S)-4-(1,2-Dihydro-5-acenaphthylenyl)-2-ethylpiperazinyl]ethyl}-3,4-dihydro-1H-2-benzopyran-6-carboxamide Prepared from 5-bromo-1,2-dihydro-acenaphthylene and (2S)-ethylpiperazine. M+H=470.

EXAMPLE 4

(1S)-1-{2-[4-(1,2-Dihydro-5-acenaphthylenyl)hexahydro-1H-1,4-diazepin-1-yl]ethyl}-3,4-dihydro-1H-2-benzopyran-6-carboxamide Prepared from 5-bromo-1,2-dihydro-acenaphthylene and homopiperazine. M+H=456.

EXAMPLE 5

(1S)-1-{2-[(2R)-4-(5-Acenaphthylenyl)-2-methylpiperazinyl]ethyl}-3,4-dihydro-1H-2-benzopyran-6-carboxamide a) 5-Bromoacenaphthylene
To 5-bromo-1,2-dihydroacenaphthalene (0.10 g, 0.43 mmol) in dichloromethane (10 mL) was added 2,3-dichloro-5,6-dicyano-1,4-benzoquinone (0.117 g, 0.515 mmol) and stirred at room temperature for 1 day. An additional portion of DDQ (0.10 g) was added and the reaction stirred for a further 1 day. The mixture was washed with water and the organic phase dried ($MgSO_4$), filtered and evaporated in vacuo. The crude product was purified by flash chromatography on silica, eluting with ethyl acetate/heptane (0:10 to 1:9), to yield the title compound.

b) (3R)-1-(5-Acenaphthylenyl)-3-methylpiperazine
5-Bromoacenaphthylene was coupled with (2R)-methylpiperazine, as described for Example 1a).

c) (1S)-1-{2-[(2R)-4-(5-Acenaphthylenyl)-2-methylpiperazinyl]ethyl}-3,4-dihydro-1H-2-benzopyran-6-carboxamide
(3R)-1-(5-Acenaphthylenyl)-3-methylpiperazine was condensed with 2-[(1S)-6-(aminocarbonyl)-3,4-dihydro-1H-2-benzopyran-1-yl]ethyl methanesulfonate, as described for Example 1b), to yield the title compound. M+H=454.

EXAMPLE 6

(1S)-1-{2-[(2R)-4-(1-Oxo-1,2-dihydro-5-acenaphthylenyl)-2-methylpiperazinyl]ethyl}-3,4-dihydro-1H-2-benzopyran-6-carboxamide a) 5-Bromo-1,2-dihydro-1-acenaphthylenol
To 1,2-dihydro-1-acenaphthylenol (0.34 g, 2 mmol) in dry DMF (10 mL) was added recrystallised N-bromosuccinimide (0.39 g, 2.2 mmol), and the mixture stirred for 3 h under nitrogen. The solution was poured onto water (500 mL) and the precipitate filtered off. The resultant solid was redissolved in methanol, filtered and evaporated in vacuo to yield the title compound as a brown solid.

b) [(5-Bromo-1,2-dihydro-1-acenaphthylenyl)oxy](tert-butyl)diphenylsilane

To 5-bromo-1,2-dihydro-1-acenaphthylenol (0.25 g, 1 mmol) in dry THF (30 mL) was added chloro(tert-butyl)diphenylsilane (0.275 g, 1 mmol) and imidazole (0.34 g, 5 mmol), and the reaction stirred at room temperature under nitrogen for 18 h. The mixture was diluted with diethyl ether, filtered through a pad of silica, and evaporated in vacuo. Purification by flash chromatography on silica, eluting with ethyl acetate/hexane (1:9 to 1:1), yielded the title compound as a colourless oil.

c) (3R)-1-(1-{[tert-Butyl(diphenyl)silyl]oxy}-1,2-dihydro-5-acenaphthylenyl)-3-methylpiperazine

[(5-Bromo-1,2-dihydro-1-acenaphthylenyl)oxy](tert-butyl)diphenylsilane was coupled with (2R)-methylpiperazine, as described for Example 1a).

d) (1S)-1-{2-[(2R)-4-(1-{[tert-Butyl(diphenyl)silyl]-oxy}-1,2-dihydro-5-acenaphthylenyl)-2-methyl-piperazinyl]ethyl}-3,4-dihydro-1H-2-benzopyran-6-carboxamide (3R)-1-(1-{[tert-Butyl(diphenyl)silyl]oxy}-1,2-dihydro-5-acenaphthylenyl)-3-methylpiperazine was condensed with 2-[(1S)-6-(aminocarbonyl)-3,4-dihydro-1H-2-benzopyran-1-yl]ethyl methanesulfonate, as described for Example 1b).

e) (1S)-1-{2-[(2R)-4-(1-Hydroxy-1,2-dihydro-5-acenaphthylenyl)-2-methylpiperazinyl]ethyl}-3,4-dihydro-1H-2-benzopyran-6-carboxamide To a solution of (1S)-1-{2-[(2R)-4-(1-{[tert-butyl(diphenyl)silyl]oxy}-1,2-dihydro-5-acenaphthylenyl)-2-methylpiperazinyl]ethyl}-3,4-dihydro-1H-2-benzopyran-6-carboxamide (1.72 g, 2.43 mmol) in dry THF (70 mL) was slowly added tetrabutylammonium fluoride (1M solution in THF) (2.9 mL, 2.92 mmol), and the mixture stirred for 18 h at room temperature. Dichloromethane was added to the reaction, which was then washed with water. The combined organic phases were dried (MgSO$_4$), filtered and evaporated in vacuo to yield a brown oil. The residue was dissolved in methanol and applied to an activated SCX-2 ion exchange cartridge. The cartridge was washed with methanol, then the product isolated by elution with 2M ammonia in methanol. The solvent was removed in vacuo and the crude product further purified by preparative LC-MS, to yield the title compound.

f) (1S)-1-{2-[(2R)-2-Methyl-4-(1-oxo-1,2-dihydro-5-acenaphthylenyl)piperazinyl]ethyl}-3,4-dihydro-1H-2-benzopyran-6-carboxamide To a solution of (1S)-1-{2-[(2R)-4-(1-hydroxy-1,2-dihydro-5-acenaphthylenyl)-2-methylpiperazinyl]ethyl}-3,4-dihydro-1H-2-benzopyran-6-carboxamide (0.10 g, 0.21 mmol) in dry DMF (2 mL), cooled to 0° C. under nitrogen, was added pyridinium dichromate (0.08 g, 0.21 mmol), and the mixture stirred for 4 h, allowing the reaction to warm to room temperature. A further equivalent of pyridinium dichromate was added and the reaction stirred for a further 1 h. The mixture was poured onto water and the resultant precipitate filtered off. Purification by preparative LC-MS yielded (1S)-1-{2-[(2R)-2-methyl-4-(1-oxo-1,2-dihydro-5-acenaphthylenyl)piperazinyl]ethyl}-3,4-dihydro-1H-2-benzopyran-6-carboxamide. M+H=470.

EXAMPLE 7

(1S)-1-{2-[(2R)-2-Methyl-4-(1H,3H-naphtho[1,8-cd]pyran-6-yl)piperazinyl]ethyl}-3,4-dihydro-1H-2-benzopyran-6-carboxamide a) 6-Bromo-1H,3H-naphtho[1,8-cd]pyran To 6-bromo-1H,3H-naphtho[1,8-cd]pyran-1,3-dione (1.5 g, 5.4 mmol) in ethanol (10 mL) was added sodium borohydride (0.41 g, 10.8 mmol) and the mixture stirred at room temperature for 1 h. The reaction was quenched with 3M hydrochloric acid and extracted into dichloromethane. The combined organic extracts were dried (Na$_2$SO$_4$) and concentrated in vacuo. The residue was dissolved in dichloromethane and trifluoroacetic acid (1.05 mL, 13.53 mmol) and triethylsilane (4.3 mL, 27 mmol) added. After stirring for 5 min at room temperature, the solvent was removed in vacuo and the residue purified by column chromatography on silica gel, eluting with dichloromethane, to yield 6-bromo-1H,3H-naphtho[1,8-cd]pyran as a white solid.

b) (3R)-3-Methyl-1-(1H,3H-naphtho[1,8-cd]pyran-6-yl)piperazine

A mixture of 6-bromo-1H,3H-naphtho[1,8-cd]pyran (0.30 g, 1.2 mmol), 2-(R)-methylpiperazine (0.145 g, 1.44 mmol), tris(dibenzylideneacetone)dipalladium(0) (55 mg, 0.06 mmol), rac-2,2'-bis(diphenylphosphino)-1,1'-binaphthyl (56 mg, 0.09 mmol) and sodium tert-butoxide (0.162 g, 1.68 mmol) in toluene (5 mL) was heated under reflux for 2 h. The solvent was evaporated in vacuo and the crude mixture purified by column chromatography on silica gel, eluting with dichloromethane/methanol (9:1), to yield (3R)-3-methyl-1-(1H,3H-naphtho[1,8-cd]pyran-6-yl)piperazine as an orange solid.

c) (1S)-1-{2-[(2R)-2-Methyl-4-(1H,3H-naphtho[1,8-cd]pyran-6-yl)piperazinyl]ethyl}-3,4-dihydro-1H-2-benzopyran-6-carboxamide (3R)-3-Methyl-1-(1H,3H-naphtho[1,8-cd]pyran-6-yl)piperazine was coupled with 2-[(1S)-6-aminocarbonyl)-3,4-dihydro-1H-2-benzopyran-1-yl]ethyl methanesulfonate as described for Example 1b), to yield (1S)-1-{2-[(2R)-2-methyl-4-(1H,3H-naphtho[1,8-cd]pyran-6-yl)piperazinyl]ethyl}-3,4-dihydro-1H-2-benzopyran-6-carboxamide. M+H=472.

EXAMPLE 8

(1S)-1-{2-[(2R)-2-Methyl-4-(1H,3H-naphtho[1,8-cd]thiopyran-6-yl)piperazinyl]ethyl}-3,4-dihydro-1H-2-benzopyran-6-carboxamide a) 6-Bromo-1H,3H-naphtho[1,8-cd]thiopyran A mixture of 1-bromo-4,5-bis(bromomethyl)-naphthalene (0.38 g, 0.97 mmol) and sodium sulfide nonahydrate (0.25 g, 1.04 mmol) in dimethylformamide (13 mL) was stirred at room temperature for 5 h, in the presence of sodium sulfate as scavenger for the water. The reaction mixture was poured into water and extracted into diethyl ether. The combined organic extracts were washed with water, dried (Na$_2$SO$_4$) and concentrated to dryness, to yield 6-bromo-1H,3H-naphtho[1,8-cd]thiopyran as a pale yellow solid.

b) (3R)-3-Methyl-1-(1H,3H-naphtho[1,8-cd]thiopyran-6-yl) piperazine

The procedure used for the synthesis of (3R)-3-methyl-1-(1H,3H-naphtho[1,8-cd]pyran-6-yl)piperazine (Example 5b)) was followed, using 6-bromo-1H,3H-naphtho[1,8-cd]thiopyran as starting material and making non-critical variations, to obtain the title compound (3R)-3-methyl-1-(1H,3H-naphtho[1,8-cd]thiopyran-6-yl)piperazine as brown solid.

c) (1S)-1-{2-[(2R)-2-Methyl-4-(1H,3H-naphtho[1,8-cd]thiopyran-6-yl)piperazinyl]ethyl}-3,4-dihydro-1H-2-benzopyran-6-carboxamide (3R)-3-Methyl-1-(1H,3H-naphtho[1,8-cd]thiopyran-6-yl)piperazine was coupled with 2-[(1S)-6-aminocarbonyl)-3,4-dihydro-1H-2-benzopyran-1-yl]ethyl methanesulfonate as described for Example 1b), to yield (1S)-1-{2-[(2R)-2-methyl-4-(1H,3H-naphtho[1,8-cd]thiopyran-6-yl)piperazinyl]ethyl}-3,4-dihydro-1H-2-benzopyran-6-carboxamide. M+H=488.

EXAMPLE 9

(1S)-1-{2-[4-(1,2-Dihydro-5-acenaphthylenyl)-1-piperidinyl]ethyl}-3,4-dihydro-1H-2-benzopyran-6-carboxamide a) tert-Butyl 4-(1,2-dihydro-5-acenaphthylenyl)-4-hydroxy-1-piperidinecarboxylate To a solution of 5-bromoacenaphthylene (1.00 g, 4.29 mmol) in dry THF (20 mL), under nitrogen at −78° C., was added a solution of n-butyllithium (2.5M in hexanes) (1.89 mL, 4.72 mmol) over a period of 30 min. The resulting deep red solution was left to stir for a further 30 minutes at −78° C. A solution of tert-butyl 4-oxo-1-piperidinecarboxylate (0.94 g, 4.72 mmol) in dry THF (10 mL) was then added over 30 min. After 2.5 h a cooled solution of saturated ammonium chloride (30 mL) was added, the reaction mixture allowed to warm to room temperature and then extracted with diethyl ether. The combined organic extracts were dried ($Na_2SO_4$) and concentrated in vacuo to yield a thick, yellowish tan oil. This oil was purified by flash chromatography on silica, eluting with a methanol/dichloromethane gradient, to yield tert-butyl 4-(1,2-dihydro-5-acenaphthylenyl)-4-hydroxy-1-piperidinecarboxylate as a sticky yellow residue.

b) 4-(1,2-Dihydro-5-acenaphthylenyl)piperidine

To a solution of tert-butyl 4-(1,2-dihydro-5-acenaphthylenyl)-4-hydroxy-1-piperidinecarboxylate (0.44 g, 1.24 mmol) in dichloromethane (4 mL) was added triethylsilane (1.10 mL, 6.22 mmol) under nitrogen. The mixture was cooled to −30° C. then trifluoroacetic acid (0.48 mL, 6.22 mmol) added dropwise, maintaining the temperature below −25° C. After 2.5 h, the reaction mixture was allowed to warm to 0° C. and additional trifluoroacetic acid (0.48 mL, 6.22 mmol) added over 5 min. The reaction mixture was allowed to warm to room temperature and left to stir for 3 days. Ice was then added to the reaction mixture, followed by potassium hydroxide to a pH of 14, and the resultant slurry extracted with dichloromethane. The combined organic extracts were dried ($Na_2SO_4$) and concentrated in vacuo to yield a yellow oil. The oil was dissolved in methanol and loaded onto an SCX-2 column. The column was washed with methanol, then a 2N solution of ammonia in methanol. Concentration in vacuo of the ammonia solution yielded 4-(1,2-dihydro-5-acenaphthylenyl)piperidine as a pale yellow oil.

c) (1S)-1-{2-[4-(1,2-Dihydro-5-acenaphthylenyl)-1-piperidinyl]ethyl}-3,4-dihydro-1H-2-benzopyran-6-carboxamide 4-(1,2-Dihydro-5-acenaphthylenyl)piperidine was coupled with 2-[(1S)-6-aminocarbonyl)-3,4-dihydro-1H-2-benzopyran-1-yl]ethyl methanesulfonate, as described for Example 1b), to yield (1S)-1-{2-[4-(1,2-dihydro-5-acenaphthylenyl)-1-piperidinyl]ethyl}-3,4-dihydro-1H-2-benzopyran-6-carboxamide as a pale yellow oil. M+H=441.

EXAMPLE 10

(1S)-1-{2-[(2R)-4-(1,2-Dihydro-5-acenaphthylenyl)-2-methylpiperazinyl]ethyl}-1,3-dihydro-2-benzofuran-5-carboxamide a) 5-Chloro-1,3-dihydro-2-benzofuran-1-ol To a solution of 5-chlorophthalide (3.64 g, 21.6 mmol) in dichloromethane (100 mL) at −78° C. was added di-isobutylaluminium hydride (1M in toluene) (23.8 mL, 23.8 mmol) dropwise. After 1 h the reaction mixture was quenched with a saturated solution of sodium tartrate (250 mL), allowed to warm to room temperature and stirred for 1 h. The layers were separated and the aqueous layer extracted with dichloromethane. The combined organic layers were dried ($MgSO_4$), filtered and concentrated in vacuo to yield the title compound as a white solid.

b) Ethyl (5-chloro-1,3-dihydro-2-benzofuran-1-yl)acetate

5-Chloro-1,3-dihydro-2-benzofuran-1-ol (2.95 g, 17.3 mmol) was dissolved in THF (60 mL) and cooled to 0° C. Triethyl phosphonoacetate (11.7 g, 52.1 mmol) and caesium carbonate (17 g, 52.1 mmol) were added. After 20 min the cold bath was removed and the reaction mixture allowed to stir at room temperature for 3 h, then quenched with a saturated solution of ammonium chloride and extracted with ethyl acetate. The combined organic layers were washed with brine, dried ($MgSO_4$), filtered and evaporated in vacuo. Purification by column chromatography, eluting with ethyl acetate/hexane (1:4), yielded the title compound as a colourless oil.

c) 2-(5-Chloro-1,3-dihydro-2-benzofuran-1-yl)ethanol

Ethyl (5-chloro-1,3-dihydro-2-benzofuran-1-yl)-acetate (2.79 g, 11.6 mmol) in THF (60 mL) was cooled to −78° C. and di-isobutylaluminium hydride (1M in toluene) (12.7 mL, 12.7 mmol) was added dropwise. After 1 h, the reaction mixture was quenched with a saturated solution of sodium tartrate (150 mL), allowed to warm to room temperature and stirred for 1 h. The layers were separated and the aqueous layer extracted with ethyl acetate. The combined organic layers were dried ($MgSO_4$), filtered and evaporated in vacuo. The resultant crude intermediate was dissolved in methanol (50 mL), cooled to 0° C., and sodium borohydride (0.48 g, 12.7 mmol) added in portions. The reaction was quenched with saturated sodium hydrogen carbonate and extracted with ethyl acetate. The combined organic layers were washed with brine, dried ($MgSO_4$), filtered and evaporated in vacuo. The crude product was purified by column chromatography, eluting with ethyl acetate/hexane (1:2), to yield the title compound as a white solid.

d) tert-Butyl-[2-(5-chloro-1,3-dihydro-2-benzofuran-1-yl)ethoxy]dimethylsilane

Prepared from 2-(5-chloro-1,3-dihydro-2-benzofuran-1-yl)ethanol, as described for the preparation of 2-((1S)-6-bromo-3,4-dihydro-1H-2-benzopyran-1-yl)ethyl tert-butyl (dimethyl)silyl ether, to yield tert-butyl-[2-(5-chloro-1,3-dihydro-2-benzofuran-1-yl)ethoxy]-dimethylsilane.

e) 1-[2-(tert-Butyldimethylsilanoxy)-ethyl]-1,3-dihydro-2-benzofuran-5-carboxamide A solution of tert-butyl-[2-(5-chloro-1,3-dihydro-2-benzofuran-1-yl)-ethoxy]dimethylsilane (0.94 g, 1.48 mmol) in dioxan (2 mL) and a solution of tri-tert-butylphosphine (89 mg, 0.44 mmol) in dioxan (0.7 mL) were added dropwise to a round bottom flask charged with tris(dibenzylideneacetone)dipalladium (136 mg, 0.148 mmol) and zinc cyanide (0.208 g, 1.78 mmol). The flask was fitted with a reflux condenser and the resulting red-purple suspension heated at 120° C. under nitrogen. After 16 h the reaction mixture was cooled to room temperature and diluted with ethyl acetate, filtered through a pad of celite and concentrated in vacuo. The crude product was purified by chromatography on silica, eluting with hexane/ethyl acetate (10:1), to yield the title compound contaminated with dibenzylideneacetone. This crude mixture was dissolved in dichloromethane (3 mL), and tetrabutylammonium hydrogen sulfate (0.29 mmol) was added in one portion. Hydrogen peroxide (30% w/v aqueous solution) (5.75 mmol) and sodium hydroxide (2N aqueous solution) (1.15 mL, 2.3 mmol) were added dropwise. The resulting reaction mixture was sonicated for 1 h, then quenched with potassium hydrogen sulfate (4 mL), diluted with dichloromethane, and the layers separated. The organic layer was washed with an aqueous solution of sodium sulfite, dried ($MgSO_4$), filtered and evaporated in vacuo. The crude product was purified by chromatography on silica, eluting with ethyl acetate/hexane (1:1), to yield the title compound as a white solid.

f) 1-(2-Hydroxyethyl)-1,3-dihydro-2-benzofuran-5-carboxamide

Prepared from 1-[2-(tert-butyldimethylsilanoxy)-ethyl]-1,3-dihydro-2-benzofuran-5-carboxamide, as described for the preparation of (1S)-1-(2-hydroxyethyl)-3,4-dihydro-1H-2-benzopyran-6-carboxamide.

g) (1S)1-{2-[(2R)-4-(1,2-Dihydro-5-acenaphthylenyl)-2-methylpiperazinyl]ethyl}-1,3-dihydro-2-benzofuran-5-carboxamide The title compound was prepared from 1-(2-hydroxyethyl)-1,3-dihydro-2-benzofuran-5-carboxamide by initial formation of the methanesulfonate as described for the preparation of 2-[(1S)-6-(aminocarbonyl)-3,4-dihydro-1H-2-benzopyran-1-yl]ethyl methanesulfonate, and condensation of this sulfonate with (3R)-1-(1,2-dihydro-5-acenaphthylenyl)-3-methylpiperazine, as described for Example 1b). The mixture of diastereomers was separated by chiral HPLC using a Chiracel OJ column, eluting with hexane/ethanol (1:1) with 0.2% dimethylethylamine. M+H=442.

EXAMPLE 11

1-{2-[4-(1,2-Dihydro-5-acenaphthylenyl)hexahydro-1H-1,4-diazepin-1-yl]ethyl}-1,3-dihydro-2-benzofuran-5-carboxamide a) (−)-(5-Chloro-1,3-dihydro-2-benzofuran-1-yl)acetic acid (±/−)-Ethyl (5-chloro-1,3-dihydro-2-benzofuran-1-yl)acetate (6.1 g, 25.3 mmol) and Amano Lipase P30 (3.8 g) were suspended in pH 7.0 buffer solution (150 mL) and the mixture was vigorously stirred for 24 h. The suspension was then filtered through a pad of celite, and the filter pad washed with water, hydrochloric acid (1M) and several times with ethyl acetate. The aqueous layer was separated and washed twice with ethyl acetate. The combined organic phase was then extracted with saturated aqueous sodium bicarbonate (3×150 mL), dried over magnesium sulphate, filtered and evaporated under reduced pressure to give a pale yellow oil, (+)-ethyl(5-chloro-1,3-dihydro-2-benzofuran-1-yl)acetate (95% ee by chiral HPLC)—this could be recycled by base catalysed racemisation, as described below.

The aqueous bicarbonate layer was then acidified with hydrochloric acid (1N), extracted with dichloromethane (3×), dried ($MgSO_4$), filtered and evaporated in vacuo to give a white crystalline solid. (95% ee by chiral HPLC). The solid was recrystallized from hexane-ether to provide the title acid (>98% ee).

b) (−)-2-(5-Chloro-1,3-dihydro-2-benzofuran-1-yl)ethanol (5-Chloro-1,3-dihydro-2-benzofuran-1-yl)acetic acid (1.91 g, 9.0 mmol) was dissolved in dry THF (8 mL) under nitrogen and cooled to 0° C. Borane-dimethylsulfide complex (0.155 mL, 1.64 mmol) was added by syringe. After 1 h the cooling bath was removed and the solution was stirred at room temperature for 2 h. The solution was partitioned between saturated aqueous sodium hydrogen carbonate and diethyl ether. The aqueous layer was further extracted with ether, and the combined organic layers washed with brine, dried ($MgSO_4$), filtered and concentrated in vacuo. This yielded the title compound as a white solid (>98% ee by chiral HPLC).

c) (±)-Ethyl (5-chloro-1,3-dihydro-2-benzofuran-1-yl)acetate (+)-Ethyl (5-chloro-1,3-dihydro-2-benzofuran-1-yl)acetate (95% ee) (185 mg, 0.77 mmol) was dissolved in dry ethanol (8 mL) under nitrogen. Sodium ethoxide (5 mg, 0.07 mmol) was added in one portion and the reaction stirred at room temperature overnight. The solvent was removed in vacuo and the residue partitioned between water and dichloromethane. The organic layer was washed with brine, dried ($MgSO_4$), filtered and concentrated in vacuo to provide the title compound as a yellow oil.

d) (−)-2-[(5-Aminocarbonyl)-1,3-dihydro-2-benzofuran-1-yl]ethyl methanesulfonate Prepared from (−)-2-(5-chloro-1,3-dihydro-2-benzofuran-1-yl)ethanol, as described in Example 10 with the corresponding racemic alcohol.

e) (−)-1-{2-[4-(1,2-Dihydro-5-acenaphthylenyl)hexahydro-1H-1,4-diazepin-1-yl]ethyl}-1,3-dihydro-2-benzofuran-5-carboxamide Prepared from 1-(1,2-dihydro-5-acenaphthylenyl)-hexahydro-1H-1,4-diazepine and (−)-2-[(5-aminocarbonyl)-1,3-dihydro-2-benzofuran-1-yl]ethyl methanesulfonate, as described for Example 8. M+H=442.

EXAMPLE 12

1-({2-[(2R)-4-(6-Fluoro-1-naphthyl)-2-methylpiperazinyl]ethyl}-3,4-dihydro-1H-2-benzopyran-6-yl) methanamine a) 1-(2-Hydroxyethyl)-3,4-dihydro-1H-2-benzopyran-6-carbonitrile 2-(6-Bromo-3,4-dihydro-1H-2-benzopyran-1-yl)ethanol (1.3 g, 5.1 mmol), zinc cyanide (0.36 g, 3 mmol) and tetrakis(triphenylphosphine)palladium (0) (0.23 g, 0.20 mmol) were stirred in degassed DMF (20 mL) under nitrogen at reflux for 9 h. The reaction mixture was diluted with toluene and washed with 2M aqueous ammonia, the aqueous layer further extracted with ethyl acetate, then the combined organic extracts washed with brine. The organic extracts were dried ($MgSO_4$), filtered and evaporated in vacuo. Purification by flash chromatography on silica, eluting with ethyl acetate/hexane (30:70 to 0:100), yielded the title compound as a light brown oil.

b) 2-(6-Cyano-3,4-dihydro-1H-2-benzopyran-1-yl)ethyl methanesulfonate

Prepared from 1-(2-hydroxyethyl)-3,4-dihydro-1H-2-benzopyran-6-carbonitrile, as described for the preparation of 2-[(1S)-6-(aminocarbonyl)-3,4-dihydro-1H-2-benzopyran-1-yl]ethyl methanesulfonate.

c) 1-{2-[(2R)-4-(6-Fluoro-1-naphthyl)-2-methylpiperazinyl]ethyl}-3,4-dihydro-1H-2-benzopyran-6-carbonitrile Prepared by condensation of 2-(6-cyano-3,4-dihydro-1H-2-benzopyran-1-yl)ethyl methanesulfonate with (3R)-1-(6-Fluoro-1-naphthyl)-3-methylpiperazine, as described for Example 1b).

d) 1-{2-[(2R)-4-(6-Fluoro-1-naphthyl)-2-methylpiperazinyl]ethyl}-3,4-dihydro-1H-2-benzopyran-6-yl)methanamine To a stirred solution of 1-{2-[(2R)-4-(6-fluoro-1-naphthyl)-2-methyl-piperazinyl]ethyl}-3,4-dihydro-1H-2-benzopyran-6-carbonitrile (0.50 g, 1.2 mmol) in dry THF (4 mL) was added lithium aluminium hydride (1M solution in THF) (1.4 mL, 1.4 mmol) and the mixture stirred overnight at room temperature. The reaction was quenched by cautious addition of 2M sodium hydroxide, then extracted into chloroform. The combined organic extracts were dried ($MgSO_4$), filtered and evaporated in vacuo. The crude product was purified by preparative LC-MS to yield the title compound as a yellow oil. M+H=480.

EXAMPLE 13

1-({2-[(2R)-4-(6-Fluoro-1-naphthyl)-2-methylpiperazinyl]ethyl}-3,4-dihydro-1H-2-benzopyran-6-yl)methylformamide To a stirred solution of 1-{2-[(2R)-4-(6-fluoro-1-naphthyl)-2-methylpiperazinyl]ethyl}-3,4-dihydro-1H-2-benzopyran-6-yl)methanamine (0.234 g, 0.53 mmol) in dry DMF (10 mL) was added formic acid (27 mg, 0.59 mmol), and the reaction mixture heated at reflux for 1 h under nitrogen. The mixture was diluted with dichloromethane and washed three times with water, then aqueous sodium hydrogen carbonate, dried ($MgSO_4$), filtered and evaporated in vacuo. The crude product was purified by preparative LC-MS to yield the title compound as a beige solid. M+H=508.

EXAMPLE 14

N-[((1S)-1-{2-[(2R)-4-(6-Fluoro-1-naphthyl)-2-methylpiperazinyl]ethyl}-3,4-dihydro-1H-2-benzopyran-6-yl)methyl]acetamide a) 1-(2-Oxoethyl)-3,4-dihydro-1H-2-benzopyran-6-carbonitrile Dimethylsulfoxide (0.35 mL, 5 mmol) and oxalyl chloride (2M in dichloromethane) (2.2 mL, 4.4 mmol) were stirred in dichloromethane (30 mL) under nitrogen at −78° C. After 10 min, 1-(2-hydroxyethyl)-3,4-dihydro-1H-2-benzopyran-6-carbonitrile (0.48 g, 2.4 mmol) in dichloromethane (50 mL) was added dropwise and the solution stirred at −78° C. for 1 h, before triethylamine (2.5 mL, 18 mmol) was added slowly. The reaction was allowed to warm to room temperature and after 2 h the reaction was quenched by addition of water. Removal of the solvent in vacuo yielded the title compound, which was used in the next step without further purification.

b) 1-{2-[(2R)-4-(6-Fluoro-1-naphthyl)-2-methylpiperazinyl]ethyl}-3,4-dihydro-1H-2-benzopyran-6-carbonitrile To a stirred solution of 1-(2-oxoethyl)-3,4-dihydro-1H-2-benzopyran-6-carbonitrile (0.454 g, 2.26 mmol) in methanol (30 mL) was added (3R)-1-(6-fluoro-1-naphthyl)-3-methylpiperazine (0.61 g, 2.49 mmol), and the mixture stirred for 10 min. Sodium cyanoborohydride (0.157 g, 2.49 mmol) and acetic acid (0.25 mL) were added and the mixture stirred for 18 h. A further portion of sodium cyanoborohydride (0.20 g) was added and the reaction stirred for 6 h. The mixture was quenched with water, and the solvent removed in vacuo. Water was added and the mixture extracted with chloroform, the organic extracts dried ($MgSO_4$), filtered and evaporated in vacuo. The crude product was purified by preparative LC-MS to yield the title compound as a yellow oil.

c) 1-{2-[(2R)-4-(6-Fluoro-1-naphthyl)-2-methylpiperazinyl]ethyl}-3,4-dihydro-1H-2-benzopyran-6-yl)methanamine 1-{2-[(2R)-4-(6-Fluoro-1-naphthyl)-2-methylpiperazinyl]ethyl}-3,4-dihydro-1H-2-benzopyran-6-carbonitrile was reduced with lithium aluminium hydride, as described for Example 12d).

d) N-[((1S)-1-{2-[(2R)-4-(6-Fluoro-1-naphthyl)-2-methylpiperazinyl]ethyl}-3,4-dihydro-1H-2-benzopyran-6-yl)methyl]acetamide To a solution of 1-{2-[(2R)-4-(6-fluoro-1-naphthyl)-2-methyl-piperazinyl]ethyl}-3,4-dihydro-1H-2-benzopyran-6-yl)methanamine (0.11 g, 0.25 mmol) in dry dichloromethane (10 mL) under nitrogen was added triethylamine (0.3 mL), then acetyl chloride (0.5 mL, 0.5 mmol), and the mixture stirred at room temperature for 1 h. The reaction was quenched with water and the organic layer dried ($MgSO_4$), filtered and evaporated in vacuo. The crude product was purified by preparative LC-MS to yield the title compound as a white solid. M+H=522.

EXAMPLE 15

N-[((1S)-1-{2-[(2R)-4-(6-Fluoro-1-naphthyl)-2-methylpiperazinyl]ethyl}-3,4-dihydro-1H-2-benzopyran-6-yl)methyl]methanesulfonamide 1-{2-[(2R)-4-(6-Fluoro-1-naphthyl)-2-methylpiperazinyl]ethyl}-3,4-dihydro-1H-2-benzopyran-6-yl)methanamine was acylated with methanesulfonyl chloride as described for Example 14d), to yield the title compound. M+H=512.

EXAMPLE 16

5-[(3R)-3-Methyl-4-(2-{(1S)-6-[(2-oxo-1,3-oxazolidin-3-yl)methyl]-3,4-dihydro-1H-2-benzopyran-1-yl}ethyl)piperazinyl]-2-naphthonitrile a) 2-((1S)-6-Bromo-3,4-dihydro-1H-2-benzopyran-1-yl)ethyl tert-butyl(diphenyl)silyl ether To a solution of 2-((1S)-6-bromo-3,4-dihydro-1H-2-benzopyran-1-yl)ethanol (3.0 g, 11.7 mmol) in dry THF (100 mL) was added imidazole (3.97 g, 58.4 mmol) and chlorotert-butyl(diphenyl)silane (6.42 g, 23.4 mmol), and the mixture stirred under nitrogen at room temperature for 20 h. Diethyl ether was added and the mixture filtered through a pad of silica. The filtrate was evaporated in vacuo and the crude product purified by flash chromatography on silica, eluting with ethyl acetate/heptane (0:10 to 2:8), to yield the title compound.

b) (1S)-1-(2-{[tert-Butyl(diphenyl)silyl]oxy}ethyl)-3,4-dihydro-1H-2-benzopyran-6-carbaldehyde To a stirred solution of 2-((1S)-6-bromo-3,4-dihydro-1H-2-benzopyran-1-yl)ethyl tert-butyl(diphenyl)silyl ether (2.5 g, 5.05 mmol) in dry THF (60 mL), cooled to −78° C. under nitrogen, was slowly added n-butyllithium (2.5M in THF) (5.4 mL, 13.5 mmol). After 30 min stirring at −78° C., dry dimethylformamide (3.5 mL, 45 mmol) was added and the reaction allowed to warm to room temperature overnight. The reaction was quenched by addition of water and extracted into ethyl acetate. The combined organic extracts were washed with brine, dried ($MgSO_4$), filtered and evaporated in vacuo. The resultant yellow oil was purified by flash chromatography on silica, eluting with ethyl acetate/hexane (0:4 to 1:3), to yield the title compound as a colourless oil.

c) [(1S)-1-(2-{[tert-Butyl(diphenyl)silyl]oxy}ethyl)-3,4-dihydro-1H-2-benzopyran-6-yl]methanol To a stirred solution of (1S)-1-(2-{[tert-butyl(diphenyl)silyl]oxy}ethyl)-3,4-dihydro-1H-2-benzopyran-6-carbaldehyde (0.97 g, 2.18 mmol) in ethanol (30 mL) was added sodium borohydride (0.116 g, 3.06 mmol) and the mixture stirred for 1.5 h at room temperature. The reaction was extracted from water into ethyl acetate, the combined organic extracts dried ($MgSO_4$), filtered and evaporated in vacuo, to yield the title compound as a colourless oil.

d) 3-{[(1S)-1-(2-{[tert-Butyl(diphenyl)silyl]oxy}ethyl)-3,4-dihydro-1H-2-benzopyran-6-yl]methyl}-1,3-oxazolidin-2-one To a stirred solution of [(1S)-1-(2-{[tert-butyl(diphenyl)silyl]oxy}ethyl)-3,4-dihydro-1H-2-benzopyran-6-yl]methanol (0.30 g, 0.67 mmol) in dry diethyl ether (5 mL) and triethylamine (0.11 mL, 0.80 mmol) was added methanesulfonyl chloride (0.057 mL, 0.74 mmol), and the mixture stirred for 2 h under nitrogen. In a separate flask, sodium hydride (60% suspension in oil) (0.107 g, 2.68 mmol) was added to a stirred solution of 1,3-oxazolidin-2-one (0.175 g, 2.1 mmol) and the mixture heated at 50° C. for 2 h. To this solution was added the filtered solution of the mesylate and the mixture heated at 50° C. with stirring for a further 1.5 h, then stirred at room temperature overnight. Ethyl acetate and water were added to the reaction, the organic layer washed with brine, dried ($MgSO_4$), filtered and evaporated in vacuo. The crude product was purified by flash chromatography on silica, eluting with ethyl acetate/hexane (1:99 to 60:40), to yield the title compound.

e) 3-{[(1S)-1-(2-Hydroxyethyl)-3,4-dihydro-1H-2-benzopyran-6-yl]methyl}-1,3-oxazolidin-2-one To a stirred solution of 3-{[(1S)-1-(2-{[tert-butyl(diphenyl)silyl]oxy}ethyl)-3,4-dihydro-1H-2-benzopyran-6-yl]methyl}-1,3-oxazolidin-2-one (0.22 g, 0.43 mmol) in dry THF (30 ml) was added tetrabutylammonium fluoride (1M solution in THF) (0.51 mL, 0.51 mmol) and the reaction stirred at room temperature under nitrogen over the weekend. The reaction was quenched by addition of water and extracted with dichloromethane. The combined organic extracts were dried ($MgSO_4$), filtered and evaporated in vacuo. The crude product was purified by flash chromatography on silica, eluting with methanol/dichloromethane (1:9), to yield the title compound as a colourless oil.

f) 5-[(3R)-3-Methyl-4-(2-{(1S)-6-[(2-oxo-1,3-oxazolidin-3-yl)methyl]-3,4-dihydro-1H-2-benzopyran-1-yl}ethyl)piperazinyl]-2-naphthonitrile 3-{[(1S)-1-(2-Hydroxyethyl)-3,4-dihydro-1H-2-benzopyran-6-yl]methyl}-1,3-oxazolidin-2-one was reacted with methanesulfonyl chloride, as described for the preparation of 2-[(1S)-6-(aminocarbonyl)-3,4-dihydro-1H-2-benzopyran-1-yl]ethyl methanesulfonate. The resultant crude mesylate was then condensed with (3R)-1-(6-cyano-1-naphthyl)-3-methylpiperazine, as described for Example 1b), to yield the title compound. M+H=511.

The following Examples were similarly prepared, replacing the 1,3-oxazolidin-2-one in Example 16d) with the appropriate heterocycle and increasing the reaction time with the mesylate from 1.5 h to 3 h at 50° C.:

EXAMPLE 17

3-[((1S)-1-{2-[(2R)-4-(1,2-Dihydro-5-acenaphthylenyl)-2-methylpiperazinyl]ethyl}-3,4-dihydro-1H-2-benzopyran-6-yl)methyl]-1,3-oxazolidin-2-one Prepared from 1,3-oxazolidin-2-one. M+H=512.

EXAMPLE 18

3-[(3R)-3-Methyl-4-(2-{(1S)-6-[(2-oxo-1,3-oxazolidin-3-yl)methyl]-3,4-dihydro-1H-2-benzopyran-1-yl}ethyl)-piperazinyl]-1-benzothiophene-6-carbonitrile Prepared from 1,3-oxazolidin-2-one. M+H=517.

EXAMPLE 19

1-[((1S)-1-{2-[(2R)-4-(1,2-Dihydro-5-acenaphthylenyl)-2-methylpiperazinyl]ethyl}-3,4-dihydro-1H-2-benzopyran-6-yl)methyl]-2-pyrrolidinone Prepared from 2-pyrrolidinone. M+H=510.

EXAMPLE 20

3-[(3R)-3-Methyl-4-(2-{(1S)-6-[(2-oxo-1-pyrrolidinyl)methyl]-3,4-dihydro-1H-2-benzopyran-1-yl}ethyl)piperazinyl]-1-benzothiophene-6-carbonitrile Prepared from 2-pyrrolidinone. M+H=515.

EXAMPLE 21

(2R)-4-(1,2-Dihydro-5-acenaphthylenyl)-1-{2-[(1S)-6-(1H-imidazol-1-ylmethyl)-3,4-dihydro-1H-2-benzopyran-1-yl]ethyl}-2-methylpiperazine Prepared from imidazole. M+H=493.

EXAMPLE 22

3-((3R)-4-{2-[(1S)-6-(1H-Imidazol-1-ylmethyl)-3,4-dihydro-1H-2-benzopyran-1-yl]ethyl}-3-methylpiperazinyl)-1-benzothiophene-6-carbonitrile Prepared from imidazole. M+H=498.

EXAMPLE 23

3-((3R)-3-Methyl-4-{2-[(1S)-6-(1H-pyrazol-1-ylmethyl)-3,4-dihydro-1H-2-benzopyran-1-yl]ethyl}piperazinyl)-1-benzothiophene-6-carbonitrile Prepared from pyrazole. M+H=498.

EXAMPLE 24

(1S)-1-{2-[(2R)-4-(6-Fluoro-1-naphthyl)-2-methylpiperazinyl]ethyl}-3,4-dihydro-1H-2-benzopyran-6-amine a) (1S)-1-(2-{[tert-Butyl(dimethyl)silyl]oxy}ethyl)-N-(diphenylmethylene)-3,4-dihydro-1H-2-benzopyran-6-amine {2-[(1S)-6-Bromo-3,4-dihydro-1H-2-benzopyran-1-yl]ethoxy}(tert-butyl)dimethylsilane (1.86 g, mmol) was dissolved in dry toluene (25 mL), tris(dibenzylideneacetone)dipalladium (0.234 g, mmol) added and the mixture degassed by alternate evacuation and flushing with nitrogen. BINAP (0.495 g, mmol), sodium tert-butoxide (0.769 g, mmol) and benzophenone imine (1 mL) were added with stirring and the reaction heated at 90° C. under nitrogen for 18 h. The mixture was cooled, diluted with diethyl ether and filtered through celite. The crude product was evaporated in vacuo and used in the next step without further purification.

b) 2-{(1S)-6-[(Diphenylmethylene)amino]-3,4-dihydro-1H-2-benzopyran-1-yl}ethanol (1S)-1-(2-{[tert-Butyl(dimethyl)silyl]oxy}ethyl)-N-(diphenylmethylene)-3,4-dihydro-1H-2-benzopyran-6-amine was deprotected with aqueous acetic acid, as described for the preparation of (1S)-1-(2-hydroxyethyl)-3,4-dihydro-1H-2-benzopyran-6-carboxamide, to yield 2-{(1S)-6-[(diphenylmethylene)amino]-3,4-dihydro-1H-2-benzopyran-1-yl}ethanol.

c) 2-{(1S)-6-[(Diphenylmethylene)amino]-3,4-dihydro-1H-2-benzopyran-1-yl}ethyl methanesulfonate 2-{(1S)-6-[(Diphenylmethylene)amino]-3,4-dihydro-1H-2-benzopyran-1-yl}ethanol was reacted with methanesulfonyl chloride, as described for the preparation of 2-[(1S)-6-(aminocarbonyl)-3,4-dihydro-1H-2-benzopyran-1-yl]ethyl methanesulfonate, to yield 2-{(1S)-6-[(diphenylmethylene)amino]-3,4-dihydro-1H-2-benzopyran-1-yl}ethyl methanesulfonate.

d) (1S)-N-(Diphenylmethylene)-1-{2-[(2R)-4-(6-fluoro-1-naphthyl)-2-methylpiperazinyl]ethyl}-3,4-dihydro-1H-2-benzopyran-6-amine 2-{(1S)-6-[(Diphenylmethylene)amino]-3,4-dihydro-1H-2-benzopyran-1-yl}ethyl methanesulfonate was coupled with (3R)-1-(6-fluoro-1-naphthyl)-3-methylpiperazine, as described for Example 1b), to yield (1S)-N-(diphenylmethylene)-1-{2-[(2R)-4-(6-fluoro-1-naphthyl)-2-methylpiperazinyl]ethyl}-3,4-dihydro-1H-2-benzopyran-6-amine.

e) (1S)-1-{2-[(2R)-4-(6-Fluoro-1-naphthyl)-2-methylpiperazinyl]ethyl}-3,4-dihydro-1H-2-benzopyran-6-amine To a solution of (1S)-N-(diphenylmethylene)-1-{2-[(2R)-4-(6-fluoro-1-naphthyl)-2-methylpiperazinyl]-ethyl}-3,4-dihydro-1H-2-benzopyran-6-amine (1.46 g, 2.5 mmol) in methanol (25 mL) was added sodium acetate (0.28 g, 2.65 mmol) and hydroxylamine hydrochloride (0.194 g, 2.8 mmol), and the mixture stirred at room temperature under nitrogen for 18 h. Water was added and extracted with dichloromethane. The combined organic extracts were dried (MgSO$_4$), filtered and evaporated in vacuo. The crude product was purified by flash chromatography on silica, eluting with methanol/ethyl acetate (0:100 to 15:85), to yield (1S)-1-{2-[(2R)-4-(6-fluoro-1-naphthyl)-2-methylpiperazinyl]ethyl}-3,4-dihydro-1H-2-benzopyran-6-amine. M+H=420.

The following amines were similarly prepared from 2-{(1S)-6-[(diphenylmethylene)amino]-3,4-dihydro-1H-2-benzopyran-1-yl}ethyl methanesulfonate and the appropriate aryl piperazine, and subsequently further. derivativatised as described below:

(1S)-1-{2-[(2R)-4-(6-Cyano-1-naphthyl)-2-methylpiperazinyl]ethyl}-3,4-dihydro-1H-2-benzopyran-6-amine (1S)-1-{2-[(2R)-4-(1,2-Dihydro-5-acenaphthylenyl)-2-methylpiperazinyl]ethyl}-3,4-dihydro-1H-2-benzopyran-6-amine (1S)-1-{2-[(2R)-4-(6-Cyano-1-benzothien-3-yl)-2-methylpiperazinyl]ethyl}-3,4-dihydro-1H-2-benzopyran-6-amine

EXAMPLE 25

3-((1S)-1-{2-[(2R)-4-(6-Fluoro-1-naphthyl)-2-methylpiperazinyl]ethyl}-3,4-dihydro-1H-2-benzopyran-6-yl)-1,3-oxazolidin-2-one To a solution of (1S)-1-{2-[(2S)-4-(6-fluoro-1-naphthyl)-2-methyl-piperazinyl]ethyl}-3,4-dihydro-1H-2-benzopyran-6-amine (0.217 g, mmol) in dry DMF (5 mL) was added pyridine (0.05 mL, mmol) and 2-chloroethyl chloroformate (0.055 mL, mmol), and the reaction stirred at room temperature under nitrogen for 2 h. The reaction was quenched by addition of 2M sodium hydroxide (3 mL), diluted with water and extracted into dichloromethane. The combined organic extracts were dried (MgSO$_4$), filtered and evaporated in vacuo. The crude product was purified by prep LCMS to yield 3-((1S)-1-{2-[(2R)-4-(6-fluoro-1-naphthyl)-2-methylpiperazinyl]-ethyl}-3,4-dihydro-1H-2-benzopyran-6-yl)-1,3-oxazolidin-2-one. M+H=490.

EXAMPLE 26

3-((1S)-1-{2-[(2R)-4-(6-Cyano-1-naphthyl)-2-methylpiperazinyl]ethyl}-3,4-dihydro-1H-2-benzopyran-6-yl)-1,3-oxazolidin-2-one Prepared from (1S)-1-{2-[(2R)-4-(6-cyano-1-naphthyl)-2-methylpiperazinyl]ethyl}-3,4-dihydro-1H-2-benzopyran-6-amine, as described for Example 25. M+H=497.

EXAMPLE 27

3-((1S)-1-{2-[(2R)-4-(1,2-dihydro-5-acenaphthylenyl)-2-methylpiperazinyl]ethyl}-3,4-dihydro-1H-2-benzopyran-6-yl)-1,3-oxazolidin-2-one Prepared from (1S)-1-{2-[(2R)-4-(1,2-dihydro-5-acenaphthylenyl)-2-methylpiperazinyl]ethyl}-3,4-dihydro-1H-2-benzopyran-6-amine, as described for Example 25. M+H=498.

EXAMPLE 28

3-((1S)-1-{2-[(2R)-4-(6-Cyano-1-benzothien-3-yl)-2-methylpiperazinyl]ethyl}-3,4-dihydro-1H-2-benzopyran-6-yl)-1,3-oxazolidin-2-one Prepared from (1S)-1-{2-[(2R)-4-(6-cyano-1-benzothien-3-yl)-2-methylpiperazinyl]ethyl}-3,4-dihydro-1H-2-benzopyran-6-amine, as described for Example 25. M+H=503.

EXAMPLE 29

1-((1S)-1-{2-[(2R)-4-(6-fluoro-1-naphthyl)-2-methylpiperazinyl]ethyl}-3,4-dihydro-1H-2-benzopyran-6-yl)-2-pyrrolidinone The title compound was prepared as described for Example 25, substituting 4-bromobutyryl chloride for 2-chloroethyl chloroformate. M+H=488.

EXAMPLE 30

1-((1S)-1-{2-[(2R)-4-(6-Cyano-1-naphthyl)-2-methylpiperazinyl]ethyl}-3,4-dihydro-1H-2-benzopyran-6-yl)-2-pyrrolidinone Prepared from (1S)-1-{2-[(2R)-4-(6-cyano-1-naphthyl)-2-methylpiperazinyl]ethyl}-3,4-dihydro-1H-2-benzopyran-6-amine, as described for Example 29. M+H=495.

EXAMPLE 31

1-((1S)-1-{2-[(2R)-4-(6-cyano-1-benzothien-3-yl)-2-methylpiperazinyl]ethyl}-3,4-dihydro-1H-2-benzopyran-6-yl)-2-pyrrolidinone Prepared from (1S)-1-{2-[(2R)-4-(6-cyano-1-benzothien-3-yl)-2-methylpiperazinyl]ethyl}-3,4-dihydro-1H-2-benzopyran-6-amine, as described for Example 29. M+H=501.

EXAMPLE 32

1-((1S)-1-{2-[(2R)-4-(6-fluoro-1-naphthyl)-2-methylpiperazinyl]ethyl}-3,4-dihydro-1H-2-benzopyran-6-yl)-2-azetidinone The title compound was prepared as described for Example 25, substituting 3-brompropionyl chloride for 2-chloroethyl chloroformate and maintaining the reaction for 3 days. M+H=474.

EXAMPLE 33

1-((1S)-1-{2-[(2R)-4-(6-cyano-1-naphthyl)-2-methylpiperazinyl]ethyl}-3,4-dihydro-1H-2-benzopyran-6-yl)-2-azetidinone Prepared from (1S)-1-{2-[(2R)-4-(6-cyano-1-naphthyl)-2-methylpiperazinyl]ethyl}-3,4-dihydro-1H-2-benzopyran-6-amine, as described for Example 32. M+H=481.

EXAMPLE 34

(2R)-4-(1,2-Dihydro-5-acenaphthylenyl)-1-{2-[(1S)-6-(1,1-dioxido-2-isothiazolidinyl)-3,4-dihydro-1H-2-benzopyran-1-yl]ethyl}-2-methylpiperazine a) N-[(1S)-1-(2-{[tert-Butyl(dimethyl)silyl]oxy}ethyl)-3,4-dihydro-1H-2-benzopyran-6-yl]-3-chloro-1-propanesulfonamide To a stirred solution of (1S)-1-(2-{[tert-butyl(dimethyl)silyl]oxy}ethyl)-3,4-dihydro-1H-2-benzopyran-6-amine (0.15 g, 0.49 mmol) in ethyl acetate (18 mL), cooled to 0° C., was added triethylamine (0.274 mL, 1.37 mmol) then 3-chloro-1-propanesulfonyl chloride (0.070 mL, 0.576 mmol), and the reaction mixture allowed to warm to room temperature. After stirring for 1 h, the reaction was basified with 1N sodium hydroxide (2.5 mL), and extracted with ethyl acetate. The combined organic extracts were washed with brine, dried (MgSO$_4$), filtered and evaporated in vacuo to yield the title compound as an oil. This crude product was used in the next step without further purification.

b) 2-[(1S)-1-(2-{[tert-Butyl(dimethyl)silyl]oxy}ethyl)-3,4-dihydro-1H-2-benzopyran-6-yl]isothiazolidine 1,1-dioxide To a stirred solution of N-[(1S)-1-(2-{[tert-butyl(dimethyl)silyl]oxy}ethyl)-3,4-dihydro-1H-2-benzopyran-6-yl]-3-chloro-1-propanesulfonamide (0.367 g, 0.82 mmol) in DMF (8 mL), cooled to 0° C., was added sodium hydride (60% dispersion in oil) (0.036 g, 0.9 mmol) and the mixture allowed to warm to room temperature. After 30 min, the reaction was quenched by addition of water and extracted with ethyl acetate. The combined organic extracts were washed with brine, dried (MgSO$_4$), filtered and evaporated in vacuo. The title compound, as an oil, was used in the next step without further purification.

c) 2-[(1S)-6-(1,1-Dioxido-2-isothiazolidinyl)-3,4-dihydro-1H-2-benzopyran-1-yl]ethanol Prepared from 2-[(1S)-1-(2-{[tert-butyl(dimethyl)silyl]oxy}ethyl)-3,4-dihydro-1H-2-benzopyran-6-yl]isothiazolidine 1,1-dioxide, as described for the preparation of (1S)-1-(2-hydroxyethyl)-3,4-dihydro-1H-2-benzopyran-6-carboxamide.

d) (2R)-4-(1,2-Dihydro-5-acenaphthylenyl)-1-{2-[(1S)-6-(1,1-dioxido-2-isothiazolidinyl)-3,4-dihydro-1H-2-benzopyran-1-yl]ethyl}-2-methylpiperazine 2-[(1S)-6-(1,1-Dioxido-2-isothiazolidinyl)-3,4-dihydro-1H-2-benzopyran-1-yl]ethanol was reacted with methanesulfonyl chloride, as described for the preparation of 2-[(1S)-6-(aminocarbonyl)-3,4-dihydro-1H-2-benzopyran-1-yl]ethyl methanesulfonate. The resultant crude mesylate was then condensed with (3R)-1-(1,2-dihydro-5-acenaphthylenyl)-3-methylpiperazine, as described for Example 1b), to yield the title compound. M+H=532.

EXAMPLE 35

1-((1S)-1-{2-[(2R)-4-(6-Cyano-1-benzothien-3-yl)-2-methylpiperazinyl]ethyl}-3,4-dihydro-1H-2-benzopyran-6-yl)-2-imidazolidinone Method A a) 2-((1S)-6-Bromo-3,4-dihydro-1H-2-benzopyran-1-yl)ethyl methanesulfonate The title compound was prepared from 2-((1S)-6-bromo-3,4-dihydro-1H-2-benzopyran-1-yl)ethanol and methanesulfonyl chloride, as described for the preparation of 2-[(1S)-6-(aminocarbonyl)-3,4-dihydro-1H-2-benzopyran-1-yl]ethyl methanesulfonate.

b) 3-((3R)-4-{2-[(1S)-6-Bromo-3,4-dihydro-1H-2-benzopyran-1-yl]ethyl}-3-methylpiperazinyl)-1-benzothiophene-6-carbonitrile The title compound was prepared from 2-((1S)-6-bromo-3,4-dihydro-1H-2-benzopyran-1-yl)ethyl methanesulfonate and (3R)-1-(6-cyano-1-benzothien-3-yl)-3-methylpiperazine, as described for Example 1b).

c) 1-((1S)-1-{2-[(2R)-4-(6-Cyano-1-benzothien-3-yl)-2-methylpiperazinyl]ethyl}-3,4-dihydro-1H-2-benzopyran-6-yl)-2-imidazolidinone 3-((3R)-4-{2-[(1S)-6-Bromo-3,4-dihydro-1H-2-benzopyran-1-yl]ethyl}-3-methylpiperazinyl)-1-benzothiophene-6-carbonitrile (0.36 g, 0.73 mmol) was dissolved in dry toluene (15 mL) and degassed. 2-Imidazolidinone (0.071 g, 0.82 mmol), tris(dibenzylideneacetone)dipalladium (34 mg), (+/−)-2,2'-bis(diphenylphosphino)-1,1'-binaphthyl (47 mg) and caesium carbonate (0.34 g, 1.05 mmol) were added and the mixture heated under reflux with stirring, under a nitrogen atmosphere, for 2 days. The reaction was cooled to room temperature, diluted with dichloromethane, filtered through celite and washed with water. The organic extracts were Method B a) 3-[(1S)-1-(2-Hydroxyethyl)-3,4-dihydro-1H-2-benzopyran-6-yl]-1,3-oxazolidin-2-one To a stirred solution of 2-((1S)-6-bromo-3,4-dihydro-1H-2-benzopyran-1-yl)ethanol (0.815 g, 3.17 mmol) in dry dioxan (5 mL) was added 1,3-oxazolidin-2-one (0.26 g, 2.95 mmol), trans-1,2-cyclohexanediamine (0.05 mL, 0.42 mmol), copper(I) iodide (0.040 g, 0.21 mmol) and potassium carbonate (1.02 g, 7.36 mmol), and the mixture heated at reflux under nitrogen overnight. 2M Ammonia was added and the mixture extracted into dichloromethane. The combined organic extracts were dried (MgSO$_4$), filtered and evaporated in vacuo. The crude product was purified by flash chromatography on silica to yield the title compound.

b) 2-((1S)-6-(2-Oxo-imidazolidin-1-yl)-3,4-dihydro-1H-2-benzopyran-1-yl)ethyl methanesulfonate Prepared from 3-[(1S)-1-(2-hydroxyethyl)-3,4-dihydro-1H-2-benzopyran-6-yl]-1,3-oxazolidin-2-one and methanesulfonyl chloride, as described for the preparation of 2-[(1S)-6-(aminocarbonyl)-3,4-dihydro-1H-2-benzopyran-1-yl]ethyl methanesulfonate c) 1-((1S)-1-{2-[(2R)-4-(6-Cyano-1-benzothien-3-yl)-2-methylpiperazinyl]ethyl}-3,4-dihydro-1H-2-benzopyran-6-yl)-2-imidazolidinone The title compound was prepared by condensation of 2-((1S)-6-(2-oxo-imidazolidin-1-yl)-3,4-dihydro-1H-2-benzopyran-1-yl)ethyl methanesulfonate and (3R)-1-(6-cyano-1-benzothien-3-yl)-3-methylpiperazine, as described for Example 1b). M+H=502.

EXAMPLE 36

1-((1S)-1-{2-[(2R)-4-(6-Fluoro-1-naphthyl)-2-methylpiperazinyl]ethyl}-3,4-dihydro-1H-2-benzopyran-6-yl)-2-imidazolidinone Prepared from (3R)-1-(6-cyano-1-naphthyl)-3-methylpiperazine, as described for Example 35, Method A. M+H=489.

EXAMPLE 37

1-((1S)-1-{2-[(2R)-4-(6-Cyano-1-benzothien-3-yl)-2-methylpiperazinyl]ethyl}-3,4-dihydro-1H-2-benzopyran-6-yl)-3-methyl-2-imidazolidinone Prepared as described for Example 35, Method B, substituting 1-methyl-2-imidazolidinone for 2-imidazolidinone. M+H=516.

EXAMPLE 38

3-((3R)-3-Methyl-4-{2-[(1S)-6-(4-thiomorpholinyl)-3,4-dihydro-1H-2-benzopyran-1-yl]ethyl}piperazinyl)-1-benzothiophene-6-carbonitrile a) 2-[(1S)-6-(4-Thiomorpholinyl)-3,4-dihydro-1H-2-benzopyran-1-yl]ethanol 2-((1S)-6-Bromo-3,4-dihydro-1H-2-benzopyran-1-yl)ethanol (0.26 g, 0.99 mmol) was dissolved in dry toluene (10 mL) and degassed. Thiomorpholine (0.14 mL, 1.48 mmol), tris(dibenzylideneacetone)dipalladium (51 mg), (+/−)-2,2'-bis(diphenylphosphino)-1,1'-binaphthyl (77 mg) and sodium tert-butoxide (0.126 g, 1.3 mmol) were added and the mixture heated under reflux with stirring, under a nitrogen atmosphere, for 24 h. The reaction was cooled to room temperature, diluted with dichloromethane, filtered through celite and washed with water. The organic extracts were dried (MgSO$_4$), filtered and evaporated in vacuo. The crude product was purified by flash chromatography on silica, to yield the title compound.

b) 2-[(1S)-6-(4-Thiomorpholinyl)-3,4-dihydro-1H-2-benzopyran-1-yl]ethyl methanesulfonate Prepared from 2-[(1S)-6-(4-thiomorpholinyl)-3,4-dihydro-1H-2-benzopyran-1-yl]ethanol and methanesulfonyl chloride, as described for the preparation of 2-[(1S)-6-(aminocarbonyl)-3,4-dihydro-1H-2-benzopyran-1-yl]ethyl methanesulfonate.

c) 3-((3R)-3-Methyl-4-{2-[(1S)-6-(4-thiomorpholinyl)-3,4-dihydro-1H-2-benzopyran-1-yl]ethyl}piperazinyl)-1-benzothiophene-6-carbonitrile Prepared by condensation of 2-[(1S)-6-(4-thiomorpholinyl)-3,4-dihydro-1H-2-benzopyran-1-yl]ethyl methanesulfonate with (3R)-1-(6-cyano-1-benzothien-3-yl)-3-methylpiperazine, as described for Example 1b). M+H=519.

EXAMPLE 39

3-((3R)-3-Methyl-4-{2-[(1S)-6-(4-morpholinyl)-3,4-dihydro-1H-2-benzopyran-1-yl]ethyl}piperazinyl)-1-benzothiophene-6-carbonitrile Prepared as described for Example 38, substituting thiomorpholine with morpholine. M+H=503.

EXAMPLE 40

(2R)-4-(1,2-Dihydro-5-acenaphthylenyl)-2-methyl-1-{2-[(1S)-6-(1H-pyrazol-1-yl)-3,4-dihydro-1H-2-benzopyran-1-yl]ethyl}piperazine a) 2-[(1S)-6-(1H-Pyrazol-1-yl)-3,4-dihydro-1H-2-benzopyran-1-yl]ethanol 2-((1S)-6-Bromo-3,4-dihydro-1H-2-benzopyran-1-yl)ethanol (0.54 g, 2.1 mmol), pyrazole (0.29 g, 4.3 mmol), copper(I) iodide (0.062 g, 0.33 mmol) and potassium carbonate (0.30 g, 2.2 mmol) were stirred in dry DMF (3 mL) under nitrogen and heated at 150° C. for 18 h. The reaction mixture was cooled and extracted from water into dichloromethane. The combined organic extracts were dried (MgSO$_4$), filtered and evaporated in vacuo. The crude product was used in the next step without further purification.

b) 2-[(1S)-6-(1H-Pyrazol-1-yl)-3,4-dihydro-1H-2-benzopyran-1-yl]ethyl methanesulfonate Prepared from 2-[(1S)-6-(1H-pyrazol-1-yl)-3,4-dihydro-1H-2-benzopyran-1-yl]ethanol and methanesulfonyl chloride, as described for the preparation of 2-[(1S)-6-(aminocarbonyl)-3,4-dihydro-1H-2-benzopyran-1-yl]ethyl methanesulfonate.

c) (2R)-4-(1,2-Dihydro-5-acenaphthylenyl)-2-methyl-1-{2-[(1S)-6-(1H-pyrazol-1-yl)-3,4-dihydro-1H-2-benzopyran-1-yl]ethyl}piperazine Prepared by condensation of 2-[(1S)-6-(1H-pyrazol-1-yl)-3,4-dihydro-1H-2-benzopyran-1-yl]ethyl methanesulfonate with (3R)-1-(1,2-dihydro-5-acenaphthylenyl)-3-methylpiperazine, as described for Example 1b). M+H=479.

The following Examples were similarly prepared, reacting 2-((1S)-6-bromo-3,4-dihydro-1H-2-benzopyran-1-yl)ethanol with the appropriate heterocycle, then condensation of the subsequent mesylate with the appropriate aryl piperazine:

EXAMPLE 41

3-((3R)-3-Methyl-4-{2-[(1S)-6-(1H-pyrazol-1-yl)-3,4-dihydro-1H-2-benzopyran-1-yl]ethyl}piperazinyl)-1-benzothiophene-6-carbonitrile Prepared from pyrazole. M+H=484.

EXAMPLE 42

(2R)-4-(1,2-Dihydro-5-acenaphthylenyl)-1-{2-[(1S)-6-(1H-imidazol-1-yl)-3,4-dihydro-1H-2-benzopyran-1-yl]ethyl}-2-methylpiperazine Prepared from imidazole. M+H=479.

EXAMPLE 43

3-((3R)-4-{2-[(1S)-6-(1H-Imidazol-1-yl)-3,4-dihydro-1H-2-benzopyran-1-yl]ethyl}-3-methylpiperazinyl)-1-benzothiophene-6-carbonitrile Prepared from imidazole. M+H=484.

EXAMPLE 44

(2R)-4-(1,2-Dihydro-5-acenaphthylenyl)-2-methyl-1-{2-[(1S)-6-(2H-1,2,3-triazol-2-yl)-3,4-dihydro-1H-2-benzopyran-1-yl]ethyl}piperazine Prepared from 1,2,3-triazole, to give a mixture with the 6-(triazol-1-yl)benzopyran, which was separated by preparative LC-MS. M+H=480.

EXAMPLE 45

(2R)-4-(1,2-Dihydro-5-acenaphthylenyl)-2-methyl-1-{2-[(1S)-6-(1H-1,2,3-triazol-1-yl)-3,4-dihydro-1H-2-benzopyran-1-yl]ethyl}piperazine Prepared from 1,2,3-triazole, to give a mixture with the 6-(triazol-2-yl)benzopyran, which was separated by preparative LC-MS. M+H=480.

EXAMPLE 46

3-((3R)-3-Methyl-4-{2-[(1S)-6-(2H-1,2,3-triazol-2-yl)-3,4-dihydro-1H-2-benzopyran-1-yl]ethyl}piperazinyl)-1-benzothiophene-6-carbonitrile Prepared from 1,2,3-triazole, to give a mixture with the 6-(triazol-1-yl)benzopyran, which was separated by preparative LC-MS. M+H=485.

EXAMPLE 47

3-((3R)-3-Methyl-4-{2-[(1S)-6-(1H-1,2,3-triazol-1-yl)-3,4-dihydro-1H-2-benzopyran-1-yl]ethyl}piperazinyl)-1-benzothiophene-6-carbonitrile Prepared from 1,2,3-triazole, to give a mixture with the 6-(triazol-2-yl)benzopyran, which was separated by preparative LC-MS. M+H=485.

EXAMPLE 48

(2R)-4-(1,2-Dihydro-5-acenaphthylenyl)-2-methyl-1-{2-[(1S)-6-(1H-1,2,4-triazol-1-yl)-3,4-dihydro-1H-2-benzopyran-1-yl]ethyl}piperazine Prepared from 1,2,4-triazole. M+H=480.

EXAMPLE 49

3-((3R)-3-Methyl-4-{2-[(1S)-6-(1H-1,2,4-triazol-1-yl)-3,4-dihydro-1H-2-benzopyran-1-yl]ethyl}piperazinyl)-1-benzothiophene-6-carbonitrile Prepared from 1,2,4-triazole. M+H=485.

EXAMPLE 50

1-((1S)-1-{2-[(2R)-4-(1,2-Dihydro-5-acenaphthylenyl)-2-methylpiperazinyl]ethyl}-3,4-dihydro-1H-2-benzopyran-6-yl)-2(1H)-pyridinone Prepared from 2-hydroxypyridine. M+H=506.

EXAMPLE 51

3-((3R)-3-Methyl-4-{2-[(1S)-6-(2-oxo-1(2H)-pyridinyl)-3,4-dihydro-1H-2-benzopyran-1-yl]ethyl}piperazinyl)-1-benzothiophene-6-carbonitrile Prepared from 2-hydroxypyridine. M+H=511.

The invention claimed is:
1. A compound of the formula

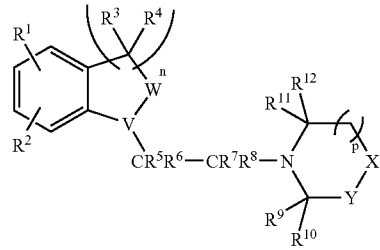

in which
R¹ is —CONR¹³R¹⁴ or —(CH₂)ᵣ—R²¹,
where R¹³ and R¹⁴ are each hydrogen or $C_{1-6}$ alkyl, or R¹³ and R¹⁴ taken together with the nitrogen atom to which they are attached form a morpholino, pyrrolidino or piperidinyl ring optionally substituted with one or two $C_{1-6}$ alkyl groups;
—R²¹ is

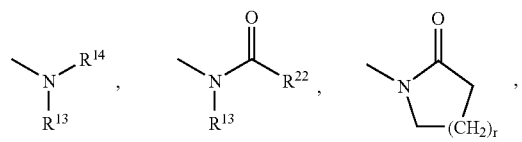

-continued where $R^{13}$, $R^{14}$, $R^{22}$ and $R^{23}$ are each hydrogen or $C_{1-6}$ alkyl, or $R^{13}$ and $R^{14}$ taken together with the nitrogen atom to which they are attached form a morpholino, pyrrolidino or piperidinyl ring optionally substituted with one or two $C_{1-6}$ alkyl groups;

$R^{24}$ is selected from hydrogen, $C_{1-6}$ alkyl, $C_{1-6}$ alkoxy, carboxy, hydroxy, cyano, halo, trifluoromethyl, nitro, amino, $C_{1-6}$ acylamino, $C_{1-6}$ alkylthio, phenyl or phenoxy;

$R^2$ is hydrogen, $C_{1-6}$ alkyl, $C_{1-6}$ alkoxy or halo;

$R^3$, $R^4$, $R^5$, $R^6$, $R^7$, and $R^8$ are each hydrogen or $C_{1-6}$ alkyl;

$R^9$, $R^{10}$, $R^{11}$ and $R^{12}$ are each hydrogen, $C_{1-6}$ alkyl or —$(CH_2)_q$—$OR^{20}$, wherein $R^{20}$ is $C_{1-6}$ alkyl;

n is 1 or 2;

p is 0, 1 or 2;

t is 0, 1, or 2;

—W—V— is —O—$CR^{25}$—;

$R^{25}$ is hydrogen or $C_{1-6}$ alkyl;

—X—Y— is $$-N(Z)-CH_2-$$

where Z is in which -T- is —$CH_2$—, —O—, —S—, C(O)— or —CH=CH—, and m and s are each 0 or 1; and $R^{15}$ and $R^{19}$ are each hydrogen, halo, $C_{1-6}$ alkyl or $C_{1-6}$ alkoxy, carboxy-$C_{1-6}$ alkyl, cyano, halogen, trifluoromethyl, trifluoromethoxy, nitro, amino, $C_1$-$C_6$ acylamino or $C_1$-$C_6$ alkylthio;

and provided that when -T- is —$CH_2$—, —O—, —S— or —C(O)—, then (m+s) is 1 or 2;

or a pharmaceutically acceptable salt thereof.

2. A compound according to claim 1 wherein -T- is —$CH_2$— and (m+s) is 1, or a pharmaceutically acceptable salt thereof.

3. A compound according to claim 1 wherein -T- is —CH=CH— and (m+s) is 0, or a pharmaceutically acceptable salt thereof.

4. A compound according to claim 1 wherein -T- is —C(O)— and (m+s) is 1, or a pharmaceutically acceptable salt thereof.

5. A compound according to claim 1 wherein -T- is —O—, m is 1 and s is 1, or a pharmaceutically acceptable salt thereof.

6. A compound according to claim 1 wherein -T- is —S—, m is 1 and s is 1, or a pharmaceutically acceptable salt thereof.

7. A compound according to claim 1 wherein $R^1$ is —$(CH_2)_t$—$R^{21}$, or a pharmaceutically acceptable salt thereof.

8. A compound according to claim 7 wherein -T- is —$CH_2$— and (m+s) is 1, or a pharmaceutically acceptable salt thereof.

9. A compound according to claim 1 of the formula wherein:

$R^9$ is $C_1$-$C_6$ alkyl and $R^{10}$ is hydrogen; and

—W— is —O—, or a pharmaceutically acceptable salt thereof.

10. A compound according to claim 9 wherein $R^9$ is $C_{1-6}$ alkyl and $R^{10}$, $R^{11}$ and $R^{12}$ are hydrogen, or a pharmaceutically acceptable salt thereof.

11. The compound which is (1S)-1-{2-[(2R)-4-(1,2-Dihydro-5-acenaphthylenyl)-2-methylpiperazinyl]ethyl}-3,4-dihydro-1H-2-benzopyran-6-carboxamide or a pharmaceutically acceptable salt thereof.

12. A pharmaceutical composition comprising a compound of claim 1, or a pharmaceutically acceptable salt thereof, together with a pharmaceutically acceptable diluent or carrier.

13. A pharmaceutical composition comprising the compound which is (1S-1-{2-[(2R)-4-(1,2-Dihydro-5-acenaphthylenyl)-2-methylpiperazinyl]ethyl}-3,4-dihydro-1H-2-benzopyran-6-carboxamide or a pharmaceutically acceptable salt thereof, together with a pharmaceutically acceptable diluent or carrier.

* * * * *